United States Patent
Lev et al.

(10) Patent No.: US 8,378,070 B2
(45) Date of Patent: *Feb. 19, 2013

(54) PEPTIDES FOR THE REGULATION OF NEUROTRANSMITTER SEQUESTRATION AND RELEASE

(75) Inventors: Nirit Lev, Ramat-Gan (IL); Daniel Offen, Kfar HaRoe (IL); Eldad Melamed, Tel-Aviv (IL)

(73) Assignee: Ramot at Tel-Aviv University Ltd., Tel-Aviv (IL)

( * ) Notice: Subject to any disclaimer, the term of this patent is extended or adjusted under 35 U.S.C. 154(b) by 475 days.

This patent is subject to a terminal disclaimer.

(21) Appl. No.: 12/450,076

(22) PCT Filed: Mar. 12, 2008

(86) PCT No.: PCT/IL2008/000336
§ 371 (c)(1),
(2), (4) Date: Nov. 24, 2009

(87) PCT Pub. No.: WO2008/111063
PCT Pub. Date: Sep. 18, 2008

(65) Prior Publication Data
US 2010/0093600 A1    Apr. 15, 2010

Related U.S. Application Data

(60) Provisional application No. 60/906,226, filed on Mar. 12, 2007.

(51) Int. Cl.
*A61K 38/00* (2006.01)
*A61K 38/18* (2006.01)
*A61P 25/00* (2006.01)
*A61P 25/28* (2006.01)

(52) U.S. Cl. .......... 530/327; 530/300; 514/1.1; 514/8.3; 514/17.7

(58) Field of Classification Search .................. None
See application file for complete search history.

(56) References Cited

U.S. PATENT DOCUMENTS

| 7,211,255 | B2 | 5/2007 | Klinefelter | |
|---|---|---|---|---|
| 2005/0069536 | A1* | 3/2005 | Klinefelter | 424/130.1 |
| 2006/0153807 | A1 | 7/2006 | Abeliovich et al. | |
| 2011/0212896 | A1 | 9/2011 | Offen et al. | |

FOREIGN PATENT DOCUMENTS

| WO | WO 2007/095530 | 8/2007 |
|---|---|---|
| WO | WO 2007/119237 | 10/2007 |
| WO | WO 2008/111063 | 9/2008 |

OTHER PUBLICATIONS

Sievert et al., Biochem J., 330:959-966, 1998.*
Official Action Dated Oct. 21, 2011 From the US Patent and Trademark Office Re. U.S. Appl. No. 13/127,494.
International Search Report and the Written Opinion Dated Jan. 7, 2011 From the International Searching Authority Re. Application No. PCT/IL2010/000760.
Mitsumoto et al. "DJ-1 Is an Indicator for Endogenous Reactive Oxygen Species Elicited by Endotoxin", Free Radical Research, XP002989099, 35(6): 885-893, Dec. 1, 2001.
Communication Relating to the Results of the Partial International Search Dated Jul. 28, 2008 From the International Searching Authority Re.: Application No. PCT/IL2008/000336.
International Search Report Dated Oct. 1, 2008 From the International Searching Authority Re.: Application No. PCT/IL2008/000336.
Written Opinion Dated Oct. 1, 2008 From the International Searching Authority Re.: Application No. PCT/IL2008/000336.
Chen et al. "Synaptophysin Enhances the Neuroprotection of VMAT2 in MPP+-Induced Toxicity in MN9D Cells", Neurobiology of Disease, XP004977685, 19(3): 419-426, Aug. 1, 2005.
Lev et al. "The Parkinson's Disease-Associated DJ-1 Protein Protects Against Dopamine Toxicity by Upregulating Its Vesicular Sequestration", Department of Neurology and Lab of Neuroscience, Rabin Medical Center, FMRC, Sackler Faculty of medicine, Tel Aviv University, Israel, Internet Article, XP002487471, p. 25, Dec. 27, 2006. <URL:http://www.israel-neurology.co.il/Abstract271206.pdf>. Abstract.
Pan et al. "Biological Effects of Pramipexole on Dopaminergic Neuron-Associated Genes: Relevance to Neuroprotection", Neuroscience Letters, XP004766570, 377(2): 106-109, Mar. 29, 2005.
Official Action Dated Sep. 2, 2011 From the US Patent and Trademark Office Re. U.S. Appl. No. 13/127,494.
International Preliminary Report on Patentability Dated Mar. 29, 2012 From the International Bureau of WIPO Re. Application No. PCT/IL2010/000760.

* cited by examiner

*Primary Examiner* — Daniel E Kolker
*Assistant Examiner* — Stacey MacFarlane

(57) ABSTRACT

A method of selecting an agent comprising a neuroprotecting activity is disclosed. The method comprises:
  (a) introducing a plurality of agents into a plurality of cells; and
  (b) analyzing Vesicular Monoamine Transporter 2 (VMAT2) transcription in the cells; and
  (c) identifying an agent of the plurality of agents capable of up-regulating DJ-1-dependent VMAT2 transcription in the cells, thereby selecting the agent comprising the neuroprotectingactivity.

6 Claims, 12 Drawing Sheets
(4 of 12 Drawing Sheet(s) Filed in Color)

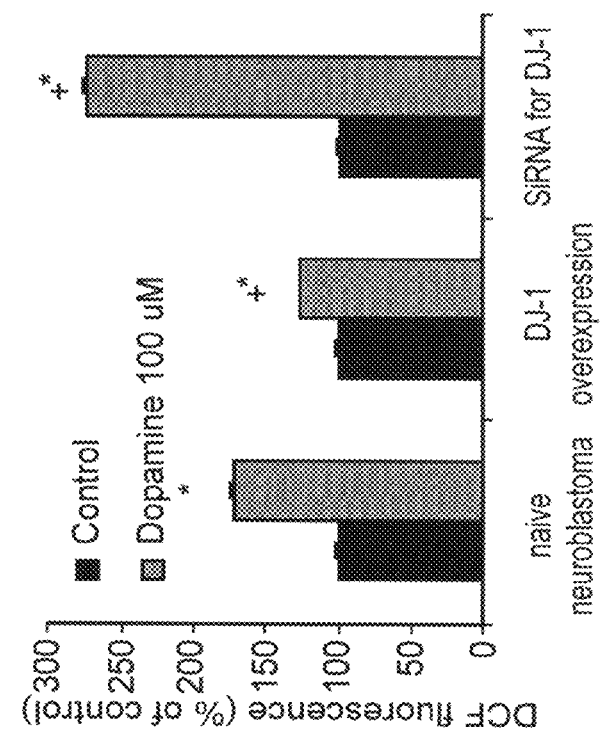
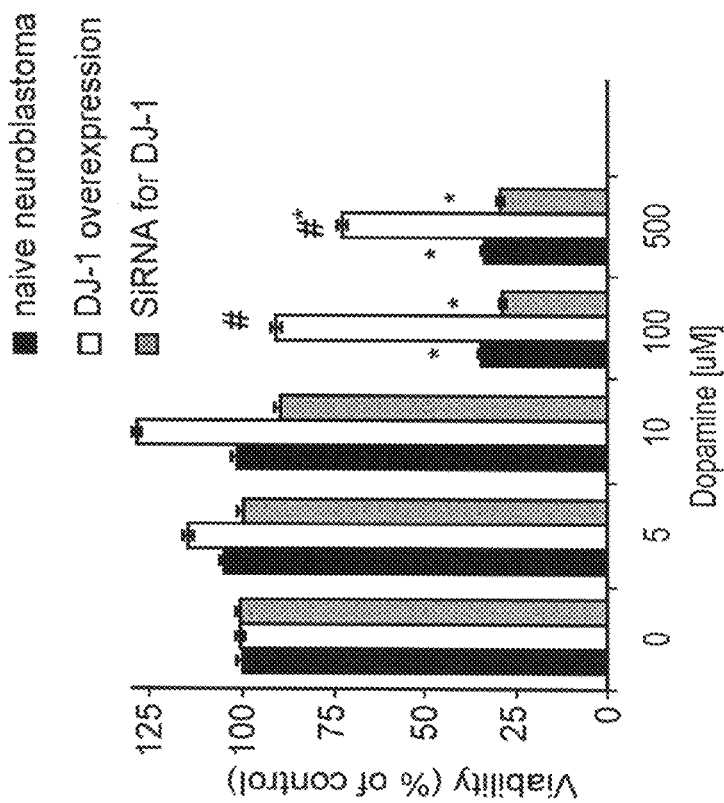
Fig. 1A
Fig. 1B

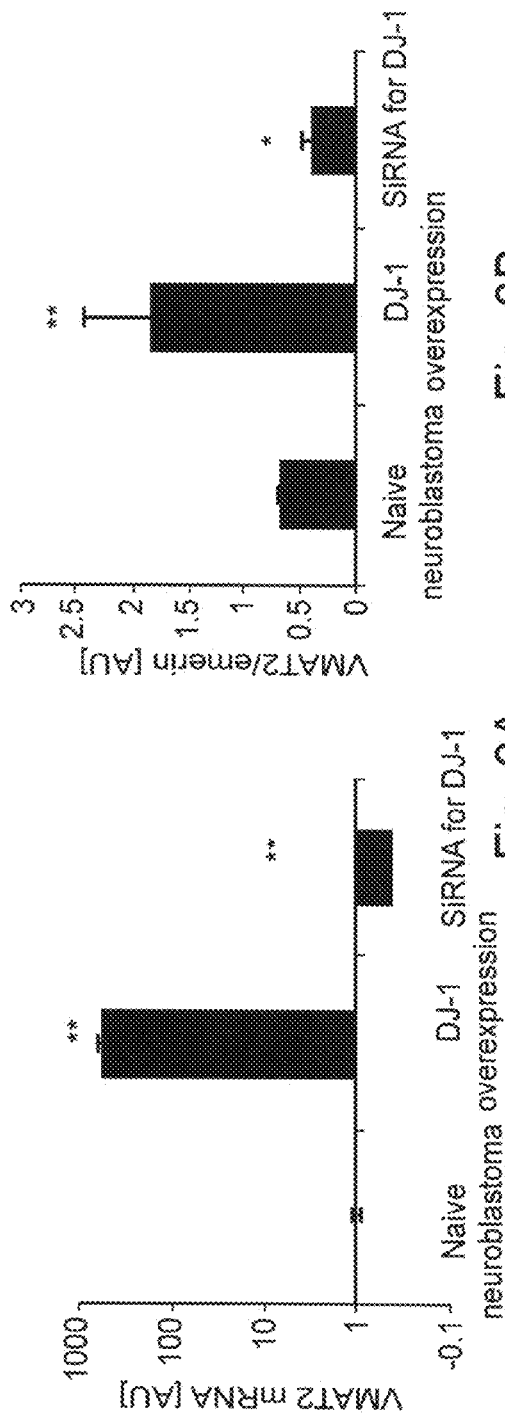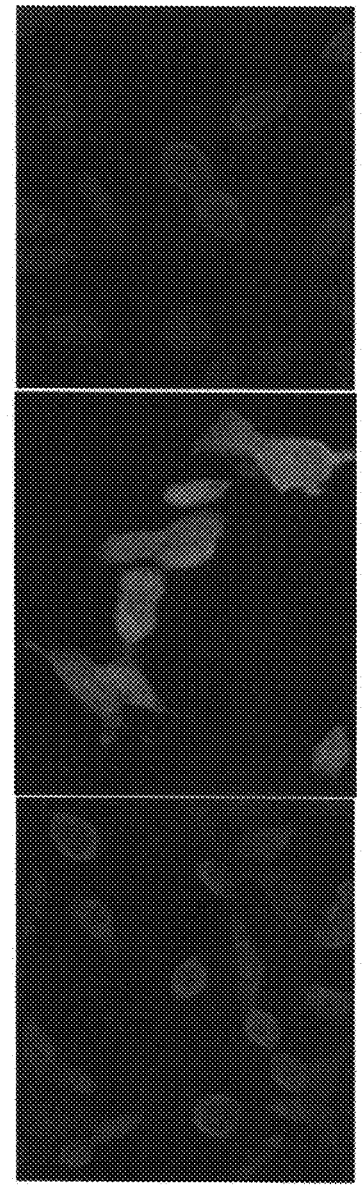
Fig. 3A  Fig. 3B  Fig. 3C  Fig. 3D  Fig. 3E

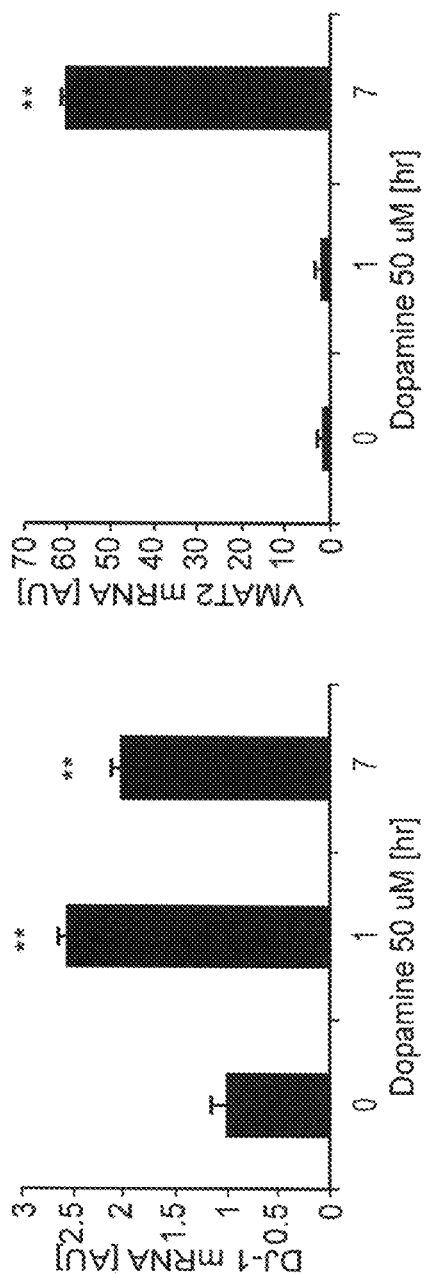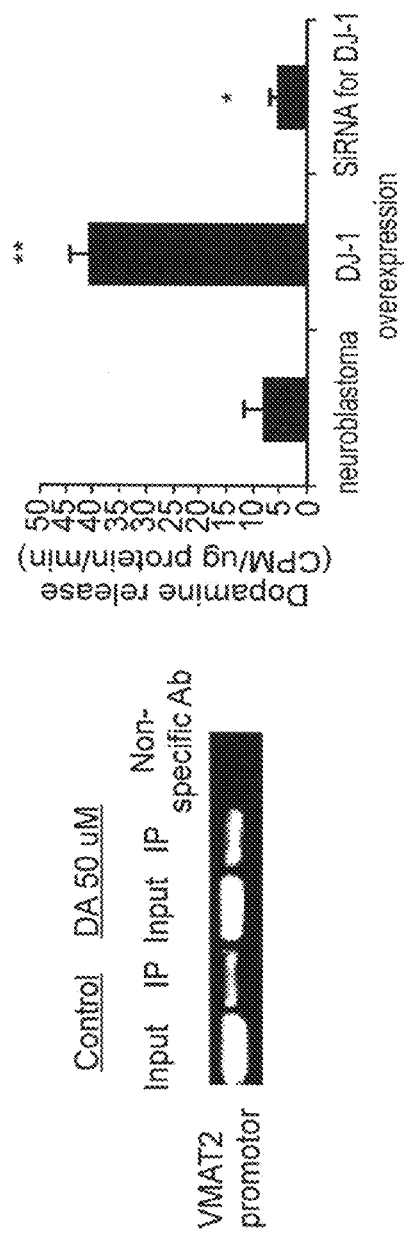

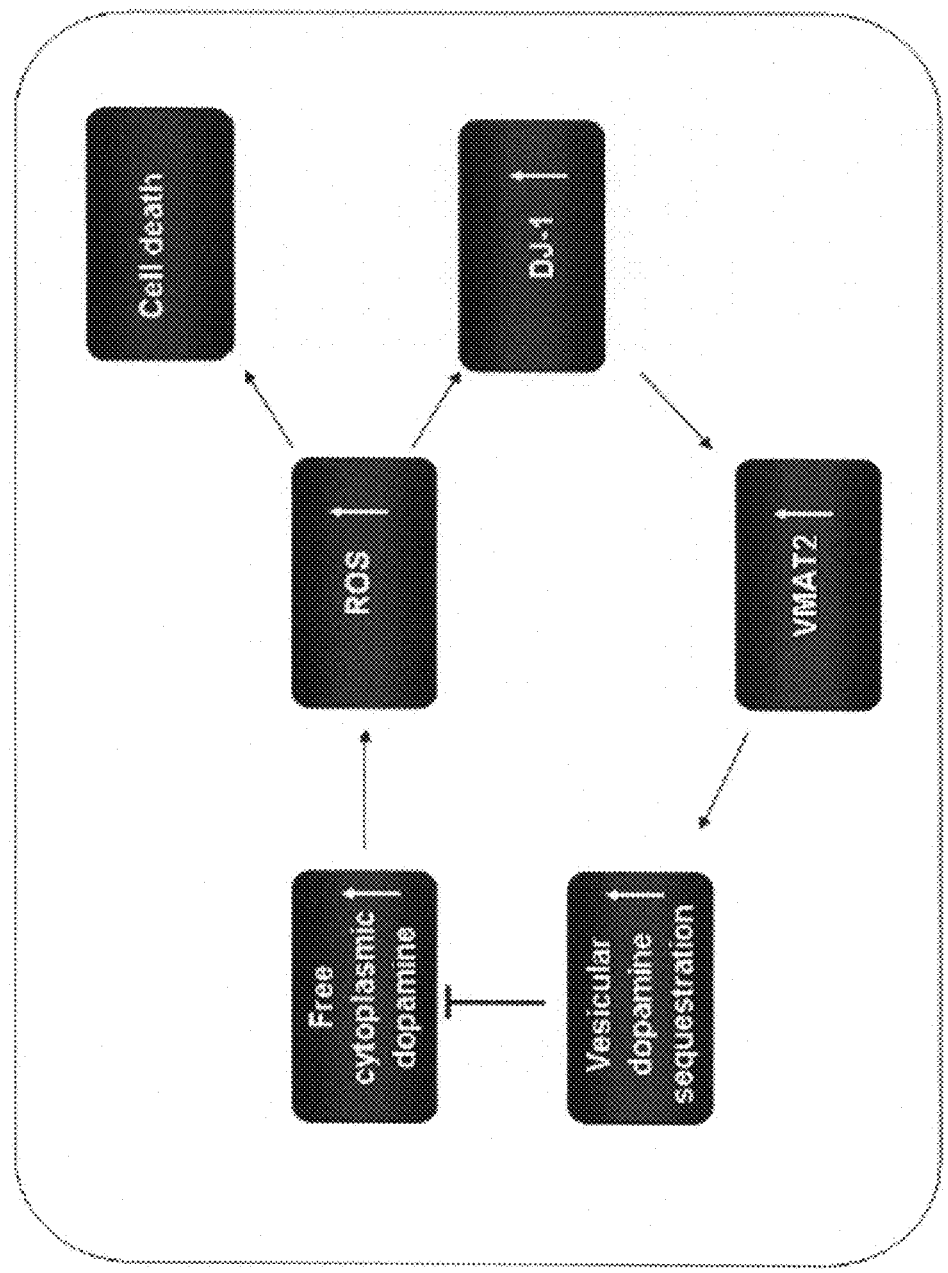

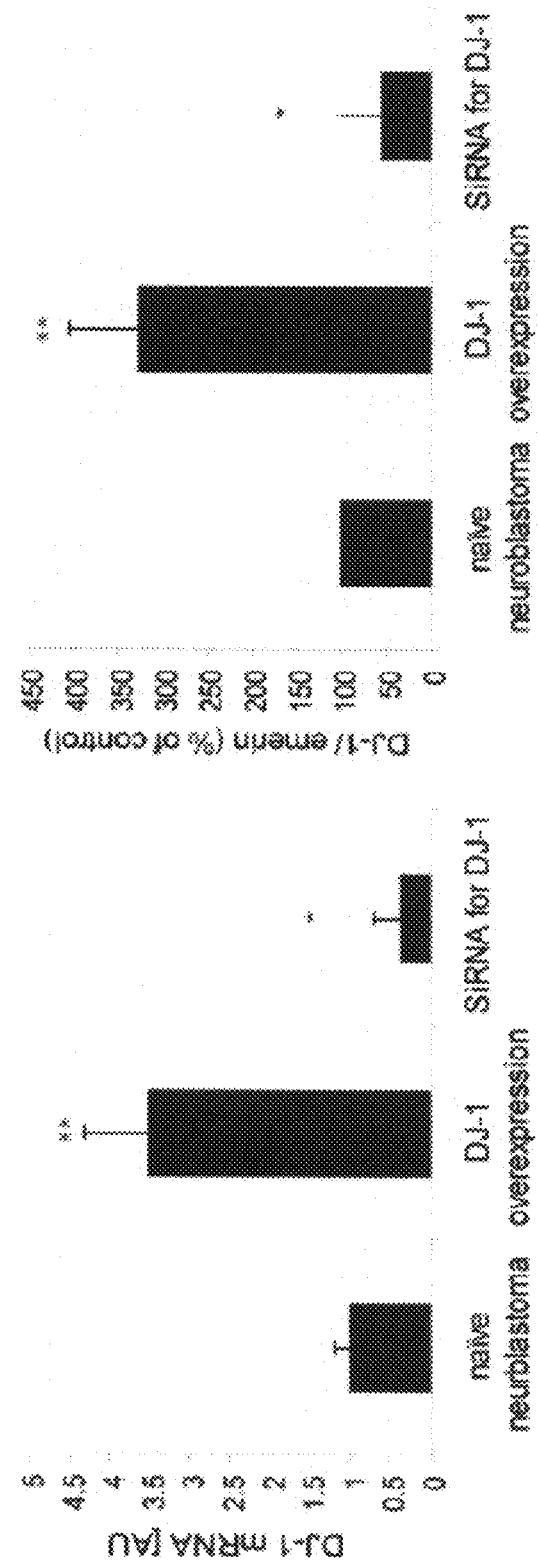

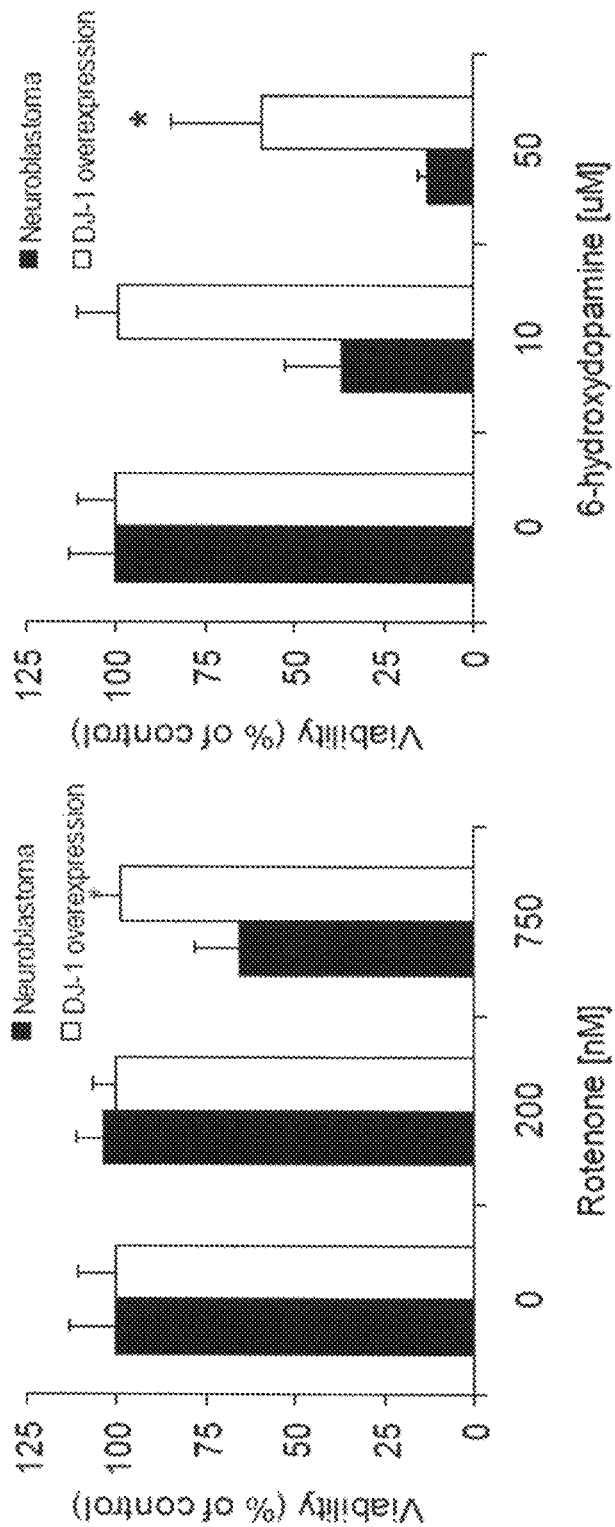

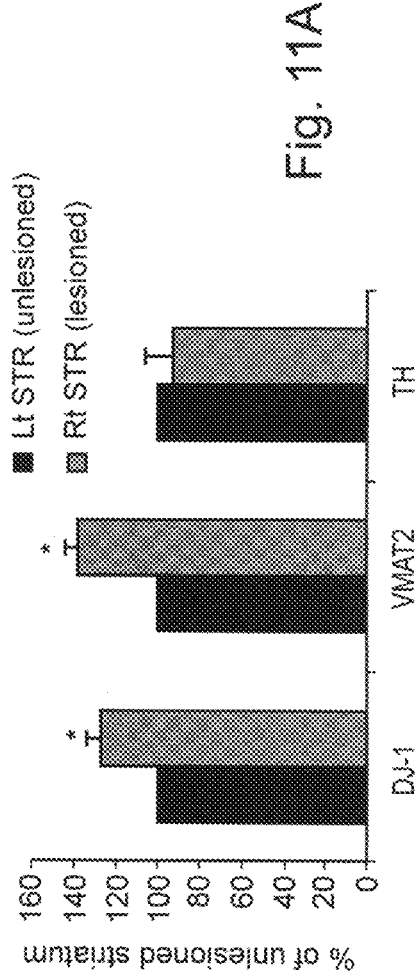
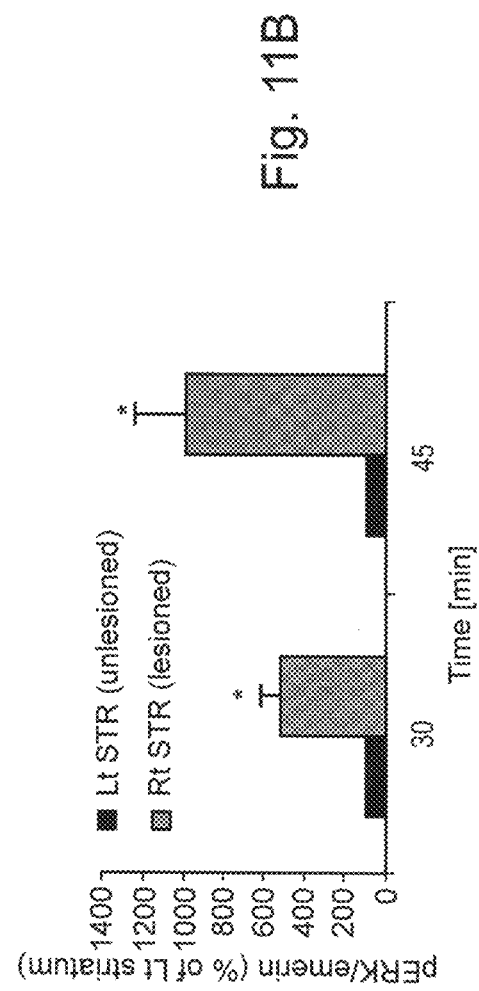
Fig. 11A
Fig. 11B

SEQUENCE LISTING

```
<160> NUMBER OF SEQ ID NOS: 528

<210> SEQ ID NO 1
<211> LENGTH: 21
<212> TYPE: PRT
<213> ORGANISM: Artificial sequence
<220> FEATURE:
<223> OTHER INFORMATION: DJ-1 derived peptide

<400> SEQUENCE: 1

Gly Ala Glu Glu Met Glu Thr Val Ile Pro Val Asp Val Met Arg Arg
1               5                   10                  15

Ala Gly Ile Lys Val
            20

<210> SEQ ID NO 2
<211> LENGTH: 12
<212> TYPE: PRT
<213> ORGANISM: Artificial sequence
<220> FEATURE:
<223> OTHER INFORMATION: DJ-1 derived peptide

<400> SEQUENCE: 2

Val Gln Cys Ser Arg Asp Val Val Ile Cys Pro Asp
1               5                   10

<210> SEQ ID NO 3
<211> LENGTH: 11
```

```
<212> TYPE: PRT
<213> ORGANISM: Artificial sequence
<220> FEATURE:
<223> OTHER INFORMATION: DJ-1 derived peptide

<400> SEQUENCE: 3

Val Val Val Leu Pro Gly Gly Asn Leu Gly Ala
1               5                   10

<210> SEQ ID NO 4
<211> LENGTH: 10
<212> TYPE: PRT
<213> ORGANISM: Artificial sequence
<220> FEATURE:
<223> OTHER INFORMATION: DJ-1 derived peptide

<400> SEQUENCE: 4

Ala Ala Ile Cys Ala Gly Pro Thr Ala Leu
1               5                   10

<210> SEQ ID NO 5
<211> LENGTH: 7
<212> TYPE: PRT
<213> ORGANISM: Artificial sequence
<220> FEATURE:
<223> OTHER INFORMATION: DJ-1 derived peptide

<400> SEQUENCE: 5

Thr Thr His Pro Leu Ala Lys
1               5

<210> SEQ ID NO 6
<211> LENGTH: 29
<212> TYPE: PRT
<213> ORGANISM: Artificial sequence
<220> FEATURE:
<223> OTHER INFORMATION: DJ-1 derived peptide

<400> SEQUENCE: 6

Val Glu Lys Asp Gly Leu Ile Leu Thr Ser Arg Gly Pro Gly Thr Ser
1               5                   10                  15

Phe Glu Phe Ala Leu Ala Ile Val Glu Ala Leu Asn Gly
            20                  25

<210> SEQ ID NO 7
<211> LENGTH: 19
<212> TYPE: DNA
<213> ORGANISM: Artificial sequence
<220> FEATURE:
<223> OTHER INFORMATION: Single strand DNA oligonucleotide

<400> SEQUENCE: 7
cgacagtcag ccgcatctt                                            19

<210> SEQ ID NO 8
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 8
ccaatacgac caaatccgtt g                                         21

<210> SEQ ID NO 9
<211> LENGTH: 20
<212> TYPE: DNA
```

```
<213> ORGANISM: Artificial sequence
<220> FEATURE:
<223> OTHER INFORMATION: Single strand DNA oligonucleotide

<400> SEQUENCE: 9
catgaggcga gctgggatta                                               20

<210> SEQ ID NO 10
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 10
gctggcatca ggacaaatga c                                             21

<210> SEQ ID NO 11
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 11
ggacaacatg ctgctcactg                                               20

<210> SEQ ID NO 12
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 12
attcccggtg accatagtcg                                               20

<210> SEQ ID NO 13
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 13
aggcgagggc taagatgttt                                               20

<210> SEQ ID NO 14
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 14
acgtggggtc ccagttactt                                               20

<210> SEQ ID NO 15
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 15
gagccttcct ggtgtttgtg                                               20
```

```
<210> SEQ ID NO 16
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 16
ctctccgatt ccagatggtg                                               20

<210> SEQ ID NO 17
<211> LENGTH: 4
<212> TYPE: PRT
<213> ORGANISM: Artificial sequence
<220> FEATURE:
<223> OTHER INFORMATION: DJ-1 derived peptide

<400> SEQUENCE: 17

Gly Ala Glu Glu
1

<210> SEQ ID NO 18
<211> LENGTH: 4
<212> TYPE: PRT
<213> ORGANISM: Artificial sequence
<220> FEATURE:
<223> OTHER INFORMATION: DJ-1 derived peptide

<400> SEQUENCE: 18

Ala Glu Glu Met
1

<210> SEQ ID NO 19
<211> LENGTH: 4
<212> TYPE: PRT
<213> ORGANISM: Artificial sequence
<220> FEATURE:
<223> OTHER INFORMATION: DJ-1 derived peptide

<400> SEQUENCE: 19

Glu Glu Met Glu
1

<210> SEQ ID NO 20
<211> LENGTH: 4
<212> TYPE: PRT
<213> ORGANISM: Artificial sequence
<220> FEATURE:
<223> OTHER INFORMATION: DJ-1 derived peptide

<400> SEQUENCE: 20

Glu Met Glu Thr
1

<210> SEQ ID NO 21
<211> LENGTH: 4
<212> TYPE: PRT
<213> ORGANISM: Artificial sequence
<220> FEATURE:
<223> OTHER INFORMATION: DJ-1 derived peptide

<400> SEQUENCE: 21

Met Glu Thr Val
1

<210> SEQ ID NO 22
<211> LENGTH: 4
```

```
<212> TYPE: PRT
<213> ORGANISM: Artificial sequence
<220> FEATURE:
<223> OTHER INFORMATION: DJ-1 derived peptide

<400> SEQUENCE: 22

Glu Thr Val Ile
1

<210> SEQ ID NO 23
<211> LENGTH: 4
<212> TYPE: PRT
<213> ORGANISM: Artificial sequence
<220> FEATURE:
<223> OTHER INFORMATION: DJ-1 derived peptide

<400> SEQUENCE: 23

Thr Val Ile Pro
1

<210> SEQ ID NO 24
<211> LENGTH: 4
<212> TYPE: PRT
<213> ORGANISM: Artificial sequence
<220> FEATURE:
<223> OTHER INFORMATION: DJ-1 derived peptide

<400> SEQUENCE: 24

Val Ile Pro Val
1

<210> SEQ ID NO 25
<211> LENGTH: 4
<212> TYPE: PRT
<213> ORGANISM: Artificial sequence
<220> FEATURE:
<223> OTHER INFORMATION: DJ-1 derived peptide

<400> SEQUENCE: 25

Ile Pro Val Asp
1

<210> SEQ ID NO 26
<211> LENGTH: 4
<212> TYPE: PRT
<213> ORGANISM: Artificial sequence
<220> FEATURE:
<223> OTHER INFORMATION: DJ-1 derived peptide

<400> SEQUENCE: 26

Pro Val Asp Val
1

<210> SEQ ID NO 27
<211> LENGTH: 4
<212> TYPE: PRT
<213> ORGANISM: Artificial sequence
<220> FEATURE:
<223> OTHER INFORMATION: DJ-1 derived peptide

<400> SEQUENCE: 27

Val Asp Val Met
1

<210> SEQ ID NO 28
<211> LENGTH: 4
<212> TYPE: PRT
<213> ORGANISM: Artificial sequence
```

```
<220> FEATURE:
<223> OTHER INFORMATION: DJ-1 derived peptide

<400> SEQUENCE: 28

Asp Val Met Arg
1

<210> SEQ ID NO 29
<211> LENGTH: 4
<212> TYPE: PRT
<213> ORGANISM: Artificial sequence
<220> FEATURE:
<223> OTHER INFORMATION: DJ-1 derived peptide

<400> SEQUENCE: 29

Val Met Arg Arg
1

<210> SEQ ID NO 30
<211> LENGTH: 4
<212> TYPE: PRT
<213> ORGANISM: Artificial sequence
<220> FEATURE:
<223> OTHER INFORMATION: DJ-1 derived peptide

<400> SEQUENCE: 30

Met Arg Arg Ala
1

<210> SEQ ID NO 31
<211> LENGTH: 4
<212> TYPE: PRT
<213> ORGANISM: Artificial sequence
<220> FEATURE:
<223> OTHER INFORMATION: DJ-1 derived peptide

<400> SEQUENCE: 31

Arg Arg Ala Gly
1

<210> SEQ ID NO 32
<211> LENGTH: 4
<212> TYPE: PRT
<213> ORGANISM: Artificial sequence
<220> FEATURE:
<223> OTHER INFORMATION: DJ-1 derived peptide

<400> SEQUENCE: 32

Arg Ala Gly Ile
1

<210> SEQ ID NO 33
<211> LENGTH: 4
<212> TYPE: PRT
<213> ORGANISM: Artificial sequence
<220> FEATURE:
<223> OTHER INFORMATION: DJ-1 derived peptide

<400> SEQUENCE: 33

Ala Gly Ile Lys
1

<210> SEQ ID NO 34
<211> LENGTH: 4
<212> TYPE: PRT
<213> ORGANISM: Artificial sequence
<220> FEATURE:
<223> OTHER INFORMATION: DJ-1 derived peptide
```

-continued

```
<400> SEQUENCE: 34

Gly Ile Lys Val
1

<210> SEQ ID NO 35
<211> LENGTH: 5
<212> TYPE: PRT
<213> ORGANISM: Artificial sequence
<220> FEATURE:
<223> OTHER INFORMATION: DJ-1 derived peptide

<400> SEQUENCE: 35

Gly Ala Glu Glu Met
1               5

<210> SEQ ID NO 36
<211> LENGTH: 5
<212> TYPE: PRT
<213> ORGANISM: Artificial sequence
<220> FEATURE:
<223> OTHER INFORMATION: DJ-1 derived peptide

<400> SEQUENCE: 36

Ala Glu Glu Met Glu
1               5

<210> SEQ ID NO 37
<211> LENGTH: 5
<212> TYPE: PRT
<213> ORGANISM: Artificial sequence
<220> FEATURE:
<223> OTHER INFORMATION: DJ-1 derived peptide

<400> SEQUENCE: 37

Glu Glu Met Glu Thr
1               5

<210> SEQ ID NO 38
<211> LENGTH: 5
<212> TYPE: PRT
<213> ORGANISM: Artificial sequence
<220> FEATURE:
<223> OTHER INFORMATION: DJ-1 derived peptide

<400> SEQUENCE: 38

Glu Met Glu Thr Val
1               5

<210> SEQ ID NO 39
<211> LENGTH: 5
<212> TYPE: PRT
<213> ORGANISM: Artificial sequence
<220> FEATURE:
<223> OTHER INFORMATION: DJ-1 derived peptide

<400> SEQUENCE: 39

Met Glu Thr Val Ile
1               5

<210> SEQ ID NO 40
<211> LENGTH: 5
<212> TYPE: PRT
<213> ORGANISM: Artificial sequence
<220> FEATURE:
<223> OTHER INFORMATION: DJ-1 derived peptide

<400> SEQUENCE: 40
```

```
Glu Thr Val Ile Pro
1               5

<210> SEQ ID NO 41
<211> LENGTH: 5
<212> TYPE: PRT
<213> ORGANISM: Artificial sequence
<220> FEATURE:
<223> OTHER INFORMATION: DJ-1 derived peptide

<400> SEQUENCE: 41

Thr Val Ile Pro Val
1               5

<210> SEQ ID NO 42
<211> LENGTH: 5
<212> TYPE: PRT
<213> ORGANISM: Artificial sequence
<220> FEATURE:
<223> OTHER INFORMATION: DJ-1 derived peptide

<400> SEQUENCE: 42

Val Ile Pro Val Asp
1               5

<210> SEQ ID NO 43
<211> LENGTH: 5
<212> TYPE: PRT
<213> ORGANISM: Artificial sequence
<220> FEATURE:
<223> OTHER INFORMATION: DJ-1 derived peptide

<400> SEQUENCE: 43

Ile Pro Val Asp Val
1               5

<210> SEQ ID NO 44
<211> LENGTH: 5
<212> TYPE: PRT
<213> ORGANISM: Artificial sequence
<220> FEATURE:
<223> OTHER INFORMATION: DJ-1 derived peptide

<400> SEQUENCE: 44

Pro Val Asp Val Met
1               5

<210> SEQ ID NO 45
<211> LENGTH: 5
<212> TYPE: PRT
<213> ORGANISM: Artificial sequence
<220> FEATURE:
<223> OTHER INFORMATION: DJ-1 derived peptide

<400> SEQUENCE: 45

Val Asp Val Met Arg
1               5

<210> SEQ ID NO 46
<211> LENGTH: 5
<212> TYPE: PRT
<213> ORGANISM: Artificial sequence
<220> FEATURE:
<223> OTHER INFORMATION: DJ-1 derived peptide

<400> SEQUENCE: 46

Asp Val Met Arg Arg
```

<210> SEQ ID NO 47
<211> LENGTH: 5
<212> TYPE: PRT
<213> ORGANISM: Artificial sequence
<220> FEATURE:
<223> OTHER INFORMATION: DJ-1 derived peptide

<400> SEQUENCE: 47

Val Met Arg Arg Ala
1               5

<210> SEQ ID NO 48
<211> LENGTH: 5
<212> TYPE: PRT
<213> ORGANISM: Artificial sequence
<220> FEATURE:
<223> OTHER INFORMATION: DJ-1 derived peptide

<400> SEQUENCE: 48

Met Arg Arg Ala Gly
1               5

<210> SEQ ID NO 49
<211> LENGTH: 5
<212> TYPE: PRT
<213> ORGANISM: Artificial sequence
<220> FEATURE:
<223> OTHER INFORMATION: DJ-1 derived peptide

<400> SEQUENCE: 49

Arg Arg Ala Gly Ile
1               5

<210> SEQ ID NO 50
<211> LENGTH: 5
<212> TYPE: PRT
<213> ORGANISM: Artificial sequence
<220> FEATURE:
<223> OTHER INFORMATION: DJ-1 derived peptide

<400> SEQUENCE: 50

Arg Ala Gly Ile Lys
1               5

<210> SEQ ID NO 51
<211> LENGTH: 5
<212> TYPE: PRT
<213> ORGANISM: Artificial sequence
<220> FEATURE:
<223> OTHER INFORMATION: DJ-1 derived peptide

<400> SEQUENCE: 51

Ala Gly Ile Lys Val
1               5

<210> SEQ ID NO 52
<211> LENGTH: 6
<212> TYPE: PRT
<213> ORGANISM: Artificial sequence
<220> FEATURE:
<223> OTHER INFORMATION: DJ-1 derived peptide

<400> SEQUENCE: 52

Gly Ala Glu Glu Met Glu
1               5

```
<210> SEQ ID NO 53
<211> LENGTH: 6
<212> TYPE: PRT
<213> ORGANISM: Artificial sequence
<220> FEATURE:
<223> OTHER INFORMATION: DJ-1 derived peptide

<400> SEQUENCE: 53

Ala Glu Glu Met Glu Thr
1               5

<210> SEQ ID NO 54
<211> LENGTH: 6
<212> TYPE: PRT
<213> ORGANISM: Artificial sequence
<220> FEATURE:
<223> OTHER INFORMATION: DJ-1 derived peptide

<400> SEQUENCE: 54

Glu Glu Met Glu Thr Val
1               5

<210> SEQ ID NO 55
<211> LENGTH: 6
<212> TYPE: PRT
<213> ORGANISM: Artificial sequence
<220> FEATURE:
<223> OTHER INFORMATION: DJ-1 derived peptide

<400> SEQUENCE: 55

Glu Met Glu Thr Val Ile
1               5

<210> SEQ ID NO 56
<211> LENGTH: 6
<212> TYPE: PRT
<213> ORGANISM: Artificial sequence
<220> FEATURE:
<223> OTHER INFORMATION: DJ-1 derived peptide

<400> SEQUENCE: 56

Met Glu Thr Val Ile Pro
1               5

<210> SEQ ID NO 57
<211> LENGTH: 6
<212> TYPE: PRT
<213> ORGANISM: Artificial sequence
<220> FEATURE:
<223> OTHER INFORMATION: DJ-1 derived peptide

<400> SEQUENCE: 57

Glu Thr Val Ile Pro Val
1               5

<210> SEQ ID NO 58
<211> LENGTH: 6
<212> TYPE: PRT
<213> ORGANISM: Artificial sequence
<220> FEATURE:
<223> OTHER INFORMATION: DJ-1 derived peptide

<400> SEQUENCE: 58

Thr Val Ile Pro Val Asp
1               5

<210> SEQ ID NO 59
```

```
<211> LENGTH: 6
<212> TYPE: PRT
<213> ORGANISM: Artificial sequence
<220> FEATURE:
<223> OTHER INFORMATION: DJ-1 derived peptide

<400> SEQUENCE: 59

Val Ile Pro Val Asp Val
1               5

<210> SEQ ID NO 60
<211> LENGTH: 6
<212> TYPE: PRT
<213> ORGANISM: Artificial sequence
<220> FEATURE:
<223> OTHER INFORMATION: DJ-1 derived peptide

<400> SEQUENCE: 60

Ile Pro Val Asp Val Met
1               5

<210> SEQ ID NO 61
<211> LENGTH: 6
<212> TYPE: PRT
<213> ORGANISM: Artificial sequence
<220> FEATURE:
<223> OTHER INFORMATION: DJ-1 derived peptide

<400> SEQUENCE: 61

Pro Val Asp Val Met Arg
1               5

<210> SEQ ID NO 62
<211> LENGTH: 6
<212> TYPE: PRT
<213> ORGANISM: Artificial sequence
<220> FEATURE:
<223> OTHER INFORMATION: DJ-1 derived peptide

<400> SEQUENCE: 62

Val Asp Val Met Arg Arg
1               5

<210> SEQ ID NO 63
<211> LENGTH: 6
<212> TYPE: PRT
<213> ORGANISM: Artificial sequence
<220> FEATURE:
<223> OTHER INFORMATION: DJ-1 derived peptide

<400> SEQUENCE: 63

Asp Val Met Arg Arg Ala
1               5

<210> SEQ ID NO 64
<211> LENGTH: 6
<212> TYPE: PRT
<213> ORGANISM: Artificial sequence
<220> FEATURE:
<223> OTHER INFORMATION: DJ-1 derived peptide

<400> SEQUENCE: 64

Val Met Arg Arg Ala Gly
1               5

<210> SEQ ID NO 65
<211> LENGTH: 6
<212> TYPE: PRT
```

<213> ORGANISM: Artificial sequence
<220> FEATURE:
<223> OTHER INFORMATION: DJ-1 derived peptide

<400> SEQUENCE: 65

Met Arg Arg Ala Gly Ile
1               5

<210> SEQ ID NO 66
<211> LENGTH: 6
<212> TYPE: PRT
<213> ORGANISM: Artificial sequence
<220> FEATURE:
<223> OTHER INFORMATION: DJ-1 derived peptide

<400> SEQUENCE: 66

Arg Arg Ala Gly Ile Lys
1               5

<210> SEQ ID NO 67
<211> LENGTH: 6
<212> TYPE: PRT
<213> ORGANISM: Artificial sequence
<220> FEATURE:
<223> OTHER INFORMATION: DJ-1 derived peptide

<400> SEQUENCE: 67

Arg Ala Gly Ile Lys Val
1               5

<210> SEQ ID NO 68
<211> LENGTH: 7
<212> TYPE: PRT
<213> ORGANISM: Artificial sequence
<220> FEATURE:
<223> OTHER INFORMATION: DJ-1 derived peptide

<400> SEQUENCE: 68

Gly Ala Glu Glu Met Glu Thr
1               5

<210> SEQ ID NO 69
<211> LENGTH: 7
<212> TYPE: PRT
<213> ORGANISM: Artificial sequence
<220> FEATURE:
<223> OTHER INFORMATION: DJ-1 derived peptide

<400> SEQUENCE: 69

Ala Glu Glu Met Glu Thr Val
1               5

<210> SEQ ID NO 70
<211> LENGTH: 7
<212> TYPE: PRT
<213> ORGANISM: Artificial sequence
<220> FEATURE:
<223> OTHER INFORMATION: DJ-1 derived peptide

<400> SEQUENCE: 70

Glu Glu Met Glu Thr Val Ile
1               5

<210> SEQ ID NO 71
<211> LENGTH: 7
<212> TYPE: PRT
<213> ORGANISM: Artificial sequence
<220> FEATURE:

-continued

<223> OTHER INFORMATION: DJ-1 derived peptide

<400> SEQUENCE: 71

Glu Met Glu Thr Val Ile Pro
1               5

<210> SEQ ID NO 72
<211> LENGTH: 7
<212> TYPE: PRT
<213> ORGANISM: Artificial sequence
<220> FEATURE:
<223> OTHER INFORMATION: DJ-1 derived peptide

<400> SEQUENCE: 72

Met Glu Thr Val Ile Pro Val
1               5

<210> SEQ ID NO 73
<211> LENGTH: 7
<212> TYPE: PRT
<213> ORGANISM: Artificial sequence
<220> FEATURE:
<223> OTHER INFORMATION: DJ-1 derived peptide

<400> SEQUENCE: 73

Glu Thr Val Ile Pro Val Asp
1               5

<210> SEQ ID NO 74
<211> LENGTH: 7
<212> TYPE: PRT
<213> ORGANISM: Artificial sequence
<220> FEATURE:
<223> OTHER INFORMATION: DJ-1 derived peptide

<400> SEQUENCE: 74

Thr Val Ile Pro Val Asp Val
1               5

<210> SEQ ID NO 75
<211> LENGTH: 7
<212> TYPE: PRT
<213> ORGANISM: Artificial sequence
<220> FEATURE:
<223> OTHER INFORMATION: DJ-1 derived peptide

<400> SEQUENCE: 75

Val Ile Pro Val Asp Val Met
1               5

<210> SEQ ID NO 76
<211> LENGTH: 7
<212> TYPE: PRT
<213> ORGANISM: Artificial sequence
<220> FEATURE:
<223> OTHER INFORMATION: DJ-1 derived peptide

<400> SEQUENCE: 76

Ile Pro Val Asp Val Met Arg
1               5

<210> SEQ ID NO 77
<211> LENGTH: 7
<212> TYPE: PRT
<213> ORGANISM: Artificial sequence
<220> FEATURE:
<223> OTHER INFORMATION: DJ-1 derived peptide

```
<400> SEQUENCE: 77

Pro Val Asp Val Met Arg Arg
1               5

<210> SEQ ID NO 78
<211> LENGTH: 7
<212> TYPE: PRT
<213> ORGANISM: Artificial sequence
<220> FEATURE:
<223> OTHER INFORMATION: DJ-1 derived peptide

<400> SEQUENCE: 78

Val Asp Val Met Arg Arg Ala
1               5

<210> SEQ ID NO 79
<211> LENGTH: 7
<212> TYPE: PRT
<213> ORGANISM: Artificial sequence
<220> FEATURE:
<223> OTHER INFORMATION: DJ-1 derived peptide

<400> SEQUENCE: 79

Asp Val Met Arg Arg Ala Gly
1               5

<210> SEQ ID NO 80
<211> LENGTH: 7
<212> TYPE: PRT
<213> ORGANISM: Artificial sequence
<220> FEATURE:
<223> OTHER INFORMATION: DJ-1 derived peptide

<400> SEQUENCE: 80

Val Met Arg Arg Ala Gly Ile
1               5

<210> SEQ ID NO 81
<211> LENGTH: 7
<212> TYPE: PRT
<213> ORGANISM: Artificial sequence
<220> FEATURE:
<223> OTHER INFORMATION: DJ-1 derived peptide

<400> SEQUENCE: 81

Met Arg Arg Ala Gly Ile Lys
1               5

<210> SEQ ID NO 82
<211> LENGTH: 7
<212> TYPE: PRT
<213> ORGANISM: Artificial sequence
<220> FEATURE:
<223> OTHER INFORMATION: DJ-1 derived peptide

<400> SEQUENCE: 82

Arg Arg Ala Gly Ile Lys Val
1               5

<210> SEQ ID NO 83
<211> LENGTH: 8
<212> TYPE: PRT
<213> ORGANISM: Artificial sequence
<220> FEATURE:
<223> OTHER INFORMATION: DJ-1 derived peptide

<400> SEQUENCE: 83
```

```
Gly Ala Glu Glu Met Glu Thr Val
1               5

<210> SEQ ID NO 84
<211> LENGTH: 8
<212> TYPE: PRT
<213> ORGANISM: Artificial sequence
<220> FEATURE:
<223> OTHER INFORMATION: DJ-1 derived peptide

<400> SEQUENCE: 84

Ala Glu Glu Met Glu Thr Val Ile
1               5

<210> SEQ ID NO 85
<211> LENGTH: 8
<212> TYPE: PRT
<213> ORGANISM: Artificial sequence
<220> FEATURE:
<223> OTHER INFORMATION: DJ-1 derived peptide

<400> SEQUENCE: 85

Glu Glu Met Glu Thr Val Ile Pro
1               5

<210> SEQ ID NO 86
<211> LENGTH: 8
<212> TYPE: PRT
<213> ORGANISM: Artificial sequence
<220> FEATURE:
<223> OTHER INFORMATION: DJ-1 derived peptide

<400> SEQUENCE: 86

Glu Met Glu Thr Val Ile Pro Val
1               5

<210> SEQ ID NO 87
<211> LENGTH: 8
<212> TYPE: PRT
<213> ORGANISM: Artificial sequence
<220> FEATURE:
<223> OTHER INFORMATION: DJ-1 derived peptide

<400> SEQUENCE: 87

Met Glu Thr Val Ile Pro Val Asp
1               5

<210> SEQ ID NO 88
<211> LENGTH: 8
<212> TYPE: PRT
<213> ORGANISM: Artificial sequence
<220> FEATURE:
<223> OTHER INFORMATION: DJ-1 derived peptide

<400> SEQUENCE: 88

Glu Thr Val Ile Pro Val Asp Val
1               5

<210> SEQ ID NO 89
<211> LENGTH: 8
<212> TYPE: PRT
<213> ORGANISM: Artificial sequence
<220> FEATURE:
<223> OTHER INFORMATION: DJ-1 derived peptide

<400> SEQUENCE: 89

Thr Val Ile Pro Val Asp Val Met
1               5
```

<210> SEQ ID NO 90
<211> LENGTH: 8
<212> TYPE: PRT
<213> ORGANISM: Artificial sequence
<220> FEATURE:
<223> OTHER INFORMATION: DJ-1 derived peptide

<400> SEQUENCE: 90

Val Ile Pro Val Asp Val Met Arg
1               5

<210> SEQ ID NO 91
<211> LENGTH: 8
<212> TYPE: PRT
<213> ORGANISM: Artificial sequence
<220> FEATURE:
<223> OTHER INFORMATION: DJ-1 derived peptide

<400> SEQUENCE: 91

Ile Pro Val Asp Val Met Arg Arg
1               5

<210> SEQ ID NO 92
<211> LENGTH: 8
<212> TYPE: PRT
<213> ORGANISM: Artificial sequence
<220> FEATURE:
<223> OTHER INFORMATION: DJ-1 derived peptide

<400> SEQUENCE: 92

Pro Val Asp Val Met Arg Arg Ala
1               5

<210> SEQ ID NO 93
<211> LENGTH: 8
<212> TYPE: PRT
<213> ORGANISM: Artificial sequence
<220> FEATURE:
<223> OTHER INFORMATION: DJ-1 derived peptide

<400> SEQUENCE: 93

Val Asp Val Met Arg Arg Ala Gly
1               5

<210> SEQ ID NO 94
<211> LENGTH: 8
<212> TYPE: PRT
<213> ORGANISM: Artificial sequence
<220> FEATURE:
<223> OTHER INFORMATION: DJ-1 derived peptide

<400> SEQUENCE: 94

Asp Val Met Arg Arg Ala Gly Ile
1               5

<210> SEQ ID NO 95
<211> LENGTH: 8
<212> TYPE: PRT
<213> ORGANISM: Artificial sequence
<220> FEATURE:
<223> OTHER INFORMATION: DJ-1 derived peptide

<400> SEQUENCE: 95

Val Met Arg Arg Ala Gly Ile Lys
1               5

```
<210> SEQ ID NO 96
<211> LENGTH: 8
<212> TYPE: PRT
<213> ORGANISM: Artificial sequence
<220> FEATURE:
<223> OTHER INFORMATION: DJ-1 derived peptide

<400> SEQUENCE: 96

Met Arg Arg Ala Gly Ile Lys Val
1               5

<210> SEQ ID NO 97
<211> LENGTH: 9
<212> TYPE: PRT
<213> ORGANISM: Artificial sequence
<220> FEATURE:
<223> OTHER INFORMATION: DJ-1 derived peptide

<400> SEQUENCE: 97

Gly Ala Glu Glu Met Glu Thr Val Ile
1               5

<210> SEQ ID NO 98
<211> LENGTH: 9
<212> TYPE: PRT
<213> ORGANISM: Artificial sequence
<220> FEATURE:
<223> OTHER INFORMATION: DJ-1 derived peptide

<400> SEQUENCE: 98

Ala Glu Glu Met Glu Thr Val Ile Pro
1               5

<210> SEQ ID NO 99
<211> LENGTH: 9
<212> TYPE: PRT
<213> ORGANISM: Artificial sequence
<220> FEATURE:
<223> OTHER INFORMATION: DJ-1 derived peptide

<400> SEQUENCE: 99

Glu Glu Met Glu Thr Val Ile Pro Val
1               5

<210> SEQ ID NO 100
<211> LENGTH: 9
<212> TYPE: PRT
<213> ORGANISM: Artificial sequence
<220> FEATURE:
<223> OTHER INFORMATION: DJ-1 derived peptide

<400> SEQUENCE: 100

Glu Met Glu Thr Val Ile Pro Val Asp
1               5

<210> SEQ ID NO 101
<211> LENGTH: 9
<212> TYPE: PRT
<213> ORGANISM: Artificial sequence
<220> FEATURE:
<223> OTHER INFORMATION: DJ-1 derived peptide

<400> SEQUENCE: 101

Met Glu Thr Val Ile Pro Val Asp Val
1               5

<210> SEQ ID NO 102
<211> LENGTH: 9
```

```
<212> TYPE: PRT
<213> ORGANISM: Artificial sequence
<220> FEATURE:
<223> OTHER INFORMATION: DJ-1 derived peptide

<400> SEQUENCE: 102

Glu Thr Val Ile Pro Val Asp Val Met
1               5

<210> SEQ ID NO 103
<211> LENGTH: 9
<212> TYPE: PRT
<213> ORGANISM: Artificial sequence
<220> FEATURE:
<223> OTHER INFORMATION: DJ-1 derived peptide

<400> SEQUENCE: 103

Thr Val Ile Pro Val Asp Val Met Arg
1               5

<210> SEQ ID NO 104
<211> LENGTH: 9
<212> TYPE: PRT
<213> ORGANISM: Artificial sequence
<220> FEATURE:
<223> OTHER INFORMATION: DJ-1 derived peptide

<400> SEQUENCE: 104

Val Ile Pro Val Asp Val Met Arg Arg
1               5

<210> SEQ ID NO 105
<211> LENGTH: 9
<212> TYPE: PRT
<213> ORGANISM: Artificial sequence
<220> FEATURE:
<223> OTHER INFORMATION: DJ-1 derived peptide

<400> SEQUENCE: 105

Ile Pro Val Asp Val Met Arg Arg Ala
1               5

<210> SEQ ID NO 106
<211> LENGTH: 9
<212> TYPE: PRT
<213> ORGANISM: Artificial sequence
<220> FEATURE:
<223> OTHER INFORMATION: DJ-1 derived peptide

<400> SEQUENCE: 106

Pro Val Asp Val Met Arg Arg Ala Gly
1               5

<210> SEQ ID NO 107
<211> LENGTH: 9
<212> TYPE: PRT
<213> ORGANISM: Artificial sequence
<220> FEATURE:
<223> OTHER INFORMATION: DJ-1 derived peptide

<400> SEQUENCE: 107

Val Asp Val Met Arg Arg Ala Gly Ile
1               5

<210> SEQ ID NO 108
<211> LENGTH: 9
<212> TYPE: PRT
<213> ORGANISM: Artificial sequence
```

```
<220> FEATURE:
<223> OTHER INFORMATION: DJ-1 derived peptide

<400> SEQUENCE: 108

Asp Val Met Arg Arg Ala Gly Ile Lys
1               5

<210> SEQ ID NO 109
<211> LENGTH: 9
<212> TYPE: PRT
<213> ORGANISM: Artificial sequence
<220> FEATURE:
<223> OTHER INFORMATION: DJ-1 derived peptide

<400> SEQUENCE: 109

Val Met Arg Arg Ala Gly Ile Lys Val
1               5

<210> SEQ ID NO 110
<211> LENGTH: 10
<212> TYPE: PRT
<213> ORGANISM: Artificial sequence
<220> FEATURE:
<223> OTHER INFORMATION: DJ-1 derived peptide

<400> SEQUENCE: 110

Gly Ala Glu Glu Met Glu Thr Val Ile Pro
1               5                   10

<210> SEQ ID NO 111
<211> LENGTH: 10
<212> TYPE: PRT
<213> ORGANISM: Artificial sequence
<220> FEATURE:
<223> OTHER INFORMATION: DJ-1 derived peptide

<400> SEQUENCE: 111

Ala Glu Glu Met Glu Thr Val Ile Pro Val
1               5                   10

<210> SEQ ID NO 112
<211> LENGTH: 10
<212> TYPE: PRT
<213> ORGANISM: Artificial sequence
<220> FEATURE:
<223> OTHER INFORMATION: DJ-1 derived peptide

<400> SEQUENCE: 112

Glu Glu Met Glu Thr Val Ile Pro Val Asp
1               5                   10

<210> SEQ ID NO 113
<211> LENGTH: 10
<212> TYPE: PRT
<213> ORGANISM: Artificial sequence
<220> FEATURE:
<223> OTHER INFORMATION: DJ-1 derived peptide

<400> SEQUENCE: 113

Glu Met Glu Thr Val Ile Pro Val Asp Val
1               5                   10

<210> SEQ ID NO 114
<211> LENGTH: 10
<212> TYPE: PRT
<213> ORGANISM: Artificial sequence
<220> FEATURE:
<223> OTHER INFORMATION: DJ-1 derived peptide
```

```
<400> SEQUENCE: 114

Met Glu Thr Val Ile Pro Val Asp Val Met
1               5                   10

<210> SEQ ID NO 115
<211> LENGTH: 10
<212> TYPE: PRT
<213> ORGANISM: Artificial sequence
<220> FEATURE:
<223> OTHER INFORMATION: DJ-1 derived peptide

<400> SEQUENCE: 115

Glu Thr Val Ile Pro Val Asp Val Met Arg
1               5                   10

<210> SEQ ID NO 116
<211> LENGTH: 10
<212> TYPE: PRT
<213> ORGANISM: Artificial sequence
<220> FEATURE:
<223> OTHER INFORMATION: DJ-1 derived peptide

<400> SEQUENCE: 116

Thr Val Ile Pro Val Asp Val Met Arg Arg
1               5                   10

<210> SEQ ID NO 117
<211> LENGTH: 10
<212> TYPE: PRT
<213> ORGANISM: Artificial sequence
<220> FEATURE:
<223> OTHER INFORMATION: DJ-1 derived peptide

<400> SEQUENCE: 117

Val Ile Pro Val Asp Val Met Arg Arg Ala
1               5                   10

<210> SEQ ID NO 118
<211> LENGTH: 10
<212> TYPE: PRT
<213> ORGANISM: Artificial sequence
<220> FEATURE:
<223> OTHER INFORMATION: DJ-1 derived peptide

<400> SEQUENCE: 118

Ile Pro Val Asp Val Met Arg Arg Ala Gly
1               5                   10

<210> SEQ ID NO 119
<211> LENGTH: 10
<212> TYPE: PRT
<213> ORGANISM: Artificial sequence
<220> FEATURE:
<223> OTHER INFORMATION: DJ-1 derived peptide

<400> SEQUENCE: 119

Pro Val Asp Val Met Arg Arg Ala Gly Ile
1               5                   10

<210> SEQ ID NO 120
<211> LENGTH: 10
<212> TYPE: PRT
<213> ORGANISM: Artificial sequence
<220> FEATURE:
<223> OTHER INFORMATION: DJ-1 derived peptide

<400> SEQUENCE: 120
```

Val Asp Val Met Arg Arg Ala Gly Ile Lys
1               5                   10

<210> SEQ ID NO 121
<211> LENGTH: 10
<212> TYPE: PRT
<213> ORGANISM: Artificial sequence
<220> FEATURE:
<223> OTHER INFORMATION: DJ-1 derived peptide

<400> SEQUENCE: 121

Asp Val Met Arg Arg Ala Gly Ile Lys Val
1               5                   10

<210> SEQ ID NO 122
<211> LENGTH: 11
<212> TYPE: PRT
<213> ORGANISM: Artificial sequence
<220> FEATURE:
<223> OTHER INFORMATION: DJ-1 derived peptide

<400> SEQUENCE: 122

Gly Ala Glu Glu Met Glu Thr Val Ile Pro Val
1               5                   10

<210> SEQ ID NO 123
<211> LENGTH: 11
<212> TYPE: PRT
<213> ORGANISM: Artificial sequence
<220> FEATURE:
<223> OTHER INFORMATION: DJ-1 derived peptide

<400> SEQUENCE: 123

Ala Glu Glu Met Glu Thr Val Ile Pro Val Asp
1               5                   10

<210> SEQ ID NO 124
<211> LENGTH: 11
<212> TYPE: PRT
<213> ORGANISM: Artificial sequence
<220> FEATURE:
<223> OTHER INFORMATION: DJ-1 derived peptide

<400> SEQUENCE: 124

Glu Glu Met Glu Thr Val Ile Pro Val Asp Val
1               5                   10

<210> SEQ ID NO 125
<211> LENGTH: 11
<212> TYPE: PRT
<213> ORGANISM: Artificial sequence
<220> FEATURE:
<223> OTHER INFORMATION: DJ-1 derived peptide

<400> SEQUENCE: 125

Glu Met Glu Thr Val Ile Pro Val Asp Val Met
1               5                   10

<210> SEQ ID NO 126
<211> LENGTH: 11
<212> TYPE: PRT
<213> ORGANISM: Artificial sequence
<220> FEATURE:
<223> OTHER INFORMATION: DJ-1 derived peptide

<400> SEQUENCE: 126

Met Glu Thr Val Ile Pro Val Asp Val Met Arg

```
1               5                   10
```

<210> SEQ ID NO 127
<211> LENGTH: 11
<212> TYPE: PRT
<213> ORGANISM: Artificial sequence
<220> FEATURE:
<223> OTHER INFORMATION: DJ-1 derived peptide

<400> SEQUENCE: 127

```
Glu Thr Val Ile Pro Val Asp Val Met Arg Arg
1               5                   10
```

<210> SEQ ID NO 128
<211> LENGTH: 11
<212> TYPE: PRT
<213> ORGANISM: Artificial sequence
<220> FEATURE:
<223> OTHER INFORMATION: DJ-1 derived peptide

<400> SEQUENCE: 128

```
Thr Val Ile Pro Val Asp Val Met Arg Arg Ala
1               5                   10
```

<210> SEQ ID NO 129
<211> LENGTH: 11
<212> TYPE: PRT
<213> ORGANISM: Artificial sequence
<220> FEATURE:
<223> OTHER INFORMATION: DJ-1 derived peptide

<400> SEQUENCE: 129

```
Val Ile Pro Val Asp Val Met Arg Arg Ala Gly
1               5                   10
```

<210> SEQ ID NO 130
<211> LENGTH: 11
<212> TYPE: PRT
<213> ORGANISM: Artificial sequence
<220> FEATURE:
<223> OTHER INFORMATION: DJ-1 derived peptide

<400> SEQUENCE: 130

```
Ile Pro Val Asp Val Met Arg Arg Ala Gly Ile
1               5                   10
```

<210> SEQ ID NO 131
<211> LENGTH: 11
<212> TYPE: PRT
<213> ORGANISM: Artificial sequence
<220> FEATURE:
<223> OTHER INFORMATION: DJ-1 derived peptide

<400> SEQUENCE: 131

```
Pro Val Asp Val Met Arg Arg Ala Gly Ile Lys
1               5                   10
```

<210> SEQ ID NO 132
<211> LENGTH: 11
<212> TYPE: PRT
<213> ORGANISM: Artificial sequence
<220> FEATURE:
<223> OTHER INFORMATION: DJ-1 derived peptide

<400> SEQUENCE: 132

```
Val Asp Val Met Arg Arg Ala Gly Ile Lys Val
1               5                   10
```

```
<210> SEQ ID NO 133
<211> LENGTH: 12
<212> TYPE: PRT
<213> ORGANISM: Artificial sequence
<220> FEATURE:
<223> OTHER INFORMATION: DJ-1 derived peptide

<400> SEQUENCE: 133

Gly Ala Glu Glu Met Glu Thr Val Ile Pro Val Asp
1               5                   10

<210> SEQ ID NO 134
<211> LENGTH: 12
<212> TYPE: PRT
<213> ORGANISM: Artificial sequence
<220> FEATURE:
<223> OTHER INFORMATION: DJ-1 derived peptide

<400> SEQUENCE: 134

Ala Glu Glu Met Glu Thr Val Ile Pro Val Asp Val
1               5                   10

<210> SEQ ID NO 135
<211> LENGTH: 12
<212> TYPE: PRT
<213> ORGANISM: Artificial sequence
<220> FEATURE:
<223> OTHER INFORMATION: DJ-1 derived peptide

<400> SEQUENCE: 135

Glu Glu Met Glu Thr Val Ile Pro Val Asp Val Met
1               5                   10

<210> SEQ ID NO 136
<211> LENGTH: 12
<212> TYPE: PRT
<213> ORGANISM: Artificial sequence
<220> FEATURE:
<223> OTHER INFORMATION: DJ-1 derived peptide

<400> SEQUENCE: 136

Glu Met Glu Thr Val Ile Pro Val Asp Val Met Arg
1               5                   10

<210> SEQ ID NO 137
<211> LENGTH: 12
<212> TYPE: PRT
<213> ORGANISM: Artificial sequence
<220> FEATURE:
<223> OTHER INFORMATION: DJ-1 derived peptide

<400> SEQUENCE: 137

Met Glu Thr Val Ile Pro Val Asp Val Met Arg Arg
1               5                   10

<210> SEQ ID NO 138
<211> LENGTH: 12
<212> TYPE: PRT
<213> ORGANISM: Artificial sequence
<220> FEATURE:
<223> OTHER INFORMATION: DJ-1 derived peptide

<400> SEQUENCE: 138

Glu Thr Val Ile Pro Val Asp Val Met Arg Arg Ala
1               5                   10

<210> SEQ ID NO 139
```

```
<211> LENGTH: 12
<212> TYPE: PRT
<213> ORGANISM: Artificial sequence
<220> FEATURE:
<223> OTHER INFORMATION: DJ-1 derived peptide

<400> SEQUENCE: 139

Thr Val Ile Pro Val Asp Val Met Arg Arg Ala Gly
1               5                   10

<210> SEQ ID NO 140
<211> LENGTH: 12
<212> TYPE: PRT
<213> ORGANISM: Artificial sequence
<220> FEATURE:
<223> OTHER INFORMATION: DJ-1 derived peptide

<400> SEQUENCE: 140

Val Ile Pro Val Asp Val Met Arg Arg Ala Gly Ile
1               5                   10

<210> SEQ ID NO 141
<211> LENGTH: 12
<212> TYPE: PRT
<213> ORGANISM: Artificial sequence
<220> FEATURE:
<223> OTHER INFORMATION: DJ-1 derived peptide

<400> SEQUENCE: 141

Ile Pro Val Asp Val Met Arg Arg Ala Gly Ile Lys
1               5                   10

<210> SEQ ID NO 142
<211> LENGTH: 12
<212> TYPE: PRT
<213> ORGANISM: Artificial sequence
<220> FEATURE:
<223> OTHER INFORMATION: DJ-1 derived peptide

<400> SEQUENCE: 142

Pro Val Asp Val Met Arg Arg Ala Gly Ile Lys Val
1               5                   10

<210> SEQ ID NO 143
<211> LENGTH: 13
<212> TYPE: PRT
<213> ORGANISM: Artificial sequence
<220> FEATURE:
<223> OTHER INFORMATION: DJ-1 derived peptide

<400> SEQUENCE: 143

Gly Ala Glu Glu Met Glu Thr Val Ile Pro Val Asp Val
1               5                   10

<210> SEQ ID NO 144
<211> LENGTH: 13
<212> TYPE: PRT
<213> ORGANISM: Artificial sequence
<220> FEATURE:
<223> OTHER INFORMATION: DJ-1 derived peptide

<400> SEQUENCE: 144

Ala Glu Glu Met Glu Thr Val Ile Pro Val Asp Val Met
1               5                   10

<210> SEQ ID NO 145
<211> LENGTH: 13
<212> TYPE: PRT
```

<213> ORGANISM: Artificial sequence
<220> FEATURE:
<223> OTHER INFORMATION: DJ-1 derived peptide

<400> SEQUENCE: 145

Glu Glu Met Glu Thr Val Ile Pro Val Asp Val Met Arg
1               5                   10

<210> SEQ ID NO 146
<211> LENGTH: 13
<212> TYPE: PRT
<213> ORGANISM: Artificial sequence
<220> FEATURE:
<223> OTHER INFORMATION: DJ-1 derived peptide

<400> SEQUENCE: 146

Glu Met Glu Thr Val Ile Pro Val Asp Val Met Arg Arg
1               5                   10

<210> SEQ ID NO 147
<211> LENGTH: 13
<212> TYPE: PRT
<213> ORGANISM: Artificial sequence
<220> FEATURE:
<223> OTHER INFORMATION: DJ-1 derived peptide

<400> SEQUENCE: 147

Met Glu Thr Val Ile Pro Val Asp Val Met Arg Arg Ala
1               5                   10

<210> SEQ ID NO 148
<211> LENGTH: 13
<212> TYPE: PRT
<213> ORGANISM: Artificial sequence
<220> FEATURE:
<223> OTHER INFORMATION: DJ-1 derived peptide

<400> SEQUENCE: 148

Glu Thr Val Ile Pro Val Asp Val Met Arg Arg Ala Gly
1               5                   10

<210> SEQ ID NO 149
<211> LENGTH: 13
<212> TYPE: PRT
<213> ORGANISM: Artificial sequence
<220> FEATURE:
<223> OTHER INFORMATION: DJ-1 derived peptide

<400> SEQUENCE: 149

Thr Val Ile Pro Val Asp Val Met Arg Arg Ala Gly Ile
1               5                   10

<210> SEQ ID NO 150
<211> LENGTH: 13
<212> TYPE: PRT
<213> ORGANISM: Artificial sequence
<220> FEATURE:
<223> OTHER INFORMATION: DJ-1 derived peptide

<400> SEQUENCE: 150

Val Ile Pro Val Asp Val Met Arg Arg Ala Gly Ile Lys
1               5                   10

<210> SEQ ID NO 151
<211> LENGTH: 13
<212> TYPE: PRT
<213> ORGANISM: Artificial sequence
<220> FEATURE:

<223> OTHER INFORMATION: DJ-1 derived peptide

<400> SEQUENCE: 151

Ile Pro Val Asp Val Met Arg Arg Ala Gly Ile Lys Val
1               5                   10

<210> SEQ ID NO 152
<211> LENGTH: 14
<212> TYPE: PRT
<213> ORGANISM: Artificial sequence
<220> FEATURE:
<223> OTHER INFORMATION: DJ-1 derived peptide

<400> SEQUENCE: 152

Gly Ala Glu Glu Met Glu Thr Val Ile Pro Val Asp Val Met
1               5                   10

<210> SEQ ID NO 153
<211> LENGTH: 14
<212> TYPE: PRT
<213> ORGANISM: Artificial sequence
<220> FEATURE:
<223> OTHER INFORMATION: DJ-1 derived peptide

<400> SEQUENCE: 153

Ala Glu Glu Met Glu Thr Val Ile Pro Val Asp Val Met Arg
1               5                   10

<210> SEQ ID NO 154
<211> LENGTH: 14
<212> TYPE: PRT
<213> ORGANISM: Artificial sequence
<220> FEATURE:
<223> OTHER INFORMATION: DJ-1 derived peptide

<400> SEQUENCE: 154

Glu Glu Met Glu Thr Val Ile Pro Val Asp Val Met Arg Arg
1               5                   10

<210> SEQ ID NO 155
<211> LENGTH: 14
<212> TYPE: PRT
<213> ORGANISM: Artificial sequence
<220> FEATURE:
<223> OTHER INFORMATION: DJ-1 derived peptide

<400> SEQUENCE: 155

Glu Met Glu Thr Val Ile Pro Val Asp Val Met Arg Arg Ala
1               5                   10

<210> SEQ ID NO 156
<211> LENGTH: 14
<212> TYPE: PRT
<213> ORGANISM: Artificial sequence
<220> FEATURE:
<223> OTHER INFORMATION: DJ-1 derived peptide

<400> SEQUENCE: 156

Met Glu Thr Val Ile Pro Val Asp Val Met Arg Arg Ala Gly
1               5                   10

<210> SEQ ID NO 157
<211> LENGTH: 14
<212> TYPE: PRT
<213> ORGANISM: Artificial sequence
<220> FEATURE:
<223> OTHER INFORMATION: DJ-1 derived peptide -continued

```
<400> SEQUENCE: 157

Glu Thr Val Ile Pro Val Asp Val Met Arg Arg Ala Gly Ile
1               5                   10

<210> SEQ ID NO 158
<211> LENGTH: 14
<212> TYPE: PRT
<213> ORGANISM: Artificial sequence
<220> FEATURE:
<223> OTHER INFORMATION: DJ-1 derived peptide

<400> SEQUENCE: 158

Thr Val Ile Pro Val Asp Val Met Arg Arg Ala Gly Ile Lys
1               5                   10

<210> SEQ ID NO 159
<211> LENGTH: 14
<212> TYPE: PRT
<213> ORGANISM: Artificial sequence
<220> FEATURE:
<223> OTHER INFORMATION: DJ-1 derived peptide

<400> SEQUENCE: 159

Val Ile Pro Val Asp Val Met Arg Arg Ala Gly Ile Lys Val
1               5                   10

<210> SEQ ID NO 160
<211> LENGTH: 15
<212> TYPE: PRT
<213> ORGANISM: Artificial sequence
<220> FEATURE:
<223> OTHER INFORMATION: DJ-1 derived peptide

<400> SEQUENCE: 160

Gly Ala Glu Glu Met Glu Thr Val Ile Pro Val Asp Val Met Arg
1               5                   10                  15

<210> SEQ ID NO 161
<211> LENGTH: 15
<212> TYPE: PRT
<213> ORGANISM: Artificial sequence
<220> FEATURE:
<223> OTHER INFORMATION: DJ-1 derived peptide

<400> SEQUENCE: 161

Ala Glu Glu Met Glu Thr Val Ile Pro Val Asp Val Met Arg Arg
1               5                   10                  15

<210> SEQ ID NO 162
<211> LENGTH: 15
<212> TYPE: PRT
<213> ORGANISM: Artificial sequence
<220> FEATURE:
<223> OTHER INFORMATION: DJ-1 derived peptide

<400> SEQUENCE: 162

Glu Glu Met Glu Thr Val Ile Pro Val Asp Val Met Arg Arg Ala
1               5                   10                  15

<210> SEQ ID NO 163
<211> LENGTH: 15
<212> TYPE: PRT
<213> ORGANISM: Artificial sequence
<220> FEATURE:
<223> OTHER INFORMATION: DJ-1 derived peptide

<400> SEQUENCE: 163
```

```
Glu Met Glu Thr Val Ile Pro Val Asp Val Met Arg Arg Ala Gly
1               5                   10                  15
```

<210> SEQ ID NO 164
<211> LENGTH: 15
<212> TYPE: PRT
<213> ORGANISM: Artificial sequence
<220> FEATURE:
<223> OTHER INFORMATION: DJ-1 derived peptide

<400> SEQUENCE: 164

```
Met Glu Thr Val Ile Pro Val Asp Val Met Arg Arg Ala Gly Ile
1               5                   10                  15
```

<210> SEQ ID NO 165
<211> LENGTH: 15
<212> TYPE: PRT
<213> ORGANISM: Artificial sequence
<220> FEATURE:
<223> OTHER INFORMATION: DJ-1 derived peptide

<400> SEQUENCE: 165

```
Glu Thr Val Ile Pro Val Asp Val Met Arg Arg Ala Gly Ile Lys
1               5                   10                  15
```

<210> SEQ ID NO 166
<211> LENGTH: 15
<212> TYPE: PRT
<213> ORGANISM: Artificial sequence
<220> FEATURE:
<223> OTHER INFORMATION: DJ-1 derived peptide

<400> SEQUENCE: 166

```
Thr Val Ile Pro Val Asp Val Met Arg Arg Ala Gly Ile Lys Val
1               5                   10                  15
```

<210> SEQ ID NO 167
<211> LENGTH: 4
<212> TYPE: PRT
<213> ORGANISM: Artificial sequence
<220> FEATURE:
<223> OTHER INFORMATION: DJ-1 derived peptide

<400> SEQUENCE: 167

```
Val Gln Cys Ser
1
```

<210> SEQ ID NO 168
<211> LENGTH: 4
<212> TYPE: PRT
<213> ORGANISM: Artificial sequence
<220> FEATURE:
<223> OTHER INFORMATION: DJ-1 derived peptide

<400> SEQUENCE: 168

```
Gln Cys Ser Arg
1
```

<210> SEQ ID NO 169
<211> LENGTH: 4
<212> TYPE: PRT
<213> ORGANISM: Artificial sequence
<220> FEATURE:
<223> OTHER INFORMATION: DJ-1 derived peptide

<400> SEQUENCE: 169

```
Cys Ser Arg Asp
1
```

```
<210> SEQ ID NO 170
<211> LENGTH: 4
<212> TYPE: PRT
<213> ORGANISM: Artificial sequence
<220> FEATURE:
<223> OTHER INFORMATION: DJ-1 derived peptide

<400> SEQUENCE: 170

Ser Arg Asp Val
1

<210> SEQ ID NO 171
<211> LENGTH: 4
<212> TYPE: PRT
<213> ORGANISM: Artificial sequence
<220> FEATURE:
<223> OTHER INFORMATION: DJ-1 derived peptide

<400> SEQUENCE: 171

Arg Asp Val Val
1

<210> SEQ ID NO 172
<211> LENGTH: 4
<212> TYPE: PRT
<213> ORGANISM: Artificial sequence
<220> FEATURE:
<223> OTHER INFORMATION: DJ-1 derived peptide

<400> SEQUENCE: 172

Asp Val Val Ile
1

<210> SEQ ID NO 173
<211> LENGTH: 4
<212> TYPE: PRT
<213> ORGANISM: Artificial sequence
<220> FEATURE:
<223> OTHER INFORMATION: DJ-1 derived peptide

<400> SEQUENCE: 173

Val Val Ile Cys
1

<210> SEQ ID NO 174
<211> LENGTH: 4
<212> TYPE: PRT
<213> ORGANISM: Artificial sequence
<220> FEATURE:
<223> OTHER INFORMATION: DJ-1 derived peptide

<400> SEQUENCE: 174

Val Ile Cys Pro
1

<210> SEQ ID NO 175
<211> LENGTH: 4
<212> TYPE: PRT
<213> ORGANISM: Artificial sequence
<220> FEATURE:
<223> OTHER INFORMATION: DJ-1 derived peptide

<400> SEQUENCE: 175

Ile Cys Pro Asp
1
```

-continued

```
<210> SEQ ID NO 176
<211> LENGTH: 5
<212> TYPE: PRT
<213> ORGANISM: Artificial sequence
<220> FEATURE:
<223> OTHER INFORMATION: DJ-1 derived peptide

<400> SEQUENCE: 176

Val Gln Cys Ser Arg
1               5

<210> SEQ ID NO 177
<211> LENGTH: 5
<212> TYPE: PRT
<213> ORGANISM: Artificial sequence
<220> FEATURE:
<223> OTHER INFORMATION: DJ-1 derived peptide

<400> SEQUENCE: 177

Gln Cys Ser Arg Asp
1               5

<210> SEQ ID NO 178
<211> LENGTH: 5
<212> TYPE: PRT
<213> ORGANISM: Artificial sequence
<220> FEATURE:
<223> OTHER INFORMATION: DJ-1 derived peptide

<400> SEQUENCE: 178

Cys Ser Arg Asp Val
1               5

<210> SEQ ID NO 179
<211> LENGTH: 5
<212> TYPE: PRT
<213> ORGANISM: Artificial sequence
<220> FEATURE:
<223> OTHER INFORMATION: DJ-1 derived peptide

<400> SEQUENCE: 179

Ser Arg Asp Val Val
1               5

<210> SEQ ID NO 180
<211> LENGTH: 5
<212> TYPE: PRT
<213> ORGANISM: Artificial sequence
<220> FEATURE:
<223> OTHER INFORMATION: DJ-1 derived peptide

<400> SEQUENCE: 180

Arg Asp Val Val Ile
1               5

<210> SEQ ID NO 181
<211> LENGTH: 5
<212> TYPE: PRT
<213> ORGANISM: Artificial sequence
<220> FEATURE:
<223> OTHER INFORMATION: DJ-1 derived peptide

<400> SEQUENCE: 181

Asp Val Val Ile Cys
1               5

<210> SEQ ID NO 182
<211> LENGTH: 5
```

```
<212> TYPE: PRT
<213> ORGANISM: Artificial sequence
<220> FEATURE:
<223> OTHER INFORMATION: DJ-1 derived peptide

<400> SEQUENCE: 182

Val Val Ile Cys Pro
1               5

<210> SEQ ID NO 183
<211> LENGTH: 5
<212> TYPE: PRT
<213> ORGANISM: Artificial sequence
<220> FEATURE:
<223> OTHER INFORMATION: DJ-1 derived peptide

<400> SEQUENCE: 183

Val Ile Cys Pro Asp
1               5

<210> SEQ ID NO 184
<211> LENGTH: 6
<212> TYPE: PRT
<213> ORGANISM: Artificial sequence
<220> FEATURE:
<223> OTHER INFORMATION: DJ-1 derived peptide

<400> SEQUENCE: 184

Val Gln Cys Ser Arg Asp
1               5

<210> SEQ ID NO 185
<211> LENGTH: 6
<212> TYPE: PRT
<213> ORGANISM: Artificial sequence
<220> FEATURE:
<223> OTHER INFORMATION: DJ-1 derived peptide

<400> SEQUENCE: 185

Gln Cys Ser Arg Asp Val
1               5

<210> SEQ ID NO 186
<211> LENGTH: 6
<212> TYPE: PRT
<213> ORGANISM: Artificial sequence
<220> FEATURE:
<223> OTHER INFORMATION: DJ-1 derived peptide

<400> SEQUENCE: 186

Cys Ser Arg Asp Val Val
1               5

<210> SEQ ID NO 187
<211> LENGTH: 6
<212> TYPE: PRT
<213> ORGANISM: Artificial sequence
<220> FEATURE:
<223> OTHER INFORMATION: DJ-1 derived peptide

<400> SEQUENCE: 187

Ser Arg Asp Val Val Ile
1               5

<210> SEQ ID NO 188
<211> LENGTH: 6
<212> TYPE: PRT
<213> ORGANISM: Artificial sequence
```

```
<220> FEATURE:
<223> OTHER INFORMATION: DJ-1 derived peptide

<400> SEQUENCE: 188

Arg Asp Val Val Ile Cys
1               5

<210> SEQ ID NO 189
<211> LENGTH: 6
<212> TYPE: PRT
<213> ORGANISM: Artificial sequence
<220> FEATURE:
<223> OTHER INFORMATION: DJ-1 derived peptide

<400> SEQUENCE: 189

Asp Val Val Ile Cys Pro
1               5

<210> SEQ ID NO 190
<211> LENGTH: 6
<212> TYPE: PRT
<213> ORGANISM: Artificial sequence
<220> FEATURE:
<223> OTHER INFORMATION: DJ-1 derived peptide

<400> SEQUENCE: 190

Val Val Ile Cys Pro Asp
1               5

<210> SEQ ID NO 191
<211> LENGTH: 7
<212> TYPE: PRT
<213> ORGANISM: Artificial sequence
<220> FEATURE:
<223> OTHER INFORMATION: DJ-1 derived peptide

<400> SEQUENCE: 191

Val Gln Cys Ser Arg Asp Val
1               5

<210> SEQ ID NO 192
<211> LENGTH: 7
<212> TYPE: PRT
<213> ORGANISM: Artificial sequence
<220> FEATURE:
<223> OTHER INFORMATION: DJ-1 derived peptide

<400> SEQUENCE: 192

Gln Cys Ser Arg Asp Val Val
1               5

<210> SEQ ID NO 193
<211> LENGTH: 7
<212> TYPE: PRT
<213> ORGANISM: Artificial sequence
<220> FEATURE:
<223> OTHER INFORMATION: DJ-1 derived peptide

<400> SEQUENCE: 193

Cys Ser Arg Asp Val Val Ile
1               5

<210> SEQ ID NO 194
<211> LENGTH: 7
<212> TYPE: PRT
<213> ORGANISM: Artificial sequence
<220> FEATURE:
<223> OTHER INFORMATION: DJ-1 derived peptide
```

```
<400> SEQUENCE: 194

Ser Arg Asp Val Val Ile Cys
1               5

<210> SEQ ID NO 195
<211> LENGTH: 7
<212> TYPE: PRT
<213> ORGANISM: Artificial sequence
<220> FEATURE:
<223> OTHER INFORMATION: DJ-1 derived peptide

<400> SEQUENCE: 195

Arg Asp Val Val Ile Cys Pro
1               5

<210> SEQ ID NO 196
<211> LENGTH: 7
<212> TYPE: PRT
<213> ORGANISM: Artificial sequence
<220> FEATURE:
<223> OTHER INFORMATION: DJ-1 derived peptide

<400> SEQUENCE: 196

Asp Val Val Ile Cys Pro Asp
1               5

<210> SEQ ID NO 197
<211> LENGTH: 8
<212> TYPE: PRT
<213> ORGANISM: Artificial sequence
<220> FEATURE:
<223> OTHER INFORMATION: DJ-1 derived peptide

<400> SEQUENCE: 197

Val Gln Cys Ser Arg Asp Val Val
1               5

<210> SEQ ID NO 198
<211> LENGTH: 8
<212> TYPE: PRT
<213> ORGANISM: Artificial sequence
<220> FEATURE:
<223> OTHER INFORMATION: DJ-1 derived peptide

<400> SEQUENCE: 198

Gln Cys Ser Arg Asp Val Val Ile
1               5

<210> SEQ ID NO 199
<211> LENGTH: 8
<212> TYPE: PRT
<213> ORGANISM: Artificial sequence
<220> FEATURE:
<223> OTHER INFORMATION: DJ-1 derived peptide

<400> SEQUENCE: 199

Cys Ser Arg Asp Val Val Ile Cys
1               5

<210> SEQ ID NO 200
<211> LENGTH: 8
<212> TYPE: PRT
<213> ORGANISM: Artificial sequence
<220> FEATURE:
<223> OTHER INFORMATION: DJ-1 derived peptide

<400> SEQUENCE: 200
```

```
Ser Arg Asp Val Val Ile Cys Pro
1               5

<210> SEQ ID NO 201
<211> LENGTH: 8
<212> TYPE: PRT
<213> ORGANISM: Artificial sequence
<220> FEATURE:
<223> OTHER INFORMATION: DJ-1 derived peptide

<400> SEQUENCE: 201

Arg Asp Val Val Ile Cys Pro Asp
1               5

<210> SEQ ID NO 202
<211> LENGTH: 9
<212> TYPE: PRT
<213> ORGANISM: Artificial sequence
<220> FEATURE:
<223> OTHER INFORMATION: DJ-1 derived peptide

<400> SEQUENCE: 202

Val Gln Cys Ser Arg Asp Val Val Ile
1               5

<210> SEQ ID NO 203
<211> LENGTH: 9
<212> TYPE: PRT
<213> ORGANISM: Artificial sequence
<220> FEATURE:
<223> OTHER INFORMATION: DJ-1 derived peptide

<400> SEQUENCE: 203

Gln Cys Ser Arg Asp Val Val Ile Cys
1               5

<210> SEQ ID NO 204
<211> LENGTH: 9
<212> TYPE: PRT
<213> ORGANISM: Artificial sequence
<220> FEATURE:
<223> OTHER INFORMATION: DJ-1 derived peptide

<400> SEQUENCE: 204

Cys Ser Arg Asp Val Val Ile Cys Pro
1               5

<210> SEQ ID NO 205
<211> LENGTH: 9
<212> TYPE: PRT
<213> ORGANISM: Artificial sequence
<220> FEATURE:
<223> OTHER INFORMATION: DJ-1 derived peptide

<400> SEQUENCE: 205

Ser Arg Asp Val Val Ile Cys Pro Asp
1               5

<210> SEQ ID NO 206
<211> LENGTH: 10
<212> TYPE: PRT
<213> ORGANISM: Artificial sequence
<220> FEATURE:
<223> OTHER INFORMATION: DJ-1 derived peptide

<400> SEQUENCE: 206

Val Gln Cys Ser Arg Asp Val Val Ile Cys
```

```
                    1               5                   10

<210> SEQ ID NO 207
<211> LENGTH: 10
<212> TYPE: PRT
<213> ORGANISM: Artificial sequence
<220> FEATURE:
<223> OTHER INFORMATION: DJ-1 derived peptide

<400> SEQUENCE: 207

Gln Cys Ser Arg Asp Val Val Ile Cys Pro
1               5                   10

<210> SEQ ID NO 208
<211> LENGTH: 10
<212> TYPE: PRT
<213> ORGANISM: Artificial sequence
<220> FEATURE:
<223> OTHER INFORMATION: DJ-1 derived peptide

<400> SEQUENCE: 208

Cys Ser Arg Asp Val Val Ile Cys Pro Asp
1               5                   10

<210> SEQ ID NO 209
<211> LENGTH: 11
<212> TYPE: PRT
<213> ORGANISM: Artificial sequence
<220> FEATURE:
<223> OTHER INFORMATION: DJ-1 derived peptide

<400> SEQUENCE: 209

Val Gln Cys Ser Arg Asp Val Val Ile Cys Pro
1               5                   10

<210> SEQ ID NO 210
<211> LENGTH: 11
<212> TYPE: PRT
<213> ORGANISM: Artificial sequence
<220> FEATURE:
<223> OTHER INFORMATION: DJ-1 derived peptide

<400> SEQUENCE: 210

Gln Cys Ser Arg Asp Val Val Ile Cys Pro Asp
1               5                   10

<210> SEQ ID NO 211
<211> LENGTH: 4
<212> TYPE: PRT
<213> ORGANISM: Artificial sequence
<220> FEATURE:
<223> OTHER INFORMATION: DJ-1 derived peptide

<400> SEQUENCE: 211

Val Val Val Leu
1

<210> SEQ ID NO 212
<211> LENGTH: 4
<212> TYPE: PRT
<213> ORGANISM: Artificial sequence
<220> FEATURE:
<223> OTHER INFORMATION: DJ-1 derived peptide

<400> SEQUENCE: 212

Val Val Leu Pro
1
```

```
<210> SEQ ID NO 213
<211> LENGTH: 4
<212> TYPE: PRT
<213> ORGANISM: Artificial sequence
<220> FEATURE:
<223> OTHER INFORMATION: DJ-1 derived peptide

<400> SEQUENCE: 213

Val Leu Pro Gly
1

<210> SEQ ID NO 214
<211> LENGTH: 4
<212> TYPE: PRT
<213> ORGANISM: Artificial sequence
<220> FEATURE:
<223> OTHER INFORMATION: DJ-1 derived peptide

<400> SEQUENCE: 214

Leu Pro Gly Gly
1

<210> SEQ ID NO 215
<211> LENGTH: 4
<212> TYPE: PRT
<213> ORGANISM: Artificial sequence
<220> FEATURE:
<223> OTHER INFORMATION: DJ-1 derived peptide

<400> SEQUENCE: 215

Pro Gly Gly Asn
1

<210> SEQ ID NO 216
<211> LENGTH: 4
<212> TYPE: PRT
<213> ORGANISM: Artificial sequence
<220> FEATURE:
<223> OTHER INFORMATION: DJ-1 derived peptide

<400> SEQUENCE: 216

Gly Gly Asn Leu
1

<210> SEQ ID NO 217
<211> LENGTH: 4
<212> TYPE: PRT
<213> ORGANISM: Artificial sequence
<220> FEATURE:
<223> OTHER INFORMATION: DJ-1 derived peptide

<400> SEQUENCE: 217

Gly Asn Leu Gly
1

<210> SEQ ID NO 218
<211> LENGTH: 4
<212> TYPE: PRT
<213> ORGANISM: Artificial sequence
<220> FEATURE:
<223> OTHER INFORMATION: DJ-1 derived peptide

<400> SEQUENCE: 218

Asn Leu Gly Ala
1

<210> SEQ ID NO 219
```

<211> LENGTH: 5
<212> TYPE: PRT
<213> ORGANISM: Artificial sequence
<220> FEATURE:
<223> OTHER INFORMATION: DJ-1 derived peptide

<400> SEQUENCE: 219

Val Val Val Leu Pro
1               5

<210> SEQ ID NO 220
<211> LENGTH: 5
<212> TYPE: PRT
<213> ORGANISM: Artificial sequence
<220> FEATURE:
<223> OTHER INFORMATION: DJ-1 derived peptide

<400> SEQUENCE: 220

Val Val Leu Pro Gly
1               5

<210> SEQ ID NO 221
<211> LENGTH: 5
<212> TYPE: PRT
<213> ORGANISM: Artificial sequence
<220> FEATURE:
<223> OTHER INFORMATION: DJ-1 derived peptide

<400> SEQUENCE: 221

Val Leu Pro Gly Gly
1               5

<210> SEQ ID NO 222
<211> LENGTH: 5
<212> TYPE: PRT
<213> ORGANISM: Artificial sequence
<220> FEATURE:
<223> OTHER INFORMATION: DJ-1 derived peptide

<400> SEQUENCE: 222

Leu Pro Gly Gly Asn
1               5

<210> SEQ ID NO 223
<211> LENGTH: 5
<212> TYPE: PRT
<213> ORGANISM: Artificial sequence
<220> FEATURE:
<223> OTHER INFORMATION: DJ-1 derived peptide

<400> SEQUENCE: 223

Pro Gly Gly Asn Leu
1               5

<210> SEQ ID NO 224
<211> LENGTH: 5
<212> TYPE: PRT
<213> ORGANISM: Artificial sequence
<220> FEATURE:
<223> OTHER INFORMATION: DJ-1 derived peptide

<400> SEQUENCE: 224

Gly Gly Asn Leu Gly
1               5

<210> SEQ ID NO 225
<211> LENGTH: 5
<212> TYPE: PRT

```
<213> ORGANISM: Artificial sequence
<220> FEATURE:
<223> OTHER INFORMATION: DJ-1 derived peptide

<400> SEQUENCE: 225

Gly Asn Leu Gly Ala
1               5

<210> SEQ ID NO 226
<211> LENGTH: 6
<212> TYPE: PRT
<213> ORGANISM: Artificial sequence
<220> FEATURE:
<223> OTHER INFORMATION: DJ-1 derived peptide

<400> SEQUENCE: 226

Val Val Val Leu Pro Gly
1               5

<210> SEQ ID NO 227
<211> LENGTH: 6
<212> TYPE: PRT
<213> ORGANISM: Artificial sequence
<220> FEATURE:
<223> OTHER INFORMATION: DJ-1 derived peptide

<400> SEQUENCE: 227

Val Val Leu Pro Gly Gly
1               5

<210> SEQ ID NO 228
<211> LENGTH: 6
<212> TYPE: PRT
<213> ORGANISM: Artificial sequence
<220> FEATURE:
<223> OTHER INFORMATION: DJ-1 derived peptide

<400> SEQUENCE: 228

Val Leu Pro Gly Gly Asn
1               5

<210> SEQ ID NO 229
<211> LENGTH: 6
<212> TYPE: PRT
<213> ORGANISM: Artificial sequence
<220> FEATURE:
<223> OTHER INFORMATION: DJ-1 derived peptide

<400> SEQUENCE: 229

Leu Pro Gly Gly Asn Leu
1               5

<210> SEQ ID NO 230
<211> LENGTH: 6
<212> TYPE: PRT
<213> ORGANISM: Artificial sequence
<220> FEATURE:
<223> OTHER INFORMATION: DJ-1 derived peptide

<400> SEQUENCE: 230

Pro Gly Gly Asn Leu Gly
1               5

<210> SEQ ID NO 231
<211> LENGTH: 6
<212> TYPE: PRT
<213> ORGANISM: Artificial sequence
<220> FEATURE:
```

-continued

<223> OTHER INFORMATION: DJ-1 derived peptide

<400> SEQUENCE: 231

Gly Gly Asn Leu Gly Ala
1               5

<210> SEQ ID NO 232
<211> LENGTH: 7
<212> TYPE: PRT
<213> ORGANISM: Artificial sequence
<220> FEATURE:
<223> OTHER INFORMATION: DJ-1 derived peptide

<400> SEQUENCE: 232

Val Val Val Leu Pro Gly Gly
1               5

<210> SEQ ID NO 233
<211> LENGTH: 7
<212> TYPE: PRT
<213> ORGANISM: Artificial sequence
<220> FEATURE:
<223> OTHER INFORMATION: DJ-1 derived peptide

<400> SEQUENCE: 233

Val Val Leu Pro Gly Gly Asn
1               5

<210> SEQ ID NO 234
<211> LENGTH: 7
<212> TYPE: PRT
<213> ORGANISM: Artificial sequence
<220> FEATURE:
<223> OTHER INFORMATION: DJ-1 derived peptide

<400> SEQUENCE: 234

Val Leu Pro Gly Gly Asn Leu
1               5

<210> SEQ ID NO 235
<211> LENGTH: 7
<212> TYPE: PRT
<213> ORGANISM: Artificial sequence
<220> FEATURE:
<223> OTHER INFORMATION: DJ-1 derived peptide

<400> SEQUENCE: 235

Leu Pro Gly Gly Asn Leu Gly
1               5

<210> SEQ ID NO 236
<211> LENGTH: 7
<212> TYPE: PRT
<213> ORGANISM: Artificial sequence
<220> FEATURE:
<223> OTHER INFORMATION: DJ-1 derived peptide

<400> SEQUENCE: 236

Pro Gly Gly Asn Leu Gly Ala
1               5

<210> SEQ ID NO 237
<211> LENGTH: 8
<212> TYPE: PRT
<213> ORGANISM: Artificial sequence
<220> FEATURE:
<223> OTHER INFORMATION: DJ-1 derived peptide

```
<400> SEQUENCE: 237

Val Val Val Leu Pro Gly Gly Asn
1               5

<210> SEQ ID NO 238
<211> LENGTH: 8
<212> TYPE: PRT
<213> ORGANISM: Artificial sequence
<220> FEATURE:
<223> OTHER INFORMATION: DJ-1 derived peptide

<400> SEQUENCE: 238

Val Val Leu Pro Gly Gly Asn Leu
1               5

<210> SEQ ID NO 239
<211> LENGTH: 8
<212> TYPE: PRT
<213> ORGANISM: Artificial sequence
<220> FEATURE:
<223> OTHER INFORMATION: DJ-1 derived peptide

<400> SEQUENCE: 239

Val Leu Pro Gly Gly Asn Leu Gly
1               5

<210> SEQ ID NO 240
<211> LENGTH: 8
<212> TYPE: PRT
<213> ORGANISM: Artificial sequence
<220> FEATURE:
<223> OTHER INFORMATION: DJ-1 derived peptide

<400> SEQUENCE: 240

Leu Pro Gly Gly Asn Leu Gly Ala
1               5

<210> SEQ ID NO 241
<211> LENGTH: 9
<212> TYPE: PRT
<213> ORGANISM: Artificial sequence
<220> FEATURE:
<223> OTHER INFORMATION: DJ-1 derived peptide

<400> SEQUENCE: 241

Val Val Val Leu Pro Gly Gly Asn Leu
1               5

<210> SEQ ID NO 242
<211> LENGTH: 9
<212> TYPE: PRT
<213> ORGANISM: Artificial sequence
<220> FEATURE:
<223> OTHER INFORMATION: DJ-1 derived peptide

<400> SEQUENCE: 242

Val Val Leu Pro Gly Gly Asn Leu Gly
1               5

<210> SEQ ID NO 243
<211> LENGTH: 9
<212> TYPE: PRT
<213> ORGANISM: Artificial sequence
<220> FEATURE:
<223> OTHER INFORMATION: DJ-1 derived peptide

<400> SEQUENCE: 243
```

```
Val Leu Pro Gly Gly Asn Leu Gly Ala
1               5

<210> SEQ ID NO 244
<211> LENGTH: 10
<212> TYPE: PRT
<213> ORGANISM: Artificial sequence
<220> FEATURE:
<223> OTHER INFORMATION: DJ-1 derived peptide

<400> SEQUENCE: 244

Val Val Val Leu Pro Gly Gly Asn Leu Gly
1               5                   10

<210> SEQ ID NO 245
<211> LENGTH: 10
<212> TYPE: PRT
<213> ORGANISM: Artificial sequence
<220> FEATURE:
<223> OTHER INFORMATION: DJ-1 derived peptide

<400> SEQUENCE: 245

Val Val Leu Pro Gly Gly Asn Leu Gly Ala
1               5                   10

<210> SEQ ID NO 246
<211> LENGTH: 4
<212> TYPE: PRT
<213> ORGANISM: Artificial sequence
<220> FEATURE:
<223> OTHER INFORMATION: DJ-1 derived peptide

<400> SEQUENCE: 246

Ala Ala Ile Cys
1

<210> SEQ ID NO 247
<211> LENGTH: 4
<212> TYPE: PRT
<213> ORGANISM: Artificial sequence
<220> FEATURE:
<223> OTHER INFORMATION: DJ-1 derived peptide

<400> SEQUENCE: 247

Ala Ile Cys Ala
1

<210> SEQ ID NO 248
<211> LENGTH: 4
<212> TYPE: PRT
<213> ORGANISM: Artificial sequence
<220> FEATURE:
<223> OTHER INFORMATION: DJ-1 derived peptide

<400> SEQUENCE: 248

Ile Cys Ala Gly
1

<210> SEQ ID NO 249
<211> LENGTH: 4
<212> TYPE: PRT
<213> ORGANISM: Artificial sequence
<220> FEATURE:
<223> OTHER INFORMATION: DJ-1 derived peptide

<400> SEQUENCE: 249

Cys Ala Gly Pro
1
```

```
<210> SEQ ID NO 250
<211> LENGTH: 4
<212> TYPE: PRT
<213> ORGANISM: Artificial sequence
<220> FEATURE:
<223> OTHER INFORMATION: DJ-1 derived peptide

<400> SEQUENCE: 250

Ala Gly Pro Thr
1

<210> SEQ ID NO 251
<211> LENGTH: 4
<212> TYPE: PRT
<213> ORGANISM: Artificial sequence
<220> FEATURE:
<223> OTHER INFORMATION: DJ-1 derived peptide

<400> SEQUENCE: 251

Gly Pro Thr Ala
1

<210> SEQ ID NO 252
<211> LENGTH: 4
<212> TYPE: PRT
<213> ORGANISM: Artificial sequence
<220> FEATURE:
<223> OTHER INFORMATION: DJ-1 derived peptide

<400> SEQUENCE: 252

Pro Thr Ala Leu
1

<210> SEQ ID NO 253
<211> LENGTH: 5
<212> TYPE: PRT
<213> ORGANISM: Artificial sequence
<220> FEATURE:
<223> OTHER INFORMATION: DJ-1 derived peptide

<400> SEQUENCE: 253

Ala Ala Ile Cys Ala
1               5

<210> SEQ ID NO 254
<211> LENGTH: 5
<212> TYPE: PRT
<213> ORGANISM: Artificial sequence
<220> FEATURE:
<223> OTHER INFORMATION: DJ-1 derived peptide

<400> SEQUENCE: 254

Ala Ile Cys Ala Gly
1               5

<210> SEQ ID NO 255
<211> LENGTH: 5
<212> TYPE: PRT
<213> ORGANISM: Artificial sequence
<220> FEATURE:
<223> OTHER INFORMATION: DJ-1 derived peptide

<400> SEQUENCE: 255

Ile Cys Ala Gly Pro
1               5
```

```
<210> SEQ ID NO 256
<211> LENGTH: 5
<212> TYPE: PRT
<213> ORGANISM: Artificial sequence
<220> FEATURE:
<223> OTHER INFORMATION: DJ-1 derived peptide

<400> SEQUENCE: 256

Cys Ala Gly Pro Thr
1               5

<210> SEQ ID NO 257
<211> LENGTH: 5
<212> TYPE: PRT
<213> ORGANISM: Artificial sequence
<220> FEATURE:
<223> OTHER INFORMATION: DJ-1 derived peptide

<400> SEQUENCE: 257

Ala Gly Pro Thr Ala
1               5

<210> SEQ ID NO 258
<211> LENGTH: 5
<212> TYPE: PRT
<213> ORGANISM: Artificial sequence
<220> FEATURE:
<223> OTHER INFORMATION: DJ-1 derived peptide

<400> SEQUENCE: 258

Gly Pro Thr Ala Leu
1               5

<210> SEQ ID NO 259
<211> LENGTH: 6
<212> TYPE: PRT
<213> ORGANISM: Artificial sequence
<220> FEATURE:
<223> OTHER INFORMATION: DJ-1 derived peptide

<400> SEQUENCE: 259

Ala Ala Ile Cys Ala Gly
1               5

<210> SEQ ID NO 260
<211> LENGTH: 6
<212> TYPE: PRT
<213> ORGANISM: Artificial sequence
<220> FEATURE:
<223> OTHER INFORMATION: DJ-1 derived peptide

<400> SEQUENCE: 260

Ala Ile Cys Ala Gly Pro
1               5

<210> SEQ ID NO 261
<211> LENGTH: 6
<212> TYPE: PRT
<213> ORGANISM: Artificial sequence
<220> FEATURE:
<223> OTHER INFORMATION: DJ-1 derived peptide

<400> SEQUENCE: 261

Ile Cys Ala Gly Pro Thr
1               5

<210> SEQ ID NO 262
<211> LENGTH: 6
```

```
<212> TYPE: PRT
<213> ORGANISM: Artificial sequence
<220> FEATURE:
<223> OTHER INFORMATION: DJ-1 derived peptide

<400> SEQUENCE: 262

Cys Ala Gly Pro Thr Ala
1               5

<210> SEQ ID NO 263
<211> LENGTH: 6
<212> TYPE: PRT
<213> ORGANISM: Artificial sequence
<220> FEATURE:
<223> OTHER INFORMATION: DJ-1 derived peptide

<400> SEQUENCE: 263

Ala Gly Pro Thr Ala Leu
1               5

<210> SEQ ID NO 264
<211> LENGTH: 7
<212> TYPE: PRT
<213> ORGANISM: Artificial sequence
<220> FEATURE:
<223> OTHER INFORMATION: DJ-1 derived peptide

<400> SEQUENCE: 264

Ala Ala Ile Cys Ala Gly Pro
1               5

<210> SEQ ID NO 265
<211> LENGTH: 7
<212> TYPE: PRT
<213> ORGANISM: Artificial sequence
<220> FEATURE:
<223> OTHER INFORMATION: DJ-1 derived peptide

<400> SEQUENCE: 265

Ala Ile Cys Ala Gly Pro Thr
1               5

<210> SEQ ID NO 266
<211> LENGTH: 7
<212> TYPE: PRT
<213> ORGANISM: Artificial sequence
<220> FEATURE:
<223> OTHER INFORMATION: DJ-1 derived peptide

<400> SEQUENCE: 266

Ile Cys Ala Gly Pro Thr Ala
1               5

<210> SEQ ID NO 267
<211> LENGTH: 7
<212> TYPE: PRT
<213> ORGANISM: Artificial sequence
<220> FEATURE:
<223> OTHER INFORMATION: DJ-1 derived peptide

<400> SEQUENCE: 267

Cys Ala Gly Pro Thr Ala Leu
1               5

<210> SEQ ID NO 268
<211> LENGTH: 8
<212> TYPE: PRT
<213> ORGANISM: Artificial sequence
```

<220> FEATURE:
<223> OTHER INFORMATION: DJ-1 derived peptide

<400> SEQUENCE: 268

Ala Ala Ile Cys Ala Gly Pro Thr
1               5

<210> SEQ ID NO 269
<211> LENGTH: 8
<212> TYPE: PRT
<213> ORGANISM: Artificial sequence
<220> FEATURE:
<223> OTHER INFORMATION: DJ-1 derived peptide

<400> SEQUENCE: 269

Ala Ile Cys Ala Gly Pro Thr Ala
1               5

<210> SEQ ID NO 270
<211> LENGTH: 8
<212> TYPE: PRT
<213> ORGANISM: Artificial sequence
<220> FEATURE:
<223> OTHER INFORMATION: DJ-1 derived peptide

<400> SEQUENCE: 270

Ile Cys Ala Gly Pro Thr Ala Leu
1               5

<210> SEQ ID NO 271
<211> LENGTH: 9
<212> TYPE: PRT
<213> ORGANISM: Artificial sequence
<220> FEATURE:
<223> OTHER INFORMATION: DJ-1 derived peptide

<400> SEQUENCE: 271

Ala Ala Ile Cys Ala Gly Pro Thr Ala
1               5

<210> SEQ ID NO 272
<211> LENGTH: 9
<212> TYPE: PRT
<213> ORGANISM: Artificial sequence
<220> FEATURE:
<223> OTHER INFORMATION: DJ-1 derived peptide

<400> SEQUENCE: 272

Ala Ile Cys Ala Gly Pro Thr Ala Leu
1               5

<210> SEQ ID NO 273
<211> LENGTH: 4
<212> TYPE: PRT
<213> ORGANISM: Artificial sequence
<220> FEATURE:
<223> OTHER INFORMATION: DJ-1 derived peptide

<400> SEQUENCE: 273

Thr Thr His Pro
1

<210> SEQ ID NO 274
<211> LENGTH: 4
<212> TYPE: PRT
<213> ORGANISM: Artificial sequence
<220> FEATURE:
<223> OTHER INFORMATION: DJ-1 derived peptide

```
<400> SEQUENCE: 274

Thr His Pro Leu
1

<210> SEQ ID NO 275
<211> LENGTH: 4
<212> TYPE: PRT
<213> ORGANISM: Artificial sequence
<220> FEATURE:
<223> OTHER INFORMATION: DJ-1 derived peptide

<400> SEQUENCE: 275

His Pro Leu Ala
1

<210> SEQ ID NO 276
<211> LENGTH: 4
<212> TYPE: PRT
<213> ORGANISM: Artificial sequence
<220> FEATURE:
<223> OTHER INFORMATION: DJ-1 derived peptide

<400> SEQUENCE: 276

Pro Leu Ala Lys
1

<210> SEQ ID NO 277
<211> LENGTH: 5
<212> TYPE: PRT
<213> ORGANISM: Artificial sequence
<220> FEATURE:
<223> OTHER INFORMATION: DJ-1 derived peptide

<400> SEQUENCE: 277

Thr Thr His Pro Leu
1               5

<210> SEQ ID NO 278
<211> LENGTH: 5
<212> TYPE: PRT
<213> ORGANISM: Artificial sequence
<220> FEATURE:
<223> OTHER INFORMATION: DJ-1 derived peptide

<400> SEQUENCE: 278

Thr His Pro Leu Ala
1               5

<210> SEQ ID NO 279
<211> LENGTH: 5
<212> TYPE: PRT
<213> ORGANISM: Artificial sequence
<220> FEATURE:
<223> OTHER INFORMATION: DJ-1 derived peptide

<400> SEQUENCE: 279

His Pro Leu Ala Lys
1               5

<210> SEQ ID NO 280
<211> LENGTH: 6
<212> TYPE: PRT
<213> ORGANISM: Artificial sequence
<220> FEATURE:
<223> OTHER INFORMATION: DJ-1 derived peptide

<400> SEQUENCE: 280
```

Thr Thr His Pro Leu Ala
1               5

<210> SEQ ID NO 281
<211> LENGTH: 6
<212> TYPE: PRT
<213> ORGANISM: Artificial sequence
<220> FEATURE:
<223> OTHER INFORMATION: DJ-1 derived peptide

<400> SEQUENCE: 281

Thr His Pro Leu Ala Lys
1               5

<210> SEQ ID NO 282
<211> LENGTH: 4
<212> TYPE: PRT
<213> ORGANISM: Artificial sequence
<220> FEATURE:
<223> OTHER INFORMATION: DJ-1 derived peptide

<400> SEQUENCE: 282

Val Glu Lys Asp
1

<210> SEQ ID NO 283
<211> LENGTH: 4
<212> TYPE: PRT
<213> ORGANISM: Artificial sequence
<220> FEATURE:
<223> OTHER INFORMATION: DJ-1 derived peptide

<400> SEQUENCE: 283

Glu Lys Asp Gly
1

<210> SEQ ID NO 284
<211> LENGTH: 4
<212> TYPE: PRT
<213> ORGANISM: Artificial sequence
<220> FEATURE:
<223> OTHER INFORMATION: DJ-1 derived peptide

<400> SEQUENCE: 284

Lys Asp Gly Leu
1

<210> SEQ ID NO 285
<211> LENGTH: 4
<212> TYPE: PRT
<213> ORGANISM: Artificial sequence
<220> FEATURE:
<223> OTHER INFORMATION: DJ-1 derived peptide

<400> SEQUENCE: 285

Asp Gly Leu Ile
1

<210> SEQ ID NO 286
<211> LENGTH: 4
<212> TYPE: PRT
<213> ORGANISM: Artificial sequence
<220> FEATURE:
<223> OTHER INFORMATION: DJ-1 derived peptide

<400> SEQUENCE: 286

Gly Leu Ile Leu

```
<210> SEQ ID NO 287
<211> LENGTH: 4
<212> TYPE: PRT
<213> ORGANISM: Artificial sequence
<220> FEATURE:
<223> OTHER INFORMATION: DJ-1 derived peptide

<400> SEQUENCE: 287

Leu Ile Leu Thr
1

<210> SEQ ID NO 288
<211> LENGTH: 4
<212> TYPE: PRT
<213> ORGANISM: Artificial sequence
<220> FEATURE:
<223> OTHER INFORMATION: DJ-1 derived peptide

<400> SEQUENCE: 288

Ile Leu Thr Ser
1

<210> SEQ ID NO 289
<211> LENGTH: 4
<212> TYPE: PRT
<213> ORGANISM: Artificial sequence
<220> FEATURE:
<223> OTHER INFORMATION: DJ-1 derived peptide

<400> SEQUENCE: 289

Leu Thr Ser Arg
1

<210> SEQ ID NO 290
<211> LENGTH: 4
<212> TYPE: PRT
<213> ORGANISM: Artificial sequence
<220> FEATURE:
<223> OTHER INFORMATION: DJ-1 derived peptide

<400> SEQUENCE: 290

Thr Ser Arg Gly
1

<210> SEQ ID NO 291
<211> LENGTH: 4
<212> TYPE: PRT
<213> ORGANISM: Artificial sequence
<220> FEATURE:
<223> OTHER INFORMATION: DJ-1 derived peptide

<400> SEQUENCE: 291

Ser Arg Gly Pro
1

<210> SEQ ID NO 292
<211> LENGTH: 4
<212> TYPE: PRT
<213> ORGANISM: Artificial sequence
<220> FEATURE:
<223> OTHER INFORMATION: DJ-1 derived peptide

<400> SEQUENCE: 292

Arg Gly Pro Gly
1
```

```
<210> SEQ ID NO 293
<211> LENGTH: 4
<212> TYPE: PRT
<213> ORGANISM: Artificial sequence
<220> FEATURE:
<223> OTHER INFORMATION: DJ-1 derived peptide

<400> SEQUENCE: 293

Gly Pro Gly Thr
1

<210> SEQ ID NO 294
<211> LENGTH: 4
<212> TYPE: PRT
<213> ORGANISM: Artificial sequence
<220> FEATURE:
<223> OTHER INFORMATION: DJ-1 derived peptide

<400> SEQUENCE: 294

Pro Gly Thr Ser
1

<210> SEQ ID NO 295
<211> LENGTH: 4
<212> TYPE: PRT
<213> ORGANISM: Artificial sequence
<220> FEATURE:
<223> OTHER INFORMATION: DJ-1 derived peptide

<400> SEQUENCE: 295

Gly Thr Ser Phe
1

<210> SEQ ID NO 296
<211> LENGTH: 4
<212> TYPE: PRT
<213> ORGANISM: Artificial sequence
<220> FEATURE:
<223> OTHER INFORMATION: DJ-1 derived peptide

<400> SEQUENCE: 296

Thr Ser Phe Glu
1

<210> SEQ ID NO 297
<211> LENGTH: 4
<212> TYPE: PRT
<213> ORGANISM: Artificial sequence
<220> FEATURE:
<223> OTHER INFORMATION: DJ-1 derived peptide

<400> SEQUENCE: 297

Ser Phe Glu Phe
1

<210> SEQ ID NO 298
<211> LENGTH: 4
<212> TYPE: PRT
<213> ORGANISM: Artificial sequence
<220> FEATURE:
<223> OTHER INFORMATION: DJ-1 derived peptide

<400> SEQUENCE: 298

Phe Glu Phe Ala
1

<210> SEQ ID NO 299
```

```
<211> LENGTH: 4
<212> TYPE: PRT
<213> ORGANISM: Artificial sequence
<220> FEATURE:
<223> OTHER INFORMATION: DJ-1 derived peptide

<400> SEQUENCE: 299

Glu Phe Ala Leu
1

<210> SEQ ID NO 300
<211> LENGTH: 4
<212> TYPE: PRT
<213> ORGANISM: Artificial sequence
<220> FEATURE:
<223> OTHER INFORMATION: DJ-1 derived peptide

<400> SEQUENCE: 300

Phe Ala Leu Ala
1

<210> SEQ ID NO 301
<211> LENGTH: 4
<212> TYPE: PRT
<213> ORGANISM: Artificial sequence
<220> FEATURE:
<223> OTHER INFORMATION: DJ-1 derived peptide

<400> SEQUENCE: 301

Ala Leu Ala Ile
1

<210> SEQ ID NO 302
<211> LENGTH: 4
<212> TYPE: PRT
<213> ORGANISM: Artificial sequence
<220> FEATURE:
<223> OTHER INFORMATION: DJ-1 derived peptide

<400> SEQUENCE: 302

Leu Ala Ile Val
1

<210> SEQ ID NO 303
<211> LENGTH: 4
<212> TYPE: PRT
<213> ORGANISM: Artificial sequence
<220> FEATURE:
<223> OTHER INFORMATION: DJ-1 derived peptide

<400> SEQUENCE: 303

Ala Ile Val Glu
1

<210> SEQ ID NO 304
<211> LENGTH: 4
<212> TYPE: PRT
<213> ORGANISM: Artificial sequence
<220> FEATURE:
<223> OTHER INFORMATION: DJ-1 derived peptide

<400> SEQUENCE: 304

Ile Val Glu Ala
1

<210> SEQ ID NO 305
<211> LENGTH: 4
<212> TYPE: PRT
```

```
<213> ORGANISM: Artificial sequence
<220> FEATURE:
<223> OTHER INFORMATION: DJ-1 derived peptide

<400> SEQUENCE: 305

Val Glu Ala Leu
1

<210> SEQ ID NO 306
<211> LENGTH: 4
<212> TYPE: PRT
<213> ORGANISM: Artificial sequence
<220> FEATURE:
<223> OTHER INFORMATION: DJ-1 derived peptide

<400> SEQUENCE: 306

Glu Ala Leu Asn
1

<210> SEQ ID NO 307
<211> LENGTH: 4
<212> TYPE: PRT
<213> ORGANISM: Artificial sequence
<220> FEATURE:
<223> OTHER INFORMATION: DJ-1 derived peptide

<400> SEQUENCE: 307

Ala Leu Asn Gly
1

<210> SEQ ID NO 308
<211> LENGTH: 5
<212> TYPE: PRT
<213> ORGANISM: Artificial sequence
<220> FEATURE:
<223> OTHER INFORMATION: DJ-1 derived peptide

<400> SEQUENCE: 308

Val Glu Lys Asp Gly
1               5

<210> SEQ ID NO 309
<211> LENGTH: 5
<212> TYPE: PRT
<213> ORGANISM: Artificial sequence
<220> FEATURE:
<223> OTHER INFORMATION: DJ-1 derived peptide

<400> SEQUENCE: 309

Glu Lys Asp Gly Leu
1               5

<210> SEQ ID NO 310
<211> LENGTH: 5
<212> TYPE: PRT
<213> ORGANISM: Artificial sequence
<220> FEATURE:
<223> OTHER INFORMATION: DJ-1 derived peptide

<400> SEQUENCE: 310

Lys Asp Gly Leu Ile
1               5

<210> SEQ ID NO 311
<211> LENGTH: 5
<212> TYPE: PRT
<213> ORGANISM: Artificial sequence
<220> FEATURE:
```

<223> OTHER INFORMATION: DJ-1 derived peptide

<400> SEQUENCE: 311

Asp Gly Leu Ile Leu
1               5

<210> SEQ ID NO 312
<211> LENGTH: 5
<212> TYPE: PRT
<213> ORGANISM: Artificial sequence
<220> FEATURE:
<223> OTHER INFORMATION: DJ-1 derived peptide

<400> SEQUENCE: 312

Gly Leu Ile Leu Thr
1               5

<210> SEQ ID NO 313
<211> LENGTH: 5
<212> TYPE: PRT
<213> ORGANISM: Artificial sequence
<220> FEATURE:
<223> OTHER INFORMATION: DJ-1 derived peptide

<400> SEQUENCE: 313

Leu Ile Leu Thr Ser
1               5

<210> SEQ ID NO 314
<211> LENGTH: 5
<212> TYPE: PRT
<213> ORGANISM: Artificial sequence
<220> FEATURE:
<223> OTHER INFORMATION: DJ-1 derived peptide

<400> SEQUENCE: 314

Ile Leu Thr Ser Arg
1               5

<210> SEQ ID NO 315
<211> LENGTH: 5
<212> TYPE: PRT
<213> ORGANISM: Artificial sequence
<220> FEATURE:
<223> OTHER INFORMATION: DJ-1 derived peptide

<400> SEQUENCE: 315

Leu Thr Ser Arg Gly
1               5

<210> SEQ ID NO 316
<211> LENGTH: 5
<212> TYPE: PRT
<213> ORGANISM: Artificial sequence
<220> FEATURE:
<223> OTHER INFORMATION: DJ-1 derived peptide

<400> SEQUENCE: 316

Thr Ser Arg Gly Pro
1               5

<210> SEQ ID NO 317
<211> LENGTH: 5
<212> TYPE: PRT
<213> ORGANISM: Artificial sequence
<220> FEATURE:
<223> OTHER INFORMATION: DJ-1 derived peptide -continued

```
<400> SEQUENCE: 317

Ser Arg Gly Pro Gly
1               5

<210> SEQ ID NO 318
<211> LENGTH: 5
<212> TYPE: PRT
<213> ORGANISM: Artificial sequence
<220> FEATURE:
<223> OTHER INFORMATION: DJ-1 derived peptide

<400> SEQUENCE: 318

Arg Gly Pro Gly Thr
1               5

<210> SEQ ID NO 319
<211> LENGTH: 5
<212> TYPE: PRT
<213> ORGANISM: Artificial sequence
<220> FEATURE:
<223> OTHER INFORMATION: DJ-1 derived peptide

<400> SEQUENCE: 319

Gly Pro Gly Thr Ser
1               5

<210> SEQ ID NO 320
<211> LENGTH: 5
<212> TYPE: PRT
<213> ORGANISM: Artificial sequence
<220> FEATURE:
<223> OTHER INFORMATION: DJ-1 derived peptide

<400> SEQUENCE: 320

Pro Gly Thr Ser Phe
1               5

<210> SEQ ID NO 321
<211> LENGTH: 5
<212> TYPE: PRT
<213> ORGANISM: Artificial sequence
<220> FEATURE:
<223> OTHER INFORMATION: DJ-1 derived peptide

<400> SEQUENCE: 321

Gly Thr Ser Phe Glu
1               5

<210> SEQ ID NO 322
<211> LENGTH: 5
<212> TYPE: PRT
<213> ORGANISM: Artificial sequence
<220> FEATURE:
<223> OTHER INFORMATION: DJ-1 derived peptide

<400> SEQUENCE: 322

Thr Ser Phe Glu Phe
1               5

<210> SEQ ID NO 323
<211> LENGTH: 5
<212> TYPE: PRT
<213> ORGANISM: Artificial sequence
<220> FEATURE:
<223> OTHER INFORMATION: DJ-1 derived peptide

<400> SEQUENCE: 323
```

Ser Phe Glu Phe Ala
1               5

<210> SEQ ID NO 324
<211> LENGTH: 5
<212> TYPE: PRT
<213> ORGANISM: Artificial sequence
<220> FEATURE:
<223> OTHER INFORMATION: DJ-1 derived peptide

<400> SEQUENCE: 324

Phe Glu Phe Ala Leu
1               5

<210> SEQ ID NO 325
<211> LENGTH: 5
<212> TYPE: PRT
<213> ORGANISM: Artificial sequence
<220> FEATURE:
<223> OTHER INFORMATION: DJ-1 derived peptide

<400> SEQUENCE: 325

Glu Phe Ala Leu Ala
1               5

<210> SEQ ID NO 326
<211> LENGTH: 5
<212> TYPE: PRT
<213> ORGANISM: Artificial sequence
<220> FEATURE:
<223> OTHER INFORMATION: DJ-1 derived peptide

<400> SEQUENCE: 326

Phe Ala Leu Ala Ile
1               5

<210> SEQ ID NO 327
<211> LENGTH: 5
<212> TYPE: PRT
<213> ORGANISM: Artificial sequence
<220> FEATURE:
<223> OTHER INFORMATION: DJ-1 derived peptide

<400> SEQUENCE: 327

Ala Leu Ala Ile Val
1               5

<210> SEQ ID NO 328
<211> LENGTH: 5
<212> TYPE: PRT
<213> ORGANISM: Artificial sequence
<220> FEATURE:
<223> OTHER INFORMATION: DJ-1 derived peptide

<400> SEQUENCE: 328

Leu Ala Ile Val Glu
1               5

<210> SEQ ID NO 329
<211> LENGTH: 5
<212> TYPE: PRT
<213> ORGANISM: Artificial sequence
<220> FEATURE:
<223> OTHER INFORMATION: DJ-1 derived peptide

<400> SEQUENCE: 329

Ala Ile Val Glu Ala
1               5

```
<210> SEQ ID NO 330
<211> LENGTH: 5
<212> TYPE: PRT
<213> ORGANISM: Artificial sequence
<220> FEATURE:
<223> OTHER INFORMATION: DJ-1 derived peptide

<400> SEQUENCE: 330

Ile Val Glu Ala Leu
1               5

<210> SEQ ID NO 331
<211> LENGTH: 5
<212> TYPE: PRT
<213> ORGANISM: Artificial sequence
<220> FEATURE:
<223> OTHER INFORMATION: DJ-1 derived peptide

<400> SEQUENCE: 331

Val Glu Ala Leu Asn
1               5

<210> SEQ ID NO 332
<211> LENGTH: 5
<212> TYPE: PRT
<213> ORGANISM: Artificial sequence
<220> FEATURE:
<223> OTHER INFORMATION: DJ-1 derived peptide

<400> SEQUENCE: 332

Glu Ala Leu Asn Gly
1               5

<210> SEQ ID NO 333
<211> LENGTH: 6
<212> TYPE: PRT
<213> ORGANISM: Artificial sequence
<220> FEATURE:
<223> OTHER INFORMATION: DJ-1 derived peptide

<400> SEQUENCE: 333

Val Glu Lys Asp Gly Leu
1               5

<210> SEQ ID NO 334
<211> LENGTH: 6
<212> TYPE: PRT
<213> ORGANISM: Artificial sequence
<220> FEATURE:
<223> OTHER INFORMATION: DJ-1 derived peptide

<400> SEQUENCE: 334

Glu Lys Asp Gly Leu Ile
1               5

<210> SEQ ID NO 335
<211> LENGTH: 6
<212> TYPE: PRT
<213> ORGANISM: Artificial sequence
<220> FEATURE:
<223> OTHER INFORMATION: DJ-1 derived peptide

<400> SEQUENCE: 335

Lys Asp Gly Leu Ile Leu
1               5
```

```
<210> SEQ ID NO 336
<211> LENGTH: 6
<212> TYPE: PRT
<213> ORGANISM: Artificial sequence
<220> FEATURE:
<223> OTHER INFORMATION: DJ-1 derived peptide

<400> SEQUENCE: 336

Asp Gly Leu Ile Leu Thr
1               5

<210> SEQ ID NO 337
<211> LENGTH: 6
<212> TYPE: PRT
<213> ORGANISM: Artificial sequence
<220> FEATURE:
<223> OTHER INFORMATION: DJ-1 derived peptide

<400> SEQUENCE: 337

Gly Leu Ile Leu Thr Ser
1               5

<210> SEQ ID NO 338
<211> LENGTH: 6
<212> TYPE: PRT
<213> ORGANISM: Artificial sequence
<220> FEATURE:
<223> OTHER INFORMATION: DJ-1 derived peptide

<400> SEQUENCE: 338

Leu Ile Leu Thr Ser Arg
1               5

<210> SEQ ID NO 339
<211> LENGTH: 6
<212> TYPE: PRT
<213> ORGANISM: Artificial sequence
<220> FEATURE:
<223> OTHER INFORMATION: DJ-1 derived peptide

<400> SEQUENCE: 339

Ile Leu Thr Ser Arg Gly
1               5

<210> SEQ ID NO 340
<211> LENGTH: 6
<212> TYPE: PRT
<213> ORGANISM: Artificial sequence
<220> FEATURE:
<223> OTHER INFORMATION: DJ-1 derived peptide

<400> SEQUENCE: 340

Leu Thr Ser Arg Gly Pro
1               5

<210> SEQ ID NO 341
<211> LENGTH: 6
<212> TYPE: PRT
<213> ORGANISM: Artificial sequence
<220> FEATURE:
<223> OTHER INFORMATION: DJ-1 derived peptide

<400> SEQUENCE: 341

Thr Ser Arg Gly Pro Gly
1               5

<210> SEQ ID NO 342
<211> LENGTH: 6
```

```
<212> TYPE: PRT
<213> ORGANISM: Artificial sequence
<220> FEATURE:
<223> OTHER INFORMATION: DJ-1 derived peptide

<400> SEQUENCE: 342

Ser Arg Gly Pro Gly Thr
1               5

<210> SEQ ID NO 343
<211> LENGTH: 6
<212> TYPE: PRT
<213> ORGANISM: Artificial sequence
<220> FEATURE:
<223> OTHER INFORMATION: DJ-1 derived peptide

<400> SEQUENCE: 343

Arg Gly Pro Gly Thr Ser
1               5

<210> SEQ ID NO 344
<211> LENGTH: 6
<212> TYPE: PRT
<213> ORGANISM: Artificial sequence
<220> FEATURE:
<223> OTHER INFORMATION: DJ-1 derived peptide

<400> SEQUENCE: 344

Gly Pro Gly Thr Ser Phe
1               5

<210> SEQ ID NO 345
<211> LENGTH: 6
<212> TYPE: PRT
<213> ORGANISM: Artificial sequence
<220> FEATURE:
<223> OTHER INFORMATION: DJ-1 derived peptide

<400> SEQUENCE: 345

Pro Gly Thr Ser Phe Glu
1               5

<210> SEQ ID NO 346
<211> LENGTH: 6
<212> TYPE: PRT
<213> ORGANISM: Artificial sequence
<220> FEATURE:
<223> OTHER INFORMATION: DJ-1 derived peptide

<400> SEQUENCE: 346

Gly Thr Ser Phe Glu Phe
1               5

<210> SEQ ID NO 347
<211> LENGTH: 6
<212> TYPE: PRT
<213> ORGANISM: Artificial sequence
<220> FEATURE:
<223> OTHER INFORMATION: DJ-1 derived peptide

<400> SEQUENCE: 347

Thr Ser Phe Glu Phe Ala
1               5

<210> SEQ ID NO 348
<211> LENGTH: 6
<212> TYPE: PRT
<213> ORGANISM: Artificial sequence
```

```
<220> FEATURE:
<223> OTHER INFORMATION: DJ-1 derived peptide

<400> SEQUENCE: 348

Ser Phe Glu Phe Ala Leu
1               5

<210> SEQ ID NO 349
<211> LENGTH: 6
<212> TYPE: PRT
<213> ORGANISM: Artificial sequence
<220> FEATURE:
<223> OTHER INFORMATION: DJ-1 derived peptide

<400> SEQUENCE: 349

Phe Glu Phe Ala Leu Ala
1               5

<210> SEQ ID NO 350
<211> LENGTH: 6
<212> TYPE: PRT
<213> ORGANISM: Artificial sequence
<220> FEATURE:
<223> OTHER INFORMATION: DJ-1 derived peptide

<400> SEQUENCE: 350

Glu Phe Ala Leu Ala Ile
1               5

<210> SEQ ID NO 351
<211> LENGTH: 6
<212> TYPE: PRT
<213> ORGANISM: Artificial sequence
<220> FEATURE:
<223> OTHER INFORMATION: DJ-1 derived peptide

<400> SEQUENCE: 351

Phe Ala Leu Ala Ile Val
1               5

<210> SEQ ID NO 352
<211> LENGTH: 6
<212> TYPE: PRT
<213> ORGANISM: Artificial sequence
<220> FEATURE:
<223> OTHER INFORMATION: DJ-1 derived peptide

<400> SEQUENCE: 352

Ala Leu Ala Ile Val Glu
1               5

<210> SEQ ID NO 353
<211> LENGTH: 6
<212> TYPE: PRT
<213> ORGANISM: Artificial sequence
<220> FEATURE:
<223> OTHER INFORMATION: DJ-1 derived peptide

<400> SEQUENCE: 353

Leu Ala Ile Val Glu Ala
1               5

<210> SEQ ID NO 354
<211> LENGTH: 6
<212> TYPE: PRT
<213> ORGANISM: Artificial sequence
<220> FEATURE:
<223> OTHER INFORMATION: DJ-1 derived peptide
```

<400> SEQUENCE: 354

Ala Ile Val Glu Ala Leu
1               5

<210> SEQ ID NO 355
<211> LENGTH: 6
<212> TYPE: PRT
<213> ORGANISM: Artificial sequence
<220> FEATURE:
<223> OTHER INFORMATION: DJ-1 derived peptide

<400> SEQUENCE: 355

Ile Val Glu Ala Leu Asn
1               5

<210> SEQ ID NO 356
<211> LENGTH: 6
<212> TYPE: PRT
<213> ORGANISM: Artificial sequence
<220> FEATURE:
<223> OTHER INFORMATION: DJ-1 derived peptide

<400> SEQUENCE: 356

Val Glu Ala Leu Asn Gly
1               5

<210> SEQ ID NO 357
<211> LENGTH: 7
<212> TYPE: PRT
<213> ORGANISM: Artificial sequence
<220> FEATURE:
<223> OTHER INFORMATION: DJ-1 derived peptide

<400> SEQUENCE: 357

Val Glu Lys Asp Gly Leu Ile
1               5

<210> SEQ ID NO 358
<211> LENGTH: 7
<212> TYPE: PRT
<213> ORGANISM: Artificial sequence
<220> FEATURE:
<223> OTHER INFORMATION: DJ-1 derived peptide

<400> SEQUENCE: 358

Glu Lys Asp Gly Leu Ile Leu
1               5

<210> SEQ ID NO 359
<211> LENGTH: 7
<212> TYPE: PRT
<213> ORGANISM: Artificial sequence
<220> FEATURE:
<223> OTHER INFORMATION: DJ-1 derived peptide

<400> SEQUENCE: 359

Lys Asp Gly Leu Ile Leu Thr
1               5

<210> SEQ ID NO 360
<211> LENGTH: 7
<212> TYPE: PRT
<213> ORGANISM: Artificial sequence
<220> FEATURE:
<223> OTHER INFORMATION: DJ-1 derived peptide

<400> SEQUENCE: 360

Asp Gly Leu Ile Leu Thr Ser
1               5

<210> SEQ ID NO 361
<211> LENGTH: 7
<212> TYPE: PRT
<213> ORGANISM: Artificial sequence
<220> FEATURE:
<223> OTHER INFORMATION: DJ-1 derived peptide

<400> SEQUENCE: 361

Gly Leu Ile Leu Thr Ser Arg
1               5

<210> SEQ ID NO 362
<211> LENGTH: 7
<212> TYPE: PRT
<213> ORGANISM: Artificial sequence
<220> FEATURE:
<223> OTHER INFORMATION: DJ-1 derived peptide

<400> SEQUENCE: 362

Leu Ile Leu Thr Ser Arg Gly
1               5

<210> SEQ ID NO 363
<211> LENGTH: 7
<212> TYPE: PRT
<213> ORGANISM: Artificial sequence
<220> FEATURE:
<223> OTHER INFORMATION: DJ-1 derived peptide

<400> SEQUENCE: 363

Ile Leu Thr Ser Arg Gly Pro
1               5

<210> SEQ ID NO 364
<211> LENGTH: 7
<212> TYPE: PRT
<213> ORGANISM: Artificial sequence
<220> FEATURE:
<223> OTHER INFORMATION: DJ-1 derived peptide

<400> SEQUENCE: 364

Leu Thr Ser Arg Gly Pro Gly
1               5

<210> SEQ ID NO 365
<211> LENGTH: 7
<212> TYPE: PRT
<213> ORGANISM: Artificial sequence
<220> FEATURE:
<223> OTHER INFORMATION: DJ-1 derived peptide

<400> SEQUENCE: 365

Thr Ser Arg Gly Pro Gly Thr
1               5

<210> SEQ ID NO 366
<211> LENGTH: 7
<212> TYPE: PRT
<213> ORGANISM: Artificial sequence
<220> FEATURE:
<223> OTHER INFORMATION: DJ-1 derived peptide

<400> SEQUENCE: 366

Ser Arg Gly Pro Gly Thr Ser

```
<210> SEQ ID NO 367
<211> LENGTH: 7
<212> TYPE: PRT
<213> ORGANISM: Artificial sequence
<220> FEATURE:
<223> OTHER INFORMATION: DJ-1 derived peptide

<400> SEQUENCE: 367

Arg Gly Pro Gly Thr Ser Phe
1               5

<210> SEQ ID NO 368
<211> LENGTH: 7
<212> TYPE: PRT
<213> ORGANISM: Artificial sequence
<220> FEATURE:
<223> OTHER INFORMATION: DJ-1 derived peptide

<400> SEQUENCE: 368

Gly Pro Gly Thr Ser Phe Glu
1               5

<210> SEQ ID NO 369
<211> LENGTH: 7
<212> TYPE: PRT
<213> ORGANISM: Artificial sequence
<220> FEATURE:
<223> OTHER INFORMATION: DJ-1 derived peptide

<400> SEQUENCE: 369

Pro Gly Thr Ser Phe Glu Phe
1               5

<210> SEQ ID NO 370
<211> LENGTH: 7
<212> TYPE: PRT
<213> ORGANISM: Artificial sequence
<220> FEATURE:
<223> OTHER INFORMATION: DJ-1 derived peptide

<400> SEQUENCE: 370

Gly Thr Ser Phe Glu Phe Ala
1               5

<210> SEQ ID NO 371
<211> LENGTH: 7
<212> TYPE: PRT
<213> ORGANISM: Artificial sequence
<220> FEATURE:
<223> OTHER INFORMATION: DJ-1 derived peptide

<400> SEQUENCE: 371

Thr Ser Phe Glu Phe Ala Leu
1               5

<210> SEQ ID NO 372
<211> LENGTH: 7
<212> TYPE: PRT
<213> ORGANISM: Artificial sequence
<220> FEATURE:
<223> OTHER INFORMATION: DJ-1 derived peptide

<400> SEQUENCE: 372

Ser Phe Glu Phe Ala Leu Ala
1               5
```

<210> SEQ ID NO 373
<211> LENGTH: 7
<212> TYPE: PRT
<213> ORGANISM: Artificial sequence
<220> FEATURE:
<223> OTHER INFORMATION: DJ-1 derived peptide

<400> SEQUENCE: 373

Phe Glu Phe Ala Leu Ala Ile
1               5

<210> SEQ ID NO 374
<211> LENGTH: 7
<212> TYPE: PRT
<213> ORGANISM: Artificial sequence
<220> FEATURE:
<223> OTHER INFORMATION: DJ-1 derived peptide

<400> SEQUENCE: 374

Glu Phe Ala Leu Ala Ile Val
1               5

<210> SEQ ID NO 375
<211> LENGTH: 7
<212> TYPE: PRT
<213> ORGANISM: Artificial sequence
<220> FEATURE:
<223> OTHER INFORMATION: DJ-1 derived peptide

<400> SEQUENCE: 375

Phe Ala Leu Ala Ile Val Glu
1               5

<210> SEQ ID NO 376
<211> LENGTH: 7
<212> TYPE: PRT
<213> ORGANISM: Artificial sequence
<220> FEATURE:
<223> OTHER INFORMATION: DJ-1 derived peptide

<400> SEQUENCE: 376

Ala Leu Ala Ile Val Glu Ala
1               5

<210> SEQ ID NO 377
<211> LENGTH: 7
<212> TYPE: PRT
<213> ORGANISM: Artificial sequence
<220> FEATURE:
<223> OTHER INFORMATION: DJ-1 derived peptide

<400> SEQUENCE: 377

Leu Ala Ile Val Glu Ala Leu
1               5

<210> SEQ ID NO 378
<211> LENGTH: 7
<212> TYPE: PRT
<213> ORGANISM: Artificial sequence
<220> FEATURE:
<223> OTHER INFORMATION: DJ-1 derived peptide

<400> SEQUENCE: 378

Ala Ile Val Glu Ala Leu Asn
1               5

<210> SEQ ID NO 379

```
<211> LENGTH: 7
<212> TYPE: PRT
<213> ORGANISM: Artificial sequence
<220> FEATURE:
<223> OTHER INFORMATION: DJ-1 derived peptide

<400> SEQUENCE: 379

Ile Val Glu Ala Leu Asn Gly
1               5

<210> SEQ ID NO 380
<211> LENGTH: 8
<212> TYPE: PRT
<213> ORGANISM: Artificial sequence
<220> FEATURE:
<223> OTHER INFORMATION: DJ-1 derived peptide

<400> SEQUENCE: 380

Val Glu Lys Asp Gly Leu Ile Leu
1               5

<210> SEQ ID NO 381
<211> LENGTH: 8
<212> TYPE: PRT
<213> ORGANISM: Artificial sequence
<220> FEATURE:
<223> OTHER INFORMATION: DJ-1 derived peptide

<400> SEQUENCE: 381

Glu Lys Asp Gly Leu Ile Leu Thr
1               5

<210> SEQ ID NO 382
<211> LENGTH: 8
<212> TYPE: PRT
<213> ORGANISM: Artificial sequence
<220> FEATURE:
<223> OTHER INFORMATION: DJ-1 derived peptide

<400> SEQUENCE: 382

Lys Asp Gly Leu Ile Leu Thr Ser
1               5

<210> SEQ ID NO 383
<211> LENGTH: 8
<212> TYPE: PRT
<213> ORGANISM: Artificial sequence
<220> FEATURE:
<223> OTHER INFORMATION: DJ-1 derived peptide

<400> SEQUENCE: 383

Asp Gly Leu Ile Leu Thr Ser Arg
1               5

<210> SEQ ID NO 384
<211> LENGTH: 8
<212> TYPE: PRT
<213> ORGANISM: Artificial sequence
<220> FEATURE:
<223> OTHER INFORMATION: DJ-1 derived peptide

<400> SEQUENCE: 384

Gly Leu Ile Leu Thr Ser Arg Gly
1               5

<210> SEQ ID NO 385
<211> LENGTH: 8
<212> TYPE: PRT
```

<213> ORGANISM: Artificial sequence
<220> FEATURE:
<223> OTHER INFORMATION: DJ-1 derived peptide

<400> SEQUENCE: 385

Leu Ile Leu Thr Ser Arg Gly Pro
1               5

<210> SEQ ID NO 386
<211> LENGTH: 8
<212> TYPE: PRT
<213> ORGANISM: Artificial sequence
<220> FEATURE:
<223> OTHER INFORMATION: DJ-1 derived peptide

<400> SEQUENCE: 386

Ile Leu Thr Ser Arg Gly Pro Gly
1               5

<210> SEQ ID NO 387
<211> LENGTH: 8
<212> TYPE: PRT
<213> ORGANISM: Artificial sequence
<220> FEATURE:
<223> OTHER INFORMATION: DJ-1 derived peptide

<400> SEQUENCE: 387

Leu Thr Ser Arg Gly Pro Gly Thr
1               5

<210> SEQ ID NO 388
<211> LENGTH: 8
<212> TYPE: PRT
<213> ORGANISM: Artificial sequence
<220> FEATURE:
<223> OTHER INFORMATION: DJ-1 derived peptide

<400> SEQUENCE: 388

Thr Ser Arg Gly Pro Gly Thr Ser
1               5

<210> SEQ ID NO 389
<211> LENGTH: 8
<212> TYPE: PRT
<213> ORGANISM: Artificial sequence
<220> FEATURE:
<223> OTHER INFORMATION: DJ-1 derived peptide

<400> SEQUENCE: 389

Ser Arg Gly Pro Gly Thr Ser Phe
1               5

<210> SEQ ID NO 390
<211> LENGTH: 8
<212> TYPE: PRT
<213> ORGANISM: Artificial sequence
<220> FEATURE:
<223> OTHER INFORMATION: DJ-1 derived peptide

<400> SEQUENCE: 390

Arg Gly Pro Gly Thr Ser Phe Glu
1               5

<210> SEQ ID NO 391
<211> LENGTH: 8
<212> TYPE: PRT
<213> ORGANISM: Artificial sequence
<220> FEATURE:

<223> OTHER INFORMATION: DJ-1 derived peptide

<400> SEQUENCE: 391

Gly Pro Gly Thr Ser Phe Glu Phe
1               5

<210> SEQ ID NO 392
<211> LENGTH: 8
<212> TYPE: PRT
<213> ORGANISM: Artificial sequence
<220> FEATURE:
<223> OTHER INFORMATION: DJ-1 derived peptide

<400> SEQUENCE: 392

Pro Gly Thr Ser Phe Glu Phe Ala
1               5

<210> SEQ ID NO 393
<211> LENGTH: 8
<212> TYPE: PRT
<213> ORGANISM: Artificial sequence
<220> FEATURE:
<223> OTHER INFORMATION: DJ-1 derived peptide

<400> SEQUENCE: 393

Gly Thr Ser Phe Glu Phe Ala Leu
1               5

<210> SEQ ID NO 394
<211> LENGTH: 8
<212> TYPE: PRT
<213> ORGANISM: Artificial sequence
<220> FEATURE:
<223> OTHER INFORMATION: DJ-1 derived peptide

<400> SEQUENCE: 394

Thr Ser Phe Glu Phe Ala Leu Ala
1               5

<210> SEQ ID NO 395
<211> LENGTH: 8
<212> TYPE: PRT
<213> ORGANISM: Artificial sequence
<220> FEATURE:
<223> OTHER INFORMATION: DJ-1 derived peptide

<400> SEQUENCE: 395

Ser Phe Glu Phe Ala Leu Ala Ile
1               5

<210> SEQ ID NO 396
<211> LENGTH: 8
<212> TYPE: PRT
<213> ORGANISM: Artificial sequence
<220> FEATURE:
<223> OTHER INFORMATION: DJ-1 derived peptide

<400> SEQUENCE: 396

Phe Glu Phe Ala Leu Ala Ile Val
1               5

<210> SEQ ID NO 397
<211> LENGTH: 8
<212> TYPE: PRT
<213> ORGANISM: Artificial sequence
<220> FEATURE:
<223> OTHER INFORMATION: DJ-1 derived peptide

```
<400> SEQUENCE: 397

Glu Phe Ala Leu Ala Ile Val Glu
1               5

<210> SEQ ID NO 398
<211> LENGTH: 8
<212> TYPE: PRT
<213> ORGANISM: Artificial sequence
<220> FEATURE:
<223> OTHER INFORMATION: DJ-1 derived peptide

<400> SEQUENCE: 398

Phe Ala Leu Ala Ile Val Glu Ala
1               5

<210> SEQ ID NO 399
<211> LENGTH: 8
<212> TYPE: PRT
<213> ORGANISM: Artificial sequence
<220> FEATURE:
<223> OTHER INFORMATION: DJ-1 derived peptide

<400> SEQUENCE: 399

Ala Leu Ala Ile Val Glu Ala Leu
1               5

<210> SEQ ID NO 400
<211> LENGTH: 8
<212> TYPE: PRT
<213> ORGANISM: Artificial sequence
<220> FEATURE:
<223> OTHER INFORMATION: DJ-1 derived peptide

<400> SEQUENCE: 400

Leu Ala Ile Val Glu Ala Leu Asn
1               5

<210> SEQ ID NO 401
<211> LENGTH: 8
<212> TYPE: PRT
<213> ORGANISM: Artificial sequence
<220> FEATURE:
<223> OTHER INFORMATION: DJ-1 derived peptide

<400> SEQUENCE: 401

Ala Ile Val Glu Ala Leu Asn Gly
1               5

<210> SEQ ID NO 402
<211> LENGTH: 9
<212> TYPE: PRT
<213> ORGANISM: Artificial sequence
<220> FEATURE:
<223> OTHER INFORMATION: DJ-1 derived peptide

<400> SEQUENCE: 402

Val Glu Lys Asp Gly Leu Ile Leu Thr
1               5

<210> SEQ ID NO 403
<211> LENGTH: 9
<212> TYPE: PRT
<213> ORGANISM: Artificial sequence
<220> FEATURE:
<223> OTHER INFORMATION: DJ-1 derived peptide

<400> SEQUENCE: 403
```

```
Glu Lys Asp Gly Leu Ile Leu Thr Ser
1               5
```

<210> SEQ ID NO 404
<211> LENGTH: 9
<212> TYPE: PRT
<213> ORGANISM: Artificial sequence
<220> FEATURE:
<223> OTHER INFORMATION: DJ-1 derived peptide

<400> SEQUENCE: 404

```
Lys Asp Gly Leu Ile Leu Thr Ser Arg
1               5
```

<210> SEQ ID NO 405
<211> LENGTH: 9
<212> TYPE: PRT
<213> ORGANISM: Artificial sequence
<220> FEATURE:
<223> OTHER INFORMATION: DJ-1 derived peptide

<400> SEQUENCE: 405

```
Asp Gly Leu Ile Leu Thr Ser Arg Gly
1               5
```

<210> SEQ ID NO 406
<211> LENGTH: 9
<212> TYPE: PRT
<213> ORGANISM: Artificial sequence
<220> FEATURE:
<223> OTHER INFORMATION: DJ-1 derived peptide

<400> SEQUENCE: 406

```
Gly Leu Ile Leu Thr Ser Arg Gly Pro
1               5
```

<210> SEQ ID NO 407
<211> LENGTH: 9
<212> TYPE: PRT
<213> ORGANISM: Artificial sequence
<220> FEATURE:
<223> OTHER INFORMATION: DJ-1 derived peptide

<400> SEQUENCE: 407

```
Leu Ile Leu Thr Ser Arg Gly Pro Gly
1               5
```

<210> SEQ ID NO 408
<211> LENGTH: 9
<212> TYPE: PRT
<213> ORGANISM: Artificial sequence
<220> FEATURE:
<223> OTHER INFORMATION: DJ-1 derived peptide

<400> SEQUENCE: 408

```
Ile Leu Thr Ser Arg Gly Pro Gly Thr
1               5
```

<210> SEQ ID NO 409
<211> LENGTH: 9
<212> TYPE: PRT
<213> ORGANISM: Artificial sequence
<220> FEATURE:
<223> OTHER INFORMATION: DJ-1 derived peptide

<400> SEQUENCE: 409

```
Leu Thr Ser Arg Gly Pro Gly Thr Ser
1               5
```

```
<210> SEQ ID NO 410
<211> LENGTH: 9
<212> TYPE: PRT
<213> ORGANISM: Artificial sequence
<220> FEATURE:
<223> OTHER INFORMATION: DJ-1 derived peptide

<400> SEQUENCE: 410

Thr Ser Arg Gly Pro Gly Thr Ser Phe
1               5

<210> SEQ ID NO 411
<211> LENGTH: 9
<212> TYPE: PRT
<213> ORGANISM: Artificial sequence
<220> FEATURE:
<223> OTHER INFORMATION: DJ-1 derived peptide

<400> SEQUENCE: 411

Ser Arg Gly Pro Gly Thr Ser Phe Glu
1               5

<210> SEQ ID NO 412
<211> LENGTH: 9
<212> TYPE: PRT
<213> ORGANISM: Artificial sequence
<220> FEATURE:
<223> OTHER INFORMATION: DJ-1 derived peptide

<400> SEQUENCE: 412

Arg Gly Pro Gly Thr Ser Phe Glu Phe
1               5

<210> SEQ ID NO 413
<211> LENGTH: 9
<212> TYPE: PRT
<213> ORGANISM: Artificial sequence
<220> FEATURE:
<223> OTHER INFORMATION: DJ-1 derived peptide

<400> SEQUENCE: 413

Gly Pro Gly Thr Ser Phe Glu Phe Ala
1               5

<210> SEQ ID NO 414
<211> LENGTH: 9
<212> TYPE: PRT
<213> ORGANISM: Artificial sequence
<220> FEATURE:
<223> OTHER INFORMATION: DJ-1 derived peptide

<400> SEQUENCE: 414

Pro Gly Thr Ser Phe Glu Phe Ala Leu
1               5

<210> SEQ ID NO 415
<211> LENGTH: 9
<212> TYPE: PRT
<213> ORGANISM: Artificial sequence
<220> FEATURE:
<223> OTHER INFORMATION: DJ-1 derived peptide

<400> SEQUENCE: 415

Gly Thr Ser Phe Glu Phe Ala Leu Ala
1               5
```

```
<210> SEQ ID NO 416
<211> LENGTH: 9
<212> TYPE: PRT
<213> ORGANISM: Artificial sequence
<220> FEATURE:
<223> OTHER INFORMATION: DJ-1 derived peptide

<400> SEQUENCE: 416

Thr Ser Phe Glu Phe Ala Leu Ala Ile
1               5

<210> SEQ ID NO 417
<211> LENGTH: 9
<212> TYPE: PRT
<213> ORGANISM: Artificial sequence
<220> FEATURE:
<223> OTHER INFORMATION: DJ-1 derived peptide

<400> SEQUENCE: 417

Ser Phe Glu Phe Ala Leu Ala Ile Val
1               5

<210> SEQ ID NO 418
<211> LENGTH: 9
<212> TYPE: PRT
<213> ORGANISM: Artificial sequence
<220> FEATURE:
<223> OTHER INFORMATION: DJ-1 derived peptide

<400> SEQUENCE: 418

Phe Glu Phe Ala Leu Ala Ile Val Glu
1               5

<210> SEQ ID NO 419
<211> LENGTH: 9
<212> TYPE: PRT
<213> ORGANISM: Artificial sequence
<220> FEATURE:
<223> OTHER INFORMATION: DJ-1 derived peptide

<400> SEQUENCE: 419

Glu Phe Ala Leu Ala Ile Val Glu Ala
1               5

<210> SEQ ID NO 420
<211> LENGTH: 9
<212> TYPE: PRT
<213> ORGANISM: Artificial sequence
<220> FEATURE:
<223> OTHER INFORMATION: DJ-1 derived peptide

<400> SEQUENCE: 420

Phe Ala Leu Ala Ile Val Glu Ala Leu
1               5

<210> SEQ ID NO 421
<211> LENGTH: 9
<212> TYPE: PRT
<213> ORGANISM: Artificial sequence
<220> FEATURE:
<223> OTHER INFORMATION: DJ-1 derived peptide

<400> SEQUENCE: 421

Ala Leu Ala Ile Val Glu Ala Leu Asn
1               5

<210> SEQ ID NO 422
<211> LENGTH: 9
```

```
<212> TYPE: PRT
<213> ORGANISM: Artificial sequence
<220> FEATURE:
<223> OTHER INFORMATION: DJ-1 derived peptide

<400> SEQUENCE: 422

Leu Ala Ile Val Glu Ala Leu Asn Gly
1               5

<210> SEQ ID NO 423
<211> LENGTH: 10
<212> TYPE: PRT
<213> ORGANISM: Artificial sequence
<220> FEATURE:
<223> OTHER INFORMATION: DJ-1 derived peptide

<400> SEQUENCE: 423

Val Glu Lys Asp Gly Leu Ile Leu Thr Ser
1               5                   10

<210> SEQ ID NO 424
<211> LENGTH: 10
<212> TYPE: PRT
<213> ORGANISM: Artificial sequence
<220> FEATURE:
<223> OTHER INFORMATION: DJ-1 derived peptide

<400> SEQUENCE: 424

Glu Lys Asp Gly Leu Ile Leu Thr Ser Arg
1               5                   10

<210> SEQ ID NO 425
<211> LENGTH: 10
<212> TYPE: PRT
<213> ORGANISM: Artificial sequence
<220> FEATURE:
<223> OTHER INFORMATION: DJ-1 derived peptide

<400> SEQUENCE: 425

Lys Asp Gly Leu Ile Leu Thr Ser Arg Gly
1               5                   10

<210> SEQ ID NO 426
<211> LENGTH: 10
<212> TYPE: PRT
<213> ORGANISM: Artificial sequence
<220> FEATURE:
<223> OTHER INFORMATION: DJ-1 derived peptide

<400> SEQUENCE: 426

Asp Gly Leu Ile Leu Thr Ser Arg Gly Pro
1               5                   10

<210> SEQ ID NO 427
<211> LENGTH: 10
<212> TYPE: PRT
<213> ORGANISM: Artificial sequence
<220> FEATURE:
<223> OTHER INFORMATION: DJ-1 derived peptide

<400> SEQUENCE: 427

Gly Leu Ile Leu Thr Ser Arg Gly Pro Gly
1               5                   10

<210> SEQ ID NO 428
<211> LENGTH: 10
<212> TYPE: PRT
<213> ORGANISM: Artificial sequence
```

<220> FEATURE:
<223> OTHER INFORMATION: DJ-1 derived peptide

<400> SEQUENCE: 428

Leu Ile Leu Thr Ser Arg Gly Pro Gly Thr
1               5                   10

<210> SEQ ID NO 429
<211> LENGTH: 10
<212> TYPE: PRT
<213> ORGANISM: Artificial sequence
<220> FEATURE:
<223> OTHER INFORMATION: DJ-1 derived peptide

<400> SEQUENCE: 429

Ile Leu Thr Ser Arg Gly Pro Gly Thr Ser
1               5                   10

<210> SEQ ID NO 430
<211> LENGTH: 10
<212> TYPE: PRT
<213> ORGANISM: Artificial sequence
<220> FEATURE:
<223> OTHER INFORMATION: DJ-1 derived peptide

<400> SEQUENCE: 430

Leu Thr Ser Arg Gly Pro Gly Thr Ser Phe
1               5                   10

<210> SEQ ID NO 431
<211> LENGTH: 10
<212> TYPE: PRT
<213> ORGANISM: Artificial sequence
<220> FEATURE:
<223> OTHER INFORMATION: DJ-1 derived peptide

<400> SEQUENCE: 431

Thr Ser Arg Gly Pro Gly Thr Ser Phe Glu
1               5                   10

<210> SEQ ID NO 432
<211> LENGTH: 10
<212> TYPE: PRT
<213> ORGANISM: Artificial sequence
<220> FEATURE:
<223> OTHER INFORMATION: DJ-1 derived peptide

<400> SEQUENCE: 432

Ser Arg Gly Pro Gly Thr Ser Phe Glu Phe
1               5                   10

<210> SEQ ID NO 433
<211> LENGTH: 10
<212> TYPE: PRT
<213> ORGANISM: Artificial sequence
<220> FEATURE:
<223> OTHER INFORMATION: DJ-1 derived peptide

<400> SEQUENCE: 433

Arg Gly Pro Gly Thr Ser Phe Glu Phe Ala
1               5                   10

<210> SEQ ID NO 434
<211> LENGTH: 10
<212> TYPE: PRT
<213> ORGANISM: Artificial sequence
<220> FEATURE:
<223> OTHER INFORMATION: DJ-1 derived peptide

```
<400> SEQUENCE: 434

Gly Pro Gly Thr Ser Phe Glu Phe Ala Leu
1               5                   10

<210> SEQ ID NO 435
<211> LENGTH: 10
<212> TYPE: PRT
<213> ORGANISM: Artificial sequence
<220> FEATURE:
<223> OTHER INFORMATION: DJ-1 derived peptide

<400> SEQUENCE: 435

Pro Gly Thr Ser Phe Glu Phe Ala Leu Ala
1               5                   10

<210> SEQ ID NO 436
<211> LENGTH: 10
<212> TYPE: PRT
<213> ORGANISM: Artificial sequence
<220> FEATURE:
<223> OTHER INFORMATION: DJ-1 derived peptide

<400> SEQUENCE: 436

Gly Thr Ser Phe Glu Phe Ala Leu Ala Ile
1               5                   10

<210> SEQ ID NO 437
<211> LENGTH: 10
<212> TYPE: PRT
<213> ORGANISM: Artificial sequence
<220> FEATURE:
<223> OTHER INFORMATION: DJ-1 derived peptide

<400> SEQUENCE: 437

Thr Ser Phe Glu Phe Ala Leu Ala Ile Val
1               5                   10

<210> SEQ ID NO 438
<211> LENGTH: 10
<212> TYPE: PRT
<213> ORGANISM: Artificial sequence
<220> FEATURE:
<223> OTHER INFORMATION: DJ-1 derived peptide

<400> SEQUENCE: 438

Ser Phe Glu Phe Ala Leu Ala Ile Val Glu
1               5                   10

<210> SEQ ID NO 439
<211> LENGTH: 10
<212> TYPE: PRT
<213> ORGANISM: Artificial sequence
<220> FEATURE:
<223> OTHER INFORMATION: DJ-1 derived peptide

<400> SEQUENCE: 439

Phe Glu Phe Ala Leu Ala Ile Val Glu Ala
1               5                   10

<210> SEQ ID NO 440
<211> LENGTH: 10
<212> TYPE: PRT
<213> ORGANISM: Artificial sequence
<220> FEATURE:
<223> OTHER INFORMATION: DJ-1 derived peptide

<400> SEQUENCE: 440
```

```
Glu Phe Ala Leu Ala Ile Val Glu Ala Leu
1               5                   10

<210> SEQ ID NO 441
<211> LENGTH: 10
<212> TYPE: PRT
<213> ORGANISM: Artificial sequence
<220> FEATURE:
<223> OTHER INFORMATION: DJ-1 derived peptide

<400> SEQUENCE: 441

Phe Ala Leu Ala Ile Val Glu Ala Leu Asn
1               5                   10

<210> SEQ ID NO 442
<211> LENGTH: 10
<212> TYPE: PRT
<213> ORGANISM: Artificial sequence
<220> FEATURE:
<223> OTHER INFORMATION: DJ-1 derived peptide

<400> SEQUENCE: 442

Ala Leu Ala Ile Val Glu Ala Leu Asn Gly
1               5                   10

<210> SEQ ID NO 443
<211> LENGTH: 11
<212> TYPE: PRT
<213> ORGANISM: Artificial sequence
<220> FEATURE:
<223> OTHER INFORMATION: DJ-1 derived peptide

<400> SEQUENCE: 443

Val Glu Lys Asp Gly Leu Ile Leu Thr Ser Arg
1               5                   10

<210> SEQ ID NO 444
<211> LENGTH: 11
<212> TYPE: PRT
<213> ORGANISM: Artificial sequence
<220> FEATURE:
<223> OTHER INFORMATION: DJ-1 derived peptide

<400> SEQUENCE: 444

Glu Lys Asp Gly Leu Ile Leu Thr Ser Arg Gly
1               5                   10

<210> SEQ ID NO 445
<211> LENGTH: 11
<212> TYPE: PRT
<213> ORGANISM: Artificial sequence
<220> FEATURE:
<223> OTHER INFORMATION: DJ-1 derived peptide

<400> SEQUENCE: 445

Lys Asp Gly Leu Ile Leu Thr Ser Arg Gly Pro
1               5                   10

<210> SEQ ID NO 446
<211> LENGTH: 11
<212> TYPE: PRT
<213> ORGANISM: Artificial sequence
<220> FEATURE:
<223> OTHER INFORMATION: DJ-1 derived peptide

<400> SEQUENCE: 446

Asp Gly Leu Ile Leu Thr Ser Arg Gly Pro Gly
```

```
                1               5                   10

<210> SEQ ID NO 447
<211> LENGTH: 11
<212> TYPE: PRT
<213> ORGANISM: Artificial sequence
<220> FEATURE:
<223> OTHER INFORMATION: DJ-1 derived peptide

<400> SEQUENCE: 447

Gly Leu Ile Leu Thr Ser Arg Gly Pro Gly Thr
1               5                   10

<210> SEQ ID NO 448
<211> LENGTH: 11
<212> TYPE: PRT
<213> ORGANISM: Artificial sequence
<220> FEATURE:
<223> OTHER INFORMATION: DJ-1 derived peptide

<400> SEQUENCE: 448

Leu Ile Leu Thr Ser Arg Gly Pro Gly Thr Ser
1               5                   10

<210> SEQ ID NO 449
<211> LENGTH: 11
<212> TYPE: PRT
<213> ORGANISM: Artificial sequence
<220> FEATURE:
<223> OTHER INFORMATION: DJ-1 derived peptide

<400> SEQUENCE: 449

Ile Leu Thr Ser Arg Gly Pro Gly Thr Ser Phe
1               5                   10

<210> SEQ ID NO 450
<211> LENGTH: 11
<212> TYPE: PRT
<213> ORGANISM: Artificial sequence
<220> FEATURE:
<223> OTHER INFORMATION: DJ-1 derived peptide

<400> SEQUENCE: 450

Leu Thr Ser Arg Gly Pro Gly Thr Ser Phe Glu
1               5                   10

<210> SEQ ID NO 451
<211> LENGTH: 11
<212> TYPE: PRT
<213> ORGANISM: Artificial sequence
<220> FEATURE:
<223> OTHER INFORMATION: DJ-1 derived peptide

<400> SEQUENCE: 451

Thr Ser Arg Gly Pro Gly Thr Ser Phe Glu Phe
1               5                   10

<210> SEQ ID NO 452
<211> LENGTH: 11
<212> TYPE: PRT
<213> ORGANISM: Artificial sequence
<220> FEATURE:
<223> OTHER INFORMATION: DJ-1 derived peptide

<400> SEQUENCE: 452

Ser Arg Gly Pro Gly Thr Ser Phe Glu Phe Ala
1               5                   10
```

<210> SEQ ID NO 453
<211> LENGTH: 11
<212> TYPE: PRT
<213> ORGANISM: Artificial sequence
<220> FEATURE:
<223> OTHER INFORMATION: DJ-1 derived peptide

<400> SEQUENCE: 453

Arg Gly Pro Gly Thr Ser Phe Glu Phe Ala Leu
1               5                   10

<210> SEQ ID NO 454
<211> LENGTH: 11
<212> TYPE: PRT
<213> ORGANISM: Artificial sequence
<220> FEATURE:
<223> OTHER INFORMATION: DJ-1 derived peptide

<400> SEQUENCE: 454

Gly Pro Gly Thr Ser Phe Glu Phe Ala Leu Ala
1               5                   10

<210> SEQ ID NO 455
<211> LENGTH: 11
<212> TYPE: PRT
<213> ORGANISM: Artificial sequence
<220> FEATURE:
<223> OTHER INFORMATION: DJ-1 derived peptide

<400> SEQUENCE: 455

Pro Gly Thr Ser Phe Glu Phe Ala Leu Ala Ile
1               5                   10

<210> SEQ ID NO 456
<211> LENGTH: 11
<212> TYPE: PRT
<213> ORGANISM: Artificial sequence
<220> FEATURE:
<223> OTHER INFORMATION: DJ-1 derived peptide

<400> SEQUENCE: 456

Gly Thr Ser Phe Glu Phe Ala Leu Ala Ile Val
1               5                   10

<210> SEQ ID NO 457
<211> LENGTH: 11
<212> TYPE: PRT
<213> ORGANISM: Artificial sequence
<220> FEATURE:
<223> OTHER INFORMATION: DJ-1 derived peptide

<400> SEQUENCE: 457

Thr Ser Phe Glu Phe Ala Leu Ala Ile Val Glu
1               5                   10

<210> SEQ ID NO 458
<211> LENGTH: 11
<212> TYPE: PRT
<213> ORGANISM: Artificial sequence
<220> FEATURE:
<223> OTHER INFORMATION: DJ-1 derived peptide

<400> SEQUENCE: 458

Ser Phe Glu Phe Ala Leu Ala Ile Val Glu Ala
1               5                   10

<210> SEQ ID NO 459

-continued

```
<211> LENGTH: 11
<212> TYPE: PRT
<213> ORGANISM: Artificial sequence
<220> FEATURE:
<223> OTHER INFORMATION: DJ-1 derived peptide

<400> SEQUENCE: 459

Phe Glu Phe Ala Leu Ala Ile Val Glu Ala Leu
1               5                   10

<210> SEQ ID NO 460
<211> LENGTH: 11
<212> TYPE: PRT
<213> ORGANISM: Artificial sequence
<220> FEATURE:
<223> OTHER INFORMATION: DJ-1 derived peptide

<400> SEQUENCE: 460

Glu Phe Ala Leu Ala Ile Val Glu Ala Leu Asn
1               5                   10

<210> SEQ ID NO 461
<211> LENGTH: 11
<212> TYPE: PRT
<213> ORGANISM: Artificial sequence
<220> FEATURE:
<223> OTHER INFORMATION: DJ-1 derived peptide

<400> SEQUENCE: 461

Phe Ala Leu Ala Ile Val Glu Ala Leu Asn Gly
1               5                   10

<210> SEQ ID NO 462
<211> LENGTH: 12
<212> TYPE: PRT
<213> ORGANISM: Artificial sequence
<220> FEATURE:
<223> OTHER INFORMATION: DJ-1 derived peptide

<400> SEQUENCE: 462

Val Glu Lys Asp Gly Leu Ile Leu Thr Ser Arg Gly
1               5                   10

<210> SEQ ID NO 463
<211> LENGTH: 12
<212> TYPE: PRT
<213> ORGANISM: Artificial sequence
<220> FEATURE:
<223> OTHER INFORMATION: DJ-1 derived peptide

<400> SEQUENCE: 463

Glu Lys Asp Gly Leu Ile Leu Thr Ser Arg Gly Pro
1               5                   10

<210> SEQ ID NO 464
<211> LENGTH: 12
<212> TYPE: PRT
<213> ORGANISM: Artificial sequence
<220> FEATURE:
<223> OTHER INFORMATION: DJ-1 derived peptide

<400> SEQUENCE: 464

Lys Asp Gly Leu Ile Leu Thr Ser Arg Gly Pro Gly
1               5                   10

<210> SEQ ID NO 465
<211> LENGTH: 12
<212> TYPE: PRT
```

```
<213> ORGANISM: Artificial sequence
<220> FEATURE:
<223> OTHER INFORMATION: DJ-1 derived peptide

<400> SEQUENCE: 465

Asp Gly Leu Ile Leu Thr Ser Arg Gly Pro Gly Thr
1               5                   10

<210> SEQ ID NO 466
<211> LENGTH: 12
<212> TYPE: PRT
<213> ORGANISM: Artificial sequence
<220> FEATURE:
<223> OTHER INFORMATION: DJ-1 derived peptide

<400> SEQUENCE: 466

Gly Leu Ile Leu Thr Ser Arg Gly Pro Gly Thr Ser
1               5                   10

<210> SEQ ID NO 467
<211> LENGTH: 12
<212> TYPE: PRT
<213> ORGANISM: Artificial sequence
<220> FEATURE:
<223> OTHER INFORMATION: DJ-1 derived peptide

<400> SEQUENCE: 467

Leu Ile Leu Thr Ser Arg Gly Pro Gly Thr Ser Phe
1               5                   10

<210> SEQ ID NO 468
<211> LENGTH: 12
<212> TYPE: PRT
<213> ORGANISM: Artificial sequence
<220> FEATURE:
<223> OTHER INFORMATION: DJ-1 derived peptide

<400> SEQUENCE: 468

Ile Leu Thr Ser Arg Gly Pro Gly Thr Ser Phe Glu
1               5                   10

<210> SEQ ID NO 469
<211> LENGTH: 12
<212> TYPE: PRT
<213> ORGANISM: Artificial sequence
<220> FEATURE:
<223> OTHER INFORMATION: DJ-1 derived peptide

<400> SEQUENCE: 469

Leu Thr Ser Arg Gly Pro Gly Thr Ser Phe Glu Phe
1               5                   10

<210> SEQ ID NO 470
<211> LENGTH: 12
<212> TYPE: PRT
<213> ORGANISM: Artificial sequence
<220> FEATURE:
<223> OTHER INFORMATION: DJ-1 derived peptide

<400> SEQUENCE: 470

Thr Ser Arg Gly Pro Gly Thr Ser Phe Glu Phe Ala
1               5                   10

<210> SEQ ID NO 471
<211> LENGTH: 12
<212> TYPE: PRT
<213> ORGANISM: Artificial sequence
<220> FEATURE:
```

<223> OTHER INFORMATION: DJ-1 derived peptide

<400> SEQUENCE: 471

Ser Arg Gly Pro Gly Thr Ser Phe Glu Phe Ala Leu
1               5                   10

<210> SEQ ID NO 472
<211> LENGTH: 12
<212> TYPE: PRT
<213> ORGANISM: Artificial sequence
<220> FEATURE:
<223> OTHER INFORMATION: DJ-1 derived peptide

<400> SEQUENCE: 472

Arg Gly Pro Gly Thr Ser Phe Glu Phe Ala Leu Ala
1               5                   10

<210> SEQ ID NO 473
<211> LENGTH: 12
<212> TYPE: PRT
<213> ORGANISM: Artificial sequence
<220> FEATURE:
<223> OTHER INFORMATION: DJ-1 derived peptide

<400> SEQUENCE: 473

Gly Pro Gly Thr Ser Phe Glu Phe Ala Leu Ala Ile
1               5                   10

<210> SEQ ID NO 474
<211> LENGTH: 12
<212> TYPE: PRT
<213> ORGANISM: Artificial sequence
<220> FEATURE:
<223> OTHER INFORMATION: DJ-1 derived peptide

<400> SEQUENCE: 474

Pro Gly Thr Ser Phe Glu Phe Ala Leu Ala Ile Val
1               5                   10

<210> SEQ ID NO 475
<211> LENGTH: 12
<212> TYPE: PRT
<213> ORGANISM: Artificial sequence
<220> FEATURE:
<223> OTHER INFORMATION: DJ-1 derived peptide

<400> SEQUENCE: 475

Gly Thr Ser Phe Glu Phe Ala Leu Ala Ile Val Glu
1               5                   10

<210> SEQ ID NO 476
<211> LENGTH: 12
<212> TYPE: PRT
<213> ORGANISM: Artificial sequence
<220> FEATURE:
<223> OTHER INFORMATION: DJ-1 derived peptide

<400> SEQUENCE: 476

Thr Ser Phe Glu Phe Ala Leu Ala Ile Val Glu Ala
1               5                   10

<210> SEQ ID NO 477
<211> LENGTH: 12
<212> TYPE: PRT
<213> ORGANISM: Artificial sequence
<220> FEATURE:
<223> OTHER INFORMATION: DJ-1 derived peptide

```
<400> SEQUENCE: 477

Ser Phe Glu Phe Ala Leu Ala Ile Val Glu Ala Leu
1               5                   10

<210> SEQ ID NO 478
<211> LENGTH: 12
<212> TYPE: PRT
<213> ORGANISM: Artificial sequence
<220> FEATURE:
<223> OTHER INFORMATION: DJ-1 derived peptide

<400> SEQUENCE: 478

Phe Glu Phe Ala Leu Ala Ile Val Glu Ala Leu Asn
1               5                   10

<210> SEQ ID NO 479
<211> LENGTH: 12
<212> TYPE: PRT
<213> ORGANISM: Artificial sequence
<220> FEATURE:
<223> OTHER INFORMATION: DJ-1 derived peptide

<400> SEQUENCE: 479

Glu Phe Ala Leu Ala Ile Val Glu Ala Leu Asn Gly
1               5                   10

<210> SEQ ID NO 480
<211> LENGTH: 13
<212> TYPE: PRT
<213> ORGANISM: Artificial sequence
<220> FEATURE:
<223> OTHER INFORMATION: DJ-1 derived peptide

<400> SEQUENCE: 480

Val Glu Lys Asp Gly Leu Ile Leu Thr Ser Arg Gly Pro
1               5                   10

<210> SEQ ID NO 481
<211> LENGTH: 13
<212> TYPE: PRT
<213> ORGANISM: Artificial sequence
<220> FEATURE:
<223> OTHER INFORMATION: DJ-1 derived peptide

<400> SEQUENCE: 481

Glu Lys Asp Gly Leu Ile Leu Thr Ser Arg Gly Pro Gly
1               5                   10

<210> SEQ ID NO 482
<211> LENGTH: 13
<212> TYPE: PRT
<213> ORGANISM: Artificial sequence
<220> FEATURE:
<223> OTHER INFORMATION: DJ-1 derived peptide

<400> SEQUENCE: 482

Lys Asp Gly Leu Ile Leu Thr Ser Arg Gly Pro Gly Thr
1               5                   10

<210> SEQ ID NO 483
<211> LENGTH: 13
<212> TYPE: PRT
<213> ORGANISM: Artificial sequence
<220> FEATURE:
<223> OTHER INFORMATION: DJ-1 derived peptide

<400> SEQUENCE: 483
```

```
Asp Gly Leu Ile Leu Thr Ser Arg Gly Pro Gly Thr Ser
1               5                   10
```

<210> SEQ ID NO 484
<211> LENGTH: 13
<212> TYPE: PRT
<213> ORGANISM: Artificial sequence
<220> FEATURE:
<223> OTHER INFORMATION: DJ-1 derived peptide

<400> SEQUENCE: 484

```
Gly Leu Ile Leu Thr Ser Arg Gly Pro Gly Thr Ser Phe
1               5                   10
```

<210> SEQ ID NO 485
<211> LENGTH: 13
<212> TYPE: PRT
<213> ORGANISM: Artificial sequence
<220> FEATURE:
<223> OTHER INFORMATION: DJ-1 derived peptide

<400> SEQUENCE: 485

```
Leu Ile Leu Thr Ser Arg Gly Pro Gly Thr Ser Phe Glu
1               5                   10
```

<210> SEQ ID NO 486
<211> LENGTH: 13
<212> TYPE: PRT
<213> ORGANISM: Artificial sequence
<220> FEATURE:
<223> OTHER INFORMATION: DJ-1 derived peptide

<400> SEQUENCE: 486

```
Ile Leu Thr Ser Arg Gly Pro Gly Thr Ser Phe Glu Phe
1               5                   10
```

<210> SEQ ID NO 487
<211> LENGTH: 13
<212> TYPE: PRT
<213> ORGANISM: Artificial sequence
<220> FEATURE:
<223> OTHER INFORMATION: DJ-1 derived peptide

<400> SEQUENCE: 487

```
Leu Thr Ser Arg Gly Pro Gly Thr Ser Phe Glu Phe Ala
1               5                   10
```

<210> SEQ ID NO 488
<211> LENGTH: 13
<212> TYPE: PRT
<213> ORGANISM: Artificial sequence
<220> FEATURE:
<223> OTHER INFORMATION: DJ-1 derived peptide

<400> SEQUENCE: 488

```
Thr Ser Arg Gly Pro Gly Thr Ser Phe Glu Phe Ala Leu
1               5                   10
```

<210> SEQ ID NO 489
<211> LENGTH: 13
<212> TYPE: PRT
<213> ORGANISM: Artificial sequence
<220> FEATURE:
<223> OTHER INFORMATION: DJ-1 derived peptide

<400> SEQUENCE: 489

```
Ser Arg Gly Pro Gly Thr Ser Phe Glu Phe Ala Leu Ala
1               5                   10
```

```
<210> SEQ ID NO 490
<211> LENGTH: 13
<212> TYPE: PRT
<213> ORGANISM: Artificial sequence
<220> FEATURE:
<223> OTHER INFORMATION: DJ-1 derived peptide

<400> SEQUENCE: 490

Arg Gly Pro Gly Thr Ser Phe Glu Phe Ala Leu Ala Ile
 1               5                  10

<210> SEQ ID NO 491
<211> LENGTH: 13
<212> TYPE: PRT
<213> ORGANISM: Artificial sequence
<220> FEATURE:
<223> OTHER INFORMATION: DJ-1 derived peptide

<400> SEQUENCE: 491

Gly Pro Gly Thr Ser Phe Glu Phe Ala Leu Ala Ile Val
 1               5                  10

<210> SEQ ID NO 492
<211> LENGTH: 13
<212> TYPE: PRT
<213> ORGANISM: Artificial sequence
<220> FEATURE:
<223> OTHER INFORMATION: DJ-1 derived peptide

<400> SEQUENCE: 492

Pro Gly Thr Ser Phe Glu Phe Ala Leu Ala Ile Val Glu
 1               5                  10

<210> SEQ ID NO 493
<211> LENGTH: 13
<212> TYPE: PRT
<213> ORGANISM: Artificial sequence
<220> FEATURE:
<223> OTHER INFORMATION: DJ-1 derived peptide

<400> SEQUENCE: 493

Gly Thr Ser Phe Glu Phe Ala Leu Ala Ile Val Glu Ala
 1               5                  10

<210> SEQ ID NO 494
<211> LENGTH: 13
<212> TYPE: PRT
<213> ORGANISM: Artificial sequence
<220> FEATURE:
<223> OTHER INFORMATION: DJ-1 derived peptide

<400> SEQUENCE: 494

Thr Ser Phe Glu Phe Ala Leu Ala Ile Val Glu Ala Leu
 1               5                  10

<210> SEQ ID NO 495
<211> LENGTH: 13
<212> TYPE: PRT
<213> ORGANISM: Artificial sequence
<220> FEATURE:
<223> OTHER INFORMATION: DJ-1 derived peptide

<400> SEQUENCE: 495

Ser Phe Glu Phe Ala Leu Ala Ile Val Glu Ala Leu Asn
 1               5                  10
```

```
<210> SEQ ID NO 496
<211> LENGTH: 13
<212> TYPE: PRT
<213> ORGANISM: Artificial sequence
<220> FEATURE:
<223> OTHER INFORMATION: DJ-1 derived peptide

<400> SEQUENCE: 496

Phe Glu Phe Ala Leu Ala Ile Val Glu Ala Leu Asn Gly
1               5                   10

<210> SEQ ID NO 497
<211> LENGTH: 14
<212> TYPE: PRT
<213> ORGANISM: Artificial sequence
<220> FEATURE:
<223> OTHER INFORMATION: DJ-1 derived peptide

<400> SEQUENCE: 497

Val Glu Lys Asp Gly Leu Ile Leu Thr Ser Arg Gly Pro Gly
1               5                   10

<210> SEQ ID NO 498
<211> LENGTH: 14
<212> TYPE: PRT
<213> ORGANISM: Artificial sequence
<220> FEATURE:
<223> OTHER INFORMATION: DJ-1 derived peptide

<400> SEQUENCE: 498

Glu Lys Asp Gly Leu Ile Leu Thr Ser Arg Gly Pro Gly Thr
1               5                   10

<210> SEQ ID NO 499
<211> LENGTH: 14
<212> TYPE: PRT
<213> ORGANISM: Artificial sequence
<220> FEATURE:
<223> OTHER INFORMATION: DJ-1 derived peptide

<400> SEQUENCE: 499

Lys Asp Gly Leu Ile Leu Thr Ser Arg Gly Pro Gly Thr Ser
1               5                   10

<210> SEQ ID NO 500
<211> LENGTH: 14
<212> TYPE: PRT
<213> ORGANISM: Artificial sequence
<220> FEATURE:
<223> OTHER INFORMATION: DJ-1 derived peptide

<400> SEQUENCE: 500

Asp Gly Leu Ile Leu Thr Ser Arg Gly Pro Gly Thr Ser Phe
1               5                   10

<210> SEQ ID NO 501
<211> LENGTH: 14
<212> TYPE: PRT
<213> ORGANISM: Artificial sequence
<220> FEATURE:
<223> OTHER INFORMATION: DJ-1 derived peptide

<400> SEQUENCE: 501

Gly Leu Ile Leu Thr Ser Arg Gly Pro Gly Thr Ser Phe Glu
1               5                   10

<210> SEQ ID NO 502
<211> LENGTH: 14
```

```
<212> TYPE: PRT
<213> ORGANISM: Artificial sequence
<220> FEATURE:
<223> OTHER INFORMATION: DJ-1 derived peptide

<400> SEQUENCE: 502

Leu Ile Leu Thr Ser Arg Gly Pro Gly Thr Ser Phe Glu Phe
1               5                   10

<210> SEQ ID NO 503
<211> LENGTH: 14
<212> TYPE: PRT
<213> ORGANISM: Artificial sequence
<220> FEATURE:
<223> OTHER INFORMATION: DJ-1 derived peptide

<400> SEQUENCE: 503

Ile Leu Thr Ser Arg Gly Pro Gly Thr Ser Phe Glu Phe Ala
1               5                   10

<210> SEQ ID NO 504
<211> LENGTH: 14
<212> TYPE: PRT
<213> ORGANISM: Artificial sequence
<220> FEATURE:
<223> OTHER INFORMATION: DJ-1 derived peptide

<400> SEQUENCE: 504

Leu Thr Ser Arg Gly Pro Gly Thr Ser Phe Glu Phe Ala Leu
1               5                   10

<210> SEQ ID NO 505
<211> LENGTH: 14
<212> TYPE: PRT
<213> ORGANISM: Artificial sequence
<220> FEATURE:
<223> OTHER INFORMATION: DJ-1 derived peptide

<400> SEQUENCE: 505

Thr Ser Arg Gly Pro Gly Thr Ser Phe Glu Phe Ala Leu Ala
1               5                   10

<210> SEQ ID NO 506
<211> LENGTH: 14
<212> TYPE: PRT
<213> ORGANISM: Artificial sequence
<220> FEATURE:
<223> OTHER INFORMATION: DJ-1 derived peptide

<400> SEQUENCE: 506

Ser Arg Gly Pro Gly Thr Ser Phe Glu Phe Ala Leu Ala Ile
1               5                   10

<210> SEQ ID NO 507
<211> LENGTH: 14
<212> TYPE: PRT
<213> ORGANISM: Artificial sequence
<220> FEATURE:
<223> OTHER INFORMATION: DJ-1 derived peptide

<400> SEQUENCE: 507

Arg Gly Pro Gly Thr Ser Phe Glu Phe Ala Leu Ala Ile Val
1               5                   10

<210> SEQ ID NO 508
<211> LENGTH: 14
<212> TYPE: PRT
<213> ORGANISM: Artificial sequence
```

```
<220> FEATURE:
<223> OTHER INFORMATION: DJ-1 derived peptide

<400> SEQUENCE: 508

Gly Pro Gly Thr Ser Phe Glu Phe Ala Leu Ala Ile Val Glu
1               5                   10

<210> SEQ ID NO 509
<211> LENGTH: 14
<212> TYPE: PRT
<213> ORGANISM: Artificial sequence
<220> FEATURE:
<223> OTHER INFORMATION: DJ-1 derived peptide

<400> SEQUENCE: 509

Pro Gly Thr Ser Phe Glu Phe Ala Leu Ala Ile Val Glu Ala
1               5                   10

<210> SEQ ID NO 510
<211> LENGTH: 14
<212> TYPE: PRT
<213> ORGANISM: Artificial sequence
<220> FEATURE:
<223> OTHER INFORMATION: DJ-1 derived peptide

<400> SEQUENCE: 510

Gly Thr Ser Phe Glu Phe Ala Leu Ala Ile Val Glu Ala Leu
1               5                   10

<210> SEQ ID NO 511
<211> LENGTH: 14
<212> TYPE: PRT
<213> ORGANISM: Artificial sequence
<220> FEATURE:
<223> OTHER INFORMATION: DJ-1 derived peptide

<400> SEQUENCE: 511

Thr Ser Phe Glu Phe Ala Leu Ala Ile Val Glu Ala Leu Asn
1               5                   10

<210> SEQ ID NO 512
<211> LENGTH: 14
<212> TYPE: PRT
<213> ORGANISM: Artificial sequence
<220> FEATURE:
<223> OTHER INFORMATION: DJ-1 derived peptide

<400> SEQUENCE: 512

Ser Phe Glu Phe Ala Leu Ala Ile Val Glu Ala Leu Asn Gly
1               5                   10

<210> SEQ ID NO 513
<211> LENGTH: 15
<212> TYPE: PRT
<213> ORGANISM: Artificial sequence
<220> FEATURE:
<223> OTHER INFORMATION: DJ-1 derived peptide

<400> SEQUENCE: 513

Val Glu Lys Asp Gly Leu Ile Leu Thr Ser Arg Gly Pro Gly Thr
1               5                   10                  15

<210> SEQ ID NO 514
<211> LENGTH: 15
<212> TYPE: PRT
<213> ORGANISM: Artificial sequence
<220> FEATURE:
<223> OTHER INFORMATION: DJ-1 derived peptide
```

-continued

```
<400> SEQUENCE: 514

Glu Lys Asp Gly Leu Ile Leu Thr Ser Arg Gly Pro Gly Thr Ser
1               5                   10                  15

<210> SEQ ID NO 515
<211> LENGTH: 15
<212> TYPE: PRT
<213> ORGANISM: Artificial sequence
<220> FEATURE:
<223> OTHER INFORMATION: DJ-1 derived peptide

<400> SEQUENCE: 515

Lys Asp Gly Leu Ile Leu Thr Ser Arg Gly Pro Gly Thr Ser Phe
1               5                   10                  15

<210> SEQ ID NO 516
<211> LENGTH: 15
<212> TYPE: PRT
<213> ORGANISM: Artificial sequence
<220> FEATURE:
<223> OTHER INFORMATION: DJ-1 derived peptide

<400> SEQUENCE: 516

Asp Gly Leu Ile Leu Thr Ser Arg Gly Pro Gly Thr Ser Phe Glu
1               5                   10                  15

<210> SEQ ID NO 517
<211> LENGTH: 15
<212> TYPE: PRT
<213> ORGANISM: Artificial sequence
<220> FEATURE:
<223> OTHER INFORMATION: DJ-1 derived peptide

<400> SEQUENCE: 517

Gly Leu Ile Leu Thr Ser Arg Gly Pro Gly Thr Ser Phe Glu Phe
1               5                   10                  15

<210> SEQ ID NO 518
<211> LENGTH: 15
<212> TYPE: PRT
<213> ORGANISM: Artificial sequence
<220> FEATURE:
<223> OTHER INFORMATION: DJ-1 derived peptide

<400> SEQUENCE: 518

Leu Ile Leu Thr Ser Arg Gly Pro Gly Thr Ser Phe Glu Phe Ala
1               5                   10                  15

<210> SEQ ID NO 519
<211> LENGTH: 15
<212> TYPE: PRT
<213> ORGANISM: Artificial sequence
<220> FEATURE:
<223> OTHER INFORMATION: DJ-1 derived peptide

<400> SEQUENCE: 519

Ile Leu Thr Ser Arg Gly Pro Gly Thr Ser Phe Glu Phe Ala Leu
1               5                   10                  15

<210> SEQ ID NO 520
<211> LENGTH: 15
<212> TYPE: PRT
<213> ORGANISM: Artificial sequence
<220> FEATURE:
<223> OTHER INFORMATION: DJ-1 derived peptide

<400> SEQUENCE: 520
```

Leu Thr Ser Arg Gly Pro Gly Thr Ser Phe Glu Phe Ala Leu Ala
1               5                   10                  15

<210> SEQ ID NO 521
<211> LENGTH: 15
<212> TYPE: PRT
<213> ORGANISM: Artificial sequence
<220> FEATURE:
<223> OTHER INFORMATION: DJ-1 derived peptide

<400> SEQUENCE: 521

Thr Ser Arg Gly Pro Gly Thr Ser Phe Glu Phe Ala Leu Ala Ile
1               5                   10                  15

<210> SEQ ID NO 522
<211> LENGTH: 15
<212> TYPE: PRT
<213> ORGANISM: Artificial sequence
<220> FEATURE:
<223> OTHER INFORMATION: DJ-1 derived peptide

<400> SEQUENCE: 522

Ser Arg Gly Pro Gly Thr Ser Phe Glu Phe Ala Leu Ala Ile Val
1               5                   10                  15

<210> SEQ ID NO 523
<211> LENGTH: 15
<212> TYPE: PRT
<213> ORGANISM: Artificial sequence
<220> FEATURE:
<223> OTHER INFORMATION: DJ-1 derived peptide

<400> SEQUENCE: 523

Arg Gly Pro Gly Thr Ser Phe Glu Phe Ala Leu Ala Ile Val Glu
1               5                   10                  15

<210> SEQ ID NO 524
<211> LENGTH: 15
<212> TYPE: PRT
<213> ORGANISM: Artificial sequence
<220> FEATURE:
<223> OTHER INFORMATION: DJ-1 derived peptide

<400> SEQUENCE: 524

Gly Pro Gly Thr Ser Phe Glu Phe Ala Leu Ala Ile Val Glu Ala
1               5                   10                  15

<210> SEQ ID NO 525
<211> LENGTH: 15
<212> TYPE: PRT
<213> ORGANISM: Artificial sequence
<220> FEATURE:
<223> OTHER INFORMATION: DJ-1 derived peptide

<400> SEQUENCE: 525

Pro Gly Thr Ser Phe Glu Phe Ala Leu Ala Ile Val Glu Ala Leu
1               5                   10                  15

<210> SEQ ID NO 526
<211> LENGTH: 15
<212> TYPE: PRT
<213> ORGANISM: Artificial sequence
<220> FEATURE:
<223> OTHER INFORMATION: DJ-1 derived peptide

<400> SEQUENCE: 526

Gly Thr Ser Phe Glu Phe Ala Leu Ala Ile Val Glu Ala Leu Asn

-continued

```
<210> SEQ ID NO 527
<211> LENGTH: 15
<212> TYPE: PRT
<213> ORGANISM: Artificial sequence
<220> FEATURE:
<223> OTHER INFORMATION: DJ-1 derived peptide

<400> SEQUENCE: 527

Thr Ser Phe Glu Phe Ala Leu Ala Ile Val Glu Ala Leu Asn Gly
1               5                   10                  15

<210> SEQ ID NO 528
<211> LENGTH: 189
<212> TYPE: PRT
<213> ORGANISM: Homo sapiens

<400> SEQUENCE: 528

Met Ala Ser Lys Arg Ala Leu Val Ile Leu Ala Lys Gly Ala Glu Glu
1               5                   10                  15

Met Glu Thr Val Ile Pro Val Asp Val Met Arg Arg Ala Gly Ile Lys
            20                  25                  30

Val Thr Val Ala Gly Leu Ala Gly Lys Asp Pro Val Gln Cys Ser Arg
        35                  40                  45

Asp Val Val Ile Cys Pro Asp Ala Ser Leu Glu Asp Ala Lys Lys Glu
    50                  55                  60

Gly Pro Tyr Asp Val Val Val Leu Pro Gly Gly Asn Leu Gly Ala Gln
65                  70                  75                  80

Asn Leu Ser Glu Ser Ala Ala Val Lys Glu Ile Leu Lys Glu Gln Glu
                85                  90                  95

Asn Arg Lys Gly Leu Ile Ala Ala Ile Cys Ala Gly Pro Thr Ala Leu
            100                 105                 110

Leu Ala His Glu Ile Gly Cys Gly Ser Lys Val Thr Thr His Pro Leu
        115                 120                 125

Ala Lys Asp Lys Met Met Asn Gly Gly His Tyr Thr Tyr Ser Glu Asn
    130                 135                 140

Arg Val Glu Lys Asp Gly Leu Ile Leu Thr Ser Arg Gly Pro Gly Thr
145                 150                 155                 160

Ser Phe Glu Phe Ala Leu Ala Ile Val Glu Ala Leu Asn Gly Lys Glu
                165                 170                 175

Val Ala Ala Gln Val Lys Ala Pro Leu Val Leu Lys Asp
            180                 185
```

US 8,378,070 B2

PEPTIDES FOR THE REGULATION OF NEUROTRANSMITTER SEQUESTRATION AND RELEASE

RELATED APPLICATIONS

This application is a National Phase Application of PCT Patent Application No. PCT/IL2008/000336 having International Filing Date of Mar. 12, 2008, which claims priority from US Provisional Patent Application No. 60/906,226, filed on Mar. 12, 2007. The contents of the above Applications are all incorporated herein by reference.

FIELD AND BACKGROUND OF THE INVENTION

The present invention relates to novel agents such as peptides useful in the treatment of neurodegenerative disorders.

Parkinson's disease (PD) is a multifactorial disease caused by both genetic and environmental factors. Although most patients suffering from PD have a sporadic disease, several genetic causes have been identified in recent years. An increasing number of genes that cause inherited forms of PD have provided the opportunity for new insights into the mechanisms at the basis of the disease. These genes include alpha-synuclein, parkin, PINK1, dardarin (LRRK2), and DJ-1.

DJ-1 deletions and point mutations have been found worldwide, and loss of functional protein was shown to cause autosomal recessive PD. DJ-1 encodes a small 189 amino acid protein that is ubiquitously expressed and highly conserved throughout diverse species. DJ-1 is widely distributed and is highly expressed in the brain and extra cerebral tissues. The high expression of DJ-1 in the central nervous system (CNS) is not confined to a single anatomical or functional system. Within the substantia nigra, however, DJ-1 is localized in both neuronal and glial cells, suggesting a distinct role in this area.

Accumulating data suggests that DJ-1 plays an important role in the oxidative stress response, but the exact mechanism of action is unknown [Kim, 2005, Proc. Natl. Acad. Sci. USA. 102, 5215-5220; Choi, 2006, J. Biol. Chem. 281, 10816-10824]. DJ-1 has several isoforms with different isoelectric points (pl). This pl shift is caused by the oxidation of cysteine and methionine residues in DJ-1. Post-mortem studies of brain samples taken from PD patients found that the acidic isoforms of DJ-1 are more abundant in PD brains as compared to controls [Choi, 2006, J. Biol. Chem. 281, 10816-10824]. Elevated levels of DJ-1 were recently reported in the cerebrospinal fluid (CSF) of sporadic PD patients [Waragai, 2006, Biochem. Biophys. Res. Commun. 345, 967-972]. These studies imply that DJ-1 has a role not only in selective inherited cases but also in the more common sporadic disease.

Dopamine is a highly toxic molecule. Neurotoxicity due to elevated cytosolic dopamine has long been implicated in etiology of neurodegeneration in PD. Dopaminergic neurons protect themselves from dopamine toxicity by its concentration within intracytoplasmic vesicles. Vesicular monoamine transporters (VMATs) mediate accumulation of monoamines such as serotonin, dopamine, adrenaline, noradrenaline, and histamine from the cytoplasm into storage organelles. There are two isoforms of VMATs identified in humans: VMAT1 and VMAT2, which are also members of the solute carrier family 18 (SLC18A1 and SLC18A2, respectively). These proteins share 60% sequence identity; however, they demonstrate a range of differences in their physiologic and pharmacologic properties. VMAT1 is expressed primarily in neuroendocrine cells such as the adrenal medulla and pineal gland, while VMAT2 is expressed in all aminergic neurons in the mammalian CNS. The vesicular monoamine transporter-2 (VMAT2) transfers dopamine from the cytoplasm into these synaptic vesicles, thereby controlling intraneuronal sequestration of dopamine, preventing its cytoplasmic oxidation and preparing it for the exocytotic quantal release.

Biogenic amines play critical roles in consciousness, mood, thought, motivation, cognition, perception, and autonomic responses. Alterations in genes encoding VMATs might play an important role in the pathogenesis of neuropsychiatric diseases including bipolar disease, depression, addiction and schizophrenia (Richards, 2006). VMAT2 is a site of action of important drugs such as reserpine and tetrabenazine, both of which inhibit vesicular amine transport. Reserpine is a useful drug in the treatment of hypertension and schizophrenia; however, high dosages of reserpine frequently produce a syndrome resembling depressive disorder. The monoamine theory is one of the major hypotheses about the biological etiology of major depressive disorders. Recent pharmacological and postmortem investigations suggest that depressed patients have alterations in function of serotonergic neuronal system. Elevated levels of VMAT2 have been reported in the brain of bipolar disorder patients and in platelet of untreated depressed patients. It is speculated that altered VMAT2 expression in depressed patients results from a compensatory mechanism to overcome a monoaminergic deficit. Several lines of evidence suggest the involvement of the VMAT in the psychostimulant action of amphetamines which induce monoamine efflux from vesicles.

U.S. Pat. Appl. No. 20060153807 teaches administration of DJ-1 and peptides thereof for the treatment of neurodegenerative diseases such as Parkinson's.

SUMMARY OF THE INVENTION

According to an aspect of some embodiments of the present invention there is provided a method of selecting an agent comprising a neuroprotecting activity, the method comprising:

(a) introducing a plurality of agents into a plurality of cells;

(b) analyzing Vesicular Monoamine Transporter 2 (VMAT2) transcription in the cells; and (c) identifying an agent of the plurality of agents capable of up-regulating DJ-1-dependent VMAT2 transcription in the cells, thereby selecting the agent comprising the neuroprotecting activity.

According to an aspect of some embodiments of the present invention there is provided an agent identified according to the method of the present invention.

According to an aspect of some embodiments of the present invention there is provided an isolated peptide or peptide mimetic thereof, comprising an amino acid sequence which regulates VMAT2 transcription, the peptide being no more than 30 amino acids in length.

According to an aspect of some embodiments of the present invention there is provided an isolated peptide comprising at least one of the amino acid sequences as set forth in SEQ ID NOs: 1-6.

According to an aspect of some embodiments of the present invention there is provided an isolated polynucleotide comprising a nucleic acid sequence encoding the peptide identified according to the method of the present invention.

According to an aspect of some embodiments of the present invention there is provided an isolated polynucleotide comprising a nucleic acid sequence encoding a peptide comprising an amino acid sequence which regulates VMAT2 transcription, the peptide being no more than 30 amino acids in length.

According to an aspect of some embodiments of the present invention there is provided a method of treating a neurodegenerative disorder, the method comprising administering to an individual in need thereof a therapeutically effective amount of the isolated peptides of the present invention, thereby treating the neurodegenerative disorder.

According to an aspect of some embodiments of the present invention there is provided a method of treating a neurodegenerative disorder, the method comprising administering to an individual in need thereof a therapeutically effective amount of the isolated polynucleotides of the present invention, thereby treating the neurodegenerative disorder.

According to an aspect of some embodiments of the present invention there is provided a method of increasing viability of neuronal cells, the method comprising contacting the neuronal cells with an agent selected according to the method of the present invention, thereby increasing viability of the neuronal cells.

According to an aspect of some embodiments of the present invention there is provided a method of selecting an agent comprising a neurotoxic activity, the method comprising:
  (a) introducing agents into a cell;
  (b) analyzing Vesicular Monoamine Transporter 2 (VMAT2) transcription in the cell; and
  (c) identifying the agent capable of down-regulating DJ-1-dependent VMAT2 transcription in the cell, thereby selecting the agent comprising the neurotoxic activity.

According to an aspect of some embodiments of the present invention there is provided a method of decreasing viability of neuronal cells, the method comprising contacting the neuronal cells with an agent selected according to the method of the present invention, thereby decreasing viability of the neuronal cells.

According to some embodiments of the invention, the agent is a peptide agent.

According to some embodiments of the invention, the agent is a small molecule.

According to some embodiments of the invention, the peptide agent comprises a DJ-1 sequence.

According to some embodiments of the invention, the cell is a neuronal cell.

According to some embodiments of the invention, the neuronal cell is a neuroblastoma cell.

According to some embodiments of the invention, the analyzing is effected by determining an interaction between the agent and a promoter region of a Vesicular Monoamine Transporter 2 (VMAT2) polynucleotide.

According to some embodiments of the invention, the analyzing is effected by a transcription assay.

According to some embodiments of the invention, the transcription assay is a reporter based assay.

According to some embodiments of the invention, the promoter region of VMAT2 is endogenous to the cell.

According to some embodiments of the invention, the promoter region of VMAT2 is exogenous to the cell.

According to some embodiments of the invention, the promoter region is transcriptionally linked to a detectable polypeptide.

According to some embodiments of the invention, the agent is a peptide agent.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

FIGS. 1A-B are bar graphs illustrating that vulnerability to dopamine toxicity and accumulation of intracellular reactive oxygen species (ROS) depend on DJ-1 expression levels. FIG. 1A: Exposure to increasing dopamine concentrations (0-500 uM, for 24 hours) causes dose dependent cell death, as evaluated by MTT viability assay. Overexpression of DJ-1 conferred resistance to dopamine while decreasing DJ-1 levels by siRNA led to increased vulnerability to dopamine. Cell viability (%) is expressed as percentage of surviving cells compared with that in non-treated control. Data presented as means±s.d. * indicates viability versus no treatment, $p<0.05$. Each experiment was repeated 3 times in triplicates. FIG. 1B: Dopamine exposure leads to increased intracellular ROS, as quantified by the DCF assay. Decreased DJ-1 expression by siRNA for DJ-1 led to increased dopamine-induced intracellular ROS. Overexpression of DJ-1 led to a decreased intracellular ROS. Data presented as means±s.d., * $p<0.001$ (ROS induced by dopamine versus no treatment). † LSD $p<0.001$ (dopamine-induced ROS in DJ-1 overexpression or siRNA for DJ-1 as compared to naïve neuroblastoma). Each experiment was repeated 3 times in triplicates.

Figure 2A:
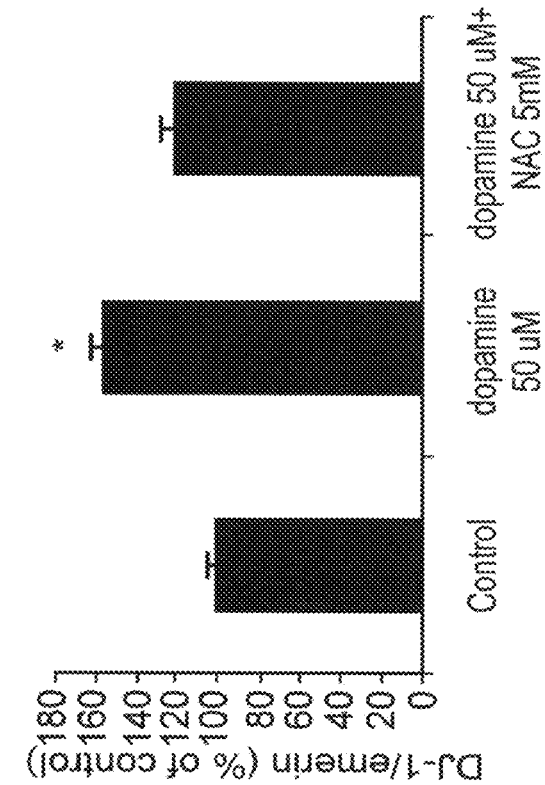
Figure 2B:
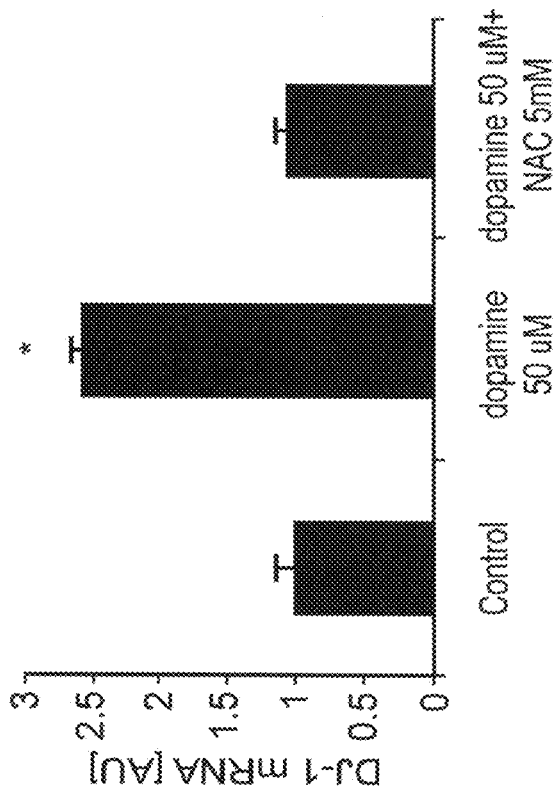

FIGS. 2A-B are bar graphs illustrating that dopamine exposure leads to rapid upregulation of DJ-1 in naïve neuroblastoma SH-SY5Y cells, which was abolished by treatment with the antioxidant N-acetyl cysteine (NAC). FIG. 2A: Exposure of naive neuroblastoma to dopamine induced upregulation of DJ-1 mRNA within 1 hour. Pre-treatment with NAC abolished DJ-1 mRNA upregulation. Data presented as means±s.d., * $p<0.001$. FIG. 2B: Western blot of total cell lysates from naïve neuroblastoma cells demonstrates upregulation of DJ-1 protein levels after dopamine exposure. The experiment was repeated 3 times with similar results.

FIGS. 3A-E are bar graphs and photomicrographs illustrating that overexpression of DJ-1 markedly increases VMAT2 expression levels while siRNA for DJ-1 leads to decreased VMAT2 expression. FIG. 3A: VMAT2 mRNA levels. Overexpression of DJ-1 led to upregulation of VMAT2 mRNA (p=0.0001), while siRNA for DJ-1 led to decreased VMAT2 expression levels (p=0.001). Real time quantitative PCR was repeated 3 times, in triplicates. FIG. 3B: VMAT2 protein expression levels in naïve neuroblastoma cells, overexpressing DJ-1 cells, and siRNA for DJ-1 expressing cells as quantified by Western blotting. FIGS. 3C-E: Representative images of naïve neuroblastoma SH-SY5Y cells (FIG. 3C), DJ-1 overexpressing cells (FIG. 3D), and siRNA for DJ-1 expressing cells (FIG. 3E) immunocytochemically stained for VMAT2 (red). Nuclei were counterstained with the DNA-binding dye DAPI (blue). All images were taken in the same exposure times. Experiments were repeated 3 times in duplicates.

FIGS. 4A-D are bar graphs and photographs illustrating that DJ-1 up regulates VMAT2 expression and function. FIG. 4A: Dopamine exposure leads to upregulation of DJ-1 mRNA within 1 hour. FIG. 4B: Upregulation of VMAT2 mRNA 7 hours following dopamine exposure. Data presented as means±s.d. * p<0.05; ** p<0.01. FIG. 4C: Chromatin immunoprecipitation demonstrating binding of DJ-1 to VMAT2 promotor. Enhanced binding of DJ-1 to VMAT2 promotor is induced by dopamine exposure. Input, 3% of total DNA before IP; IP, done using antibodies specifically recognising DJ-1; non specific Ab, species-matched control antibodies used as negative controls. FIG. 4D: Overexpression of DJ-1 increased KClinduced dopamine release from the synaptic vesicles, while decreased DJ-1 by led to reduced dopamine release. The experiment was repeated 3 times in triplicates. Data presented as means±s.d. * p<0.001; ** p=0.003 versus naïve neuroblastoma cells.

Figure 5:
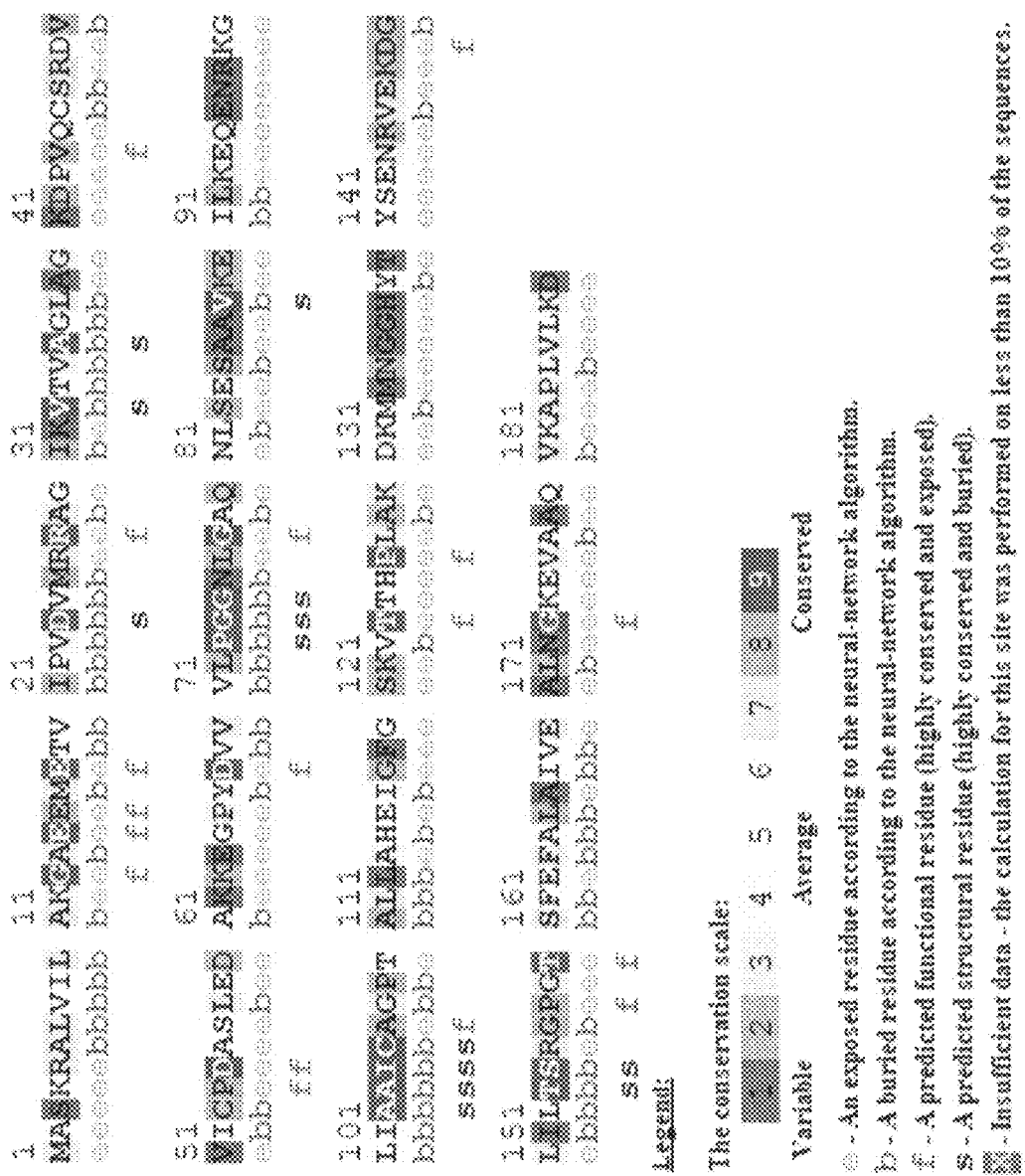

FIG. 5 is an example of a bioinformatics analysis of the DJ-1 polypeptide (SEQ ID NO: 528) as analyzed by ConSeq™.

FIG. 6 is a schematic illustration of the proposed mechanism of DJ-1 protection from dopamine toxicity.

FIGS. 7A-B are bar graphs illustrating the expression level of DJ-1. Overexpression of DJ-1 was effected by stable transfection, and reduced DJ-1 levels were effected by transfection with siRNA for DJ-1. Expression levels of DJ-1 were demonstrated by quantifying mRNA levels (using quantitative Real time PCR (FIG. 7A) as well as protein levels (using Western blot, FIG. 7B). Error bars indicate mean±s.d. * p<0.001. Cells overexpressing DJ-1 increased the DJ-1 mRNA and protein levels over 3-fold, while siRNA for DJ-1 led to reduced DJ-1 expression to 40% of basal levels. These cells had similar growth rates and maintained normal morphological features similar to naïve neuroblastoma SHSY5Y cells.

FIGS. 8A-B are bar graphs illustrating that DJ-1 overexpression protects against dopaminergic toxins such as rotenone (FIG. 8A) and 6-hydroxydopamine (FIG. 8B). Error bars indicate mean±s.d. * p<0.05.

Figures 9A, 9B:
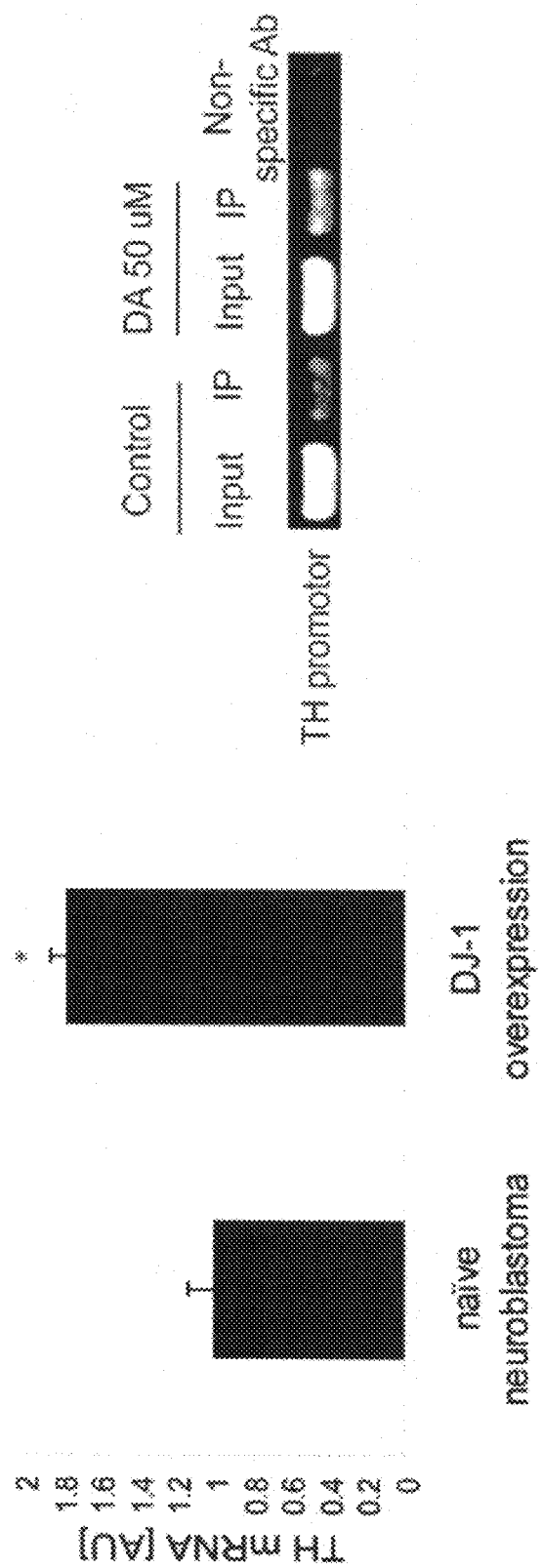

FIGS. 9A-B illustrate that DJ-1 up-regulates tyrosine hydroxylase (TH) expression and function. FIG. 9A: Chromatin immunoprecipitation (ChIP) demonstrating binding of DJ-1 to TH promotor. Dopamine exposure leads to enhanced binding of DJ-1 to TH promotor. Input, 3% of total DNA before ChIP; ChIP, done using antibodies specifically recognising DJ-1; non specific Ab, species-matched control antibodies used as negative controls. FIG. 9B: TH mRNA levels quantified by real time PCR. Overexpression of DJ-1 leads to upregulation of TH mRNA. GAPDH was used as reference gene. Real time quantitative PCR was repeated 3 times, in triplicates.

Figures 10A, 10B, 10C:
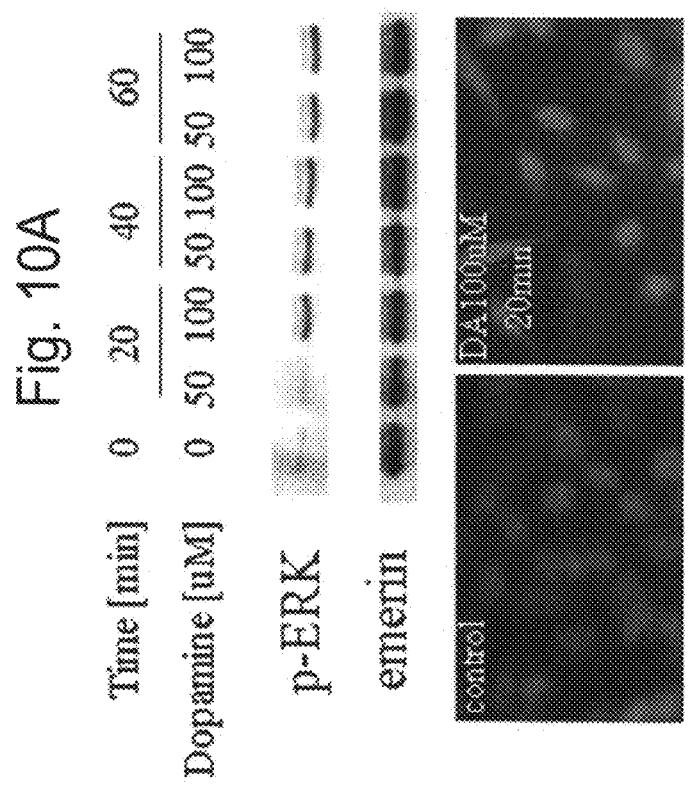
Figures 10D, 10E:
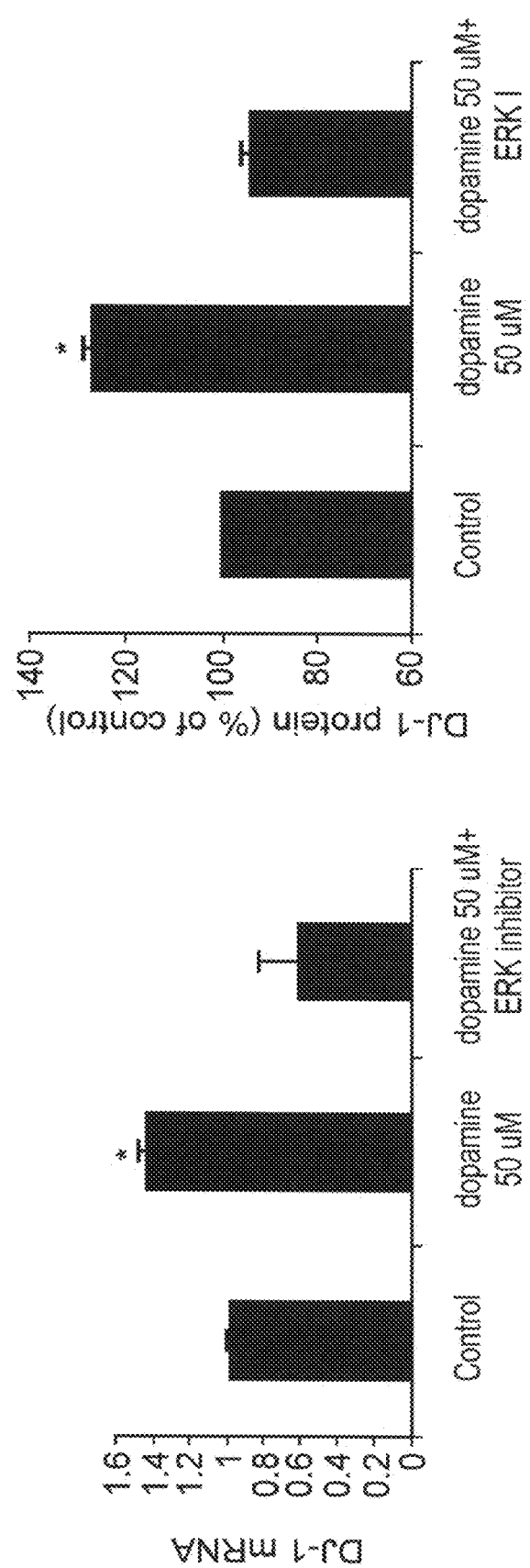

FIGS. 10A-E are photographs and graphs illustrating that dopamine exposure leads to the upregulation of DJ-1 in naïve neuroblastoma SH-SY5Y cells, which is mediated by phosphorylation of ERK 1,2. Exposure of naive neuroblastoma to dopamine induces phosphorylation of ERK 1,2 within 20-60 minutes as illustrated by Western blotting (FIG. 10A) and immunocytochemistry (FIG. 10C). FIG. 10D: Inhibition of ERK1,2 phosphorylation using PD98059 inhibited DJ-1 mRNA upregulation induced by dopamine. Real time quantitative PCR was repeated 3 times, in triplicate. Data are presented as means±s.d. FIG. 10E: Western blot analysis demonstrated that the inhibition of ERK1,2 phosphorylation using PD98059 abolished DJ-1 protein upregulation induced by dopamine. Data are presented as means±s.d. of three independent experiments.

FIGS. 11A-B are bar graphs illustrating that in vivo 6-hydroxydopamine intrastriatal injection leads to ERK1,2 phosphorylation and elevation of DJ-1 and VMAT2 protein levels. FIG. 11A: Unilateral (right) in vivo 6-hydroxydopamine intrastriatal injection leads to the elevation of DJ-1 and VMAT2 protein levels, as evaluated by Western blotting. Data presented as means±s.d. * p<0.05 versus the unlesioned striatum. FIG. 11B: In vivo striatal injection of 6-hydroxydopamine leads to rapid phosphorylation of ERK 1,2 as evaluated by Western blotting. Data presented as means±s.d. * p<0.05 versus the unlesioned striatum.

DESCRIPTION OF THE PREFERRED EMBODIMENTS

The present invention is of a method of identifying novel neuroprotective DJ-1 derived peptide agents based on the capability thereof of regulating VMAT.

Specifically, the peptides identified using this novel screening method can be used to treat a myriad of neurodegenerative diseases and protect against neurodamaging toxins.

The principles and operation of the methods according to the present invention may be better understood with reference to the drawings and accompanying descriptions.

Before explaining at least one embodiment of the invention in detail, it is to be understood that the invention is not limited in its application to the details set forth in the following description or exemplified by the Examples. The invention is capable of other embodiments or of being practiced or carried out in various ways. Also, it is to be understood that the phraseology and terminology employed herein is for the purpose of description and should not be regarded as limiting.

The present inventors have identified a novel mechanism by which DJ-1 enhances neuroprotection in the brain. Specifically, the present inventors have uncovered that ROS, generated by free cytoplasmic dopamine, leads to rapid upregulation of DJ-1, which in turn protectively augments the sequestration of dopamine into the synaptic vesicles through transcriptional upregulation of VMAT2.

The present inventors showed that exposure of human neuroblastoma cells to dopamine led to rapid upregulation of DJ-1, which was mediated through increased intracellular ROS. DJ-1 upregulation was followed by upregulation of VMAT2 expression. Using chromatin immunoprecipitation assay the present inventors demonstrated that DJ-1 is a transcriptional regulator that activates VMAT2 at the genomic level. Overexpression of DJ-1 increased cell resistance to dopamine toxicity, reduced intracellular reactive oxygen species (ROS), and markedly increased VMAT2 expression and function.

Thus, according to one aspect of the present invention, there is provided a method of selecting an agent comprising a neuroprotecting activity, the method comprising:

(a) introducing a plurality of agents into a plurality of cells; and (b) analyzing Vesicular Monoamine Transporter 2 (VMAT2) transcription; and identifying an agent of the plurality of agents capable of up-regulating DJ-1-dependent VMAT2 transcription, thereby selecting the agent comprising the neuroprotecting activity.

The phrase "neuroprotecting activity", as used herein, refers to an activity which inhibits, prevents, ameliorates or reduces the severity of the dysfunction, degeneration or death of nerve cells, axons or their supporting cells in the central nervous system of a mammal, including a human.

The term "VMAT2", as used herein, refers to the polypeptide, or part of the peptide that transports dopamine from the cytoplasm into the synaptic vesicles, thereby controlling intraneuronal sequestration of dopamine. An exemplary VMAT2 is set forth e.g. in Genbank Accession No. NM_003054.

As used herein, the term "DJ-1" refers to the polypeptide as set forth in GenBank Accession No: AB073864 (SEQ ID NO: 528), and derivatives and homologues thereof.

As used herein, the phrase "DJ-1 dependent VMAT2 transcription" refers to the transcription of VMAT2 which requires the presence of a functional DJ-1. The present inventors, using chromatin precipitation, have shown that DJ-1 interacts with the VMAT2 promoter. Without being bound to theory the present inventors postulate that DJ-1 may up-regulate transcription either by binding directly to the promoter region or alternatively by binding to another polypeptide which is capable of binding to the VMAT2 promoter region.

Agents that are able to up-regulate DJ-1 dependent transcription of VMAT2 include agents that increase the activity (i.e. transcriptional activity) or amount of endogenous DJ-1 and also agents that are able to mimic (i.e. compete with) DJ-1' s ability to enhance VMAT2 transcription (i.e. DJ-1 agonists).

Any type of agent may be identified according to the method of the present invention, including but not limited to polynucleotide agents and polypeptide agents. Candidate agents encompass numerous chemical classes, such as organic molecules, e.g. small organic compounds having a molecular weight of more than 50 and less than about 2,500 daltons. Candidate agents typically comprise functional groups necessary for structural interaction with proteins, particularly hydrogen bonding, and typically include at least an amine, carbonyl, hydroxyl or carboxyl group, preferably at least two of the functional chemical groups. The candidate agents often comprise cyclical carbon or heterocyclic structures and/or aromatic or polyaromatic structures substituted with one or more of the above functional groups. Candidate agents are also found among biomolecules including, but not limited to: peptides, saccharides, fatty acids, steroids, pheromones, purines, pyrimidines, derivatives, structural analogs or combinations thereof.

Candidate agents may be obtained from a wide variety of sources including libraries of synthetic or natural compounds. For example, numerous means are available for random and directed synthesis of a wide variety of organic compounds and biomolecules, including expression of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc., to produce structural analogs.

According to one embodiment, the agent that is capable of up-regulating DJ-1 dependent transcription is a peptide agent. An exemplary agent of the present invention is one that comprises a DJ-1 sequence (i.e. a DJ-1 derived peptide).

The term "peptide" as used herein refers to a polymer of natural or synthetic amino acids, encompassing native peptides (either degradation products, synthetically synthesized peptides or recombinant peptides) and peptidomimetics (typically, synthetically synthesized peptides), as well as peptoids and semipeptoids which are peptide analogs, which may have, for example, modifications rendering the peptides even more stable while in a body or more capable of penetrating into cells.

Such modifications include, but are not limited to N terminus modification, C terminus modification, peptide bond modification, including, but not limited to, CH2-NH, CH2-S, CH2-S=O, O=C—NH, CH2-O, CH2-CH2, S=C—NH, CH=CH or CF=CH, backbone modifications, and residue modification. Methods for preparing peptidomimetic compounds are well known in the art and are specified, for example, in Quantitative Drug Design, C. A. Ramsden Gd., Chapter 17.2, F. Choplin Pergamon Press (1992), which is incorporated by reference as if fully set forth herein. Further details in this respect are provided hereinunder.

Peptide bonds (—CO—NH—) within the peptide may be substituted, for example, by N-methylated bonds (—N(CH3)—CO—), ester bonds (—C(R)H—C—O—O—C(R)—N—), ketomethylen bonds (—CO—CH2—), α-aza bonds (—NH—N(R)—CO—), wherein R is any alkyl, e.g., methyl, carba bonds (—CH2—NH—), hydroxyethylene bonds (—CH(OH)—CH2—), thioamide bonds (—CS—NH—), olefinic double bonds (—CH=CH—), retro amide bonds (—NH—CO—), peptide derivatives (—N(R)—CH2-CO—), wherein R is the "normal" side chain, naturally presented on the carbon atom.

These modifications can occur at any of the bonds along the peptide chain and even at several (2-3) at the same time.

Natural aromatic amino acids, Trp, Tyr and Phe, may be substituted for synthetic non-natural acid such as Phenylglycine, TIC, naphthylelanine (Nol), ring-methylated derivatives of Phe, halogenated derivatives of Phe or o-methyl-Tyr.

In addition to the above, the peptides of the present invention may also include one or more modified amino acids or one or more non-amino acid monomers (e.g. fatty acids, complex carbohydrates etc).

As used herein in the specification and in the claims section below the term "amino acid" or "amino acids" is understood to include the 20 naturally occurring amino acids; those amino acids often modified post-translationally in vivo, including, for example, hydroxyproline, phosphoserine and phosphothreonine; and other unusual amino acids including, but not limited to, 2-aminoadipic acid, hydroxylysine, isodesmosine, nor-valine, nor-leucine and ornithine. Furthermore, the term "amino acid" includes both D- and L-amino acids (stereoisomers).

Tables 1 and 2 below list naturally occurring amino acids (Table 1) and non-conventional or modified amino acids (Table 2) which can be used with the present invention.

TABLE 1

| Amino Acid | Three-Letter Abbreviation | One-letter Symbol |
| --- | --- | --- |
| alanine | Ala | A |
| Arginine | Arg | R |
| Asparagine | Asn | N |
| Aspartic acid | Asp | D |
| Cysteine | Cys | C |
| Glutamine | Gln | Q |
| Glutamic Acid | Glu | E |
| glycine | Gly | G |
| Histidine | His | H |
| isoleucine | Iie | I |
| leucine | Leu | L |

TABLE 1-continued

| Amino Acid | Three-Letter Abbreviation | One-letter Symbol |
|---|---|---|
| Lysine | Lys | K |
| Methionine | Met | M |
| phenylalanine | Phe | F |
| Proline | Pro | P |
| Serine | Ser | S |
| Threonine | Thr | T |
| tryptophan | Trp | W |
| tyrosine | Tyr | Y |
| Valine | Val | V |
| Any amino acid as above | Xaa | X |

TABLE 2

| Non-conventional amino acid | Code | Non-conventional amino acid | Code |
|---|---|---|---|
| α-aminobutyric acid | Abu | L-N-methylalanine | Nmala |
| α-amino-α-methylbutyrate | Mgabu | L-N-methylarginine | Nmarg |
| aminocyclopropane-carboxylate | Cpro | L-N-methylasparagine | Nmasn |
|  |  | L-N-methylaspartic acid | Nmasp |
| aminoisobutyric acid | Aib | L-N-methylcysteine | Nmcys |
| aminonorbornyl-carboxylate | Norb | L-N-methylglutamine | Nmgln |
|  |  | L-N-methylglutamic acid | Nmglu |
| cyclohexylalanine | Chexa | L-N-methylhistidine | Nmhis |
| cyclopentylalanine | Cpen | L-N-methylisoleucine | Nmile |
| D-alanine | Dal | L-N-methylleucine | Nmleu |
| D-arginine | Darg | L-N-methyllysine | Nmlys |
| D-aspartic acid | Dasp | L-N-methylmethionine | Nmmet |
| D-cysteine | Dcys | L-N-methylnorleucine | Nmnle |
| D-glutamine | Dgln | L-N-methylnorvaline | Nmnva |
| D-glutamic acid | Dglu | L-N-methylornithine | Nmorn |
| D-histidine | Dhis | L-N-methylphenylalanine | Nmphe |
| D-isoleucine | Dile | L-N-methylproline | Nmpro |
| D-leucine | Dleu | L-N-methylserine | Nmser |
| D-lysine | Dlys | L-N-methylthreonine | Nmthr |
| D-methionine | Dmet | L-N-methyltryptophan | Nmtrp |
| D-ornithine | Dorn | L-N-methyltyrosine | Nmtyr |
| D-phenylalanine | Dphe | L-N-methylvaline | Nmval |
| D-proline | Dpro | L-N-methylethylglycine | Nmetg |
| D-serine | Dser | L-N-methyl-t-butylglycine | Nmtbug |
| D-threonine | Dthr | L-norleucine | Nle |
| D-tryptophan | Dtrp | L-norvaline | Nva |
| D-tyrosine | Dtyr | α-methyl-aminoisobutyrate | Maib |
| D-valine | Dval | α-methyl-γ-aminobutyrate | Mgabu |
| D-α-methylalanine | Dmala | α ethylcyclohexylalanine | Mchexa |
| D-α-methylarginine | Dmarg | α-methylcyclopentylalanine | Mcpen |
| D-α-methylasparagine | Dmasn | α-methyl-α-napthylalanine | Manap |
| D-α-methylaspartate | Dmasp | α-methylpenicillamine | Mpen |
| D-α-methylcysteine | Dmcys | N-(4-aminobutyl)glycine | Nglu |
| D-α-methylglutamine | Dmgln | N-(2-aminoethyl)glycine | Naeg |
| D-α-methylhistidine | Dmhis | N-(3-aminopropyl)glycine | Norn |
| D-α-methylisoleucine | Dmile | N-amino-α-methylbutyrate | Nmaabu |
| D-α-methylleucine | Dmleu | α-napthylalanine | Anap |
| D-α-methyllysine | Dmlys | N-benzylglycine | Nphe |
| D-α-methylmethionine | Dmmet | N-(2-carbamylethyl)glycine | Ngln |
| D-α-methylornithine | Dmorn | N-(carbamylmethyl)glycine | Nasn |
| D-α-methylphenylalanine | Dmphe | N-(2-carboxyethyl)glycine | Nglu |
| D-α-methylproline | Dmpro | N-(carboxymethyl)glycine | Nasp |
| D-α-methylserine | Dmser | N-cyclobutylglycine | Ncbut |
| D-α-methylthreonine | Dmthr | N-cycloheptylglycine | Nchep |
| D-α-methyltryptophan | Dmtrp | N-cyclohexylglycine | Nchex |
| D-α-methyltyrosine | Dmty | N-cyclodecylglycine | Ncdec |
| D-α-methylvaline | Dmval | N-cyclododeclglycine | Ncdod |
| D-α-methylalnine | Dnmala | N-cyclooctylglycine | Ncoct |
| D-α-methylarginine | Dnmarg | N-cyclopropylglycine | Ncpro |
| D-α-methylasparagine | Dnmasn | N-cycloundecylglycine | Ncund |
| D-α-methylasparatate | Dnmasp | N-(2,2-diphenylethyl)glycine | Nbhm |
| D-α-methylcysteine | Dnmcys | N-(3,3-diphenylpropyl)glycine | Nbhe |
| D-N-methylleucine | Dnmleu | N-(3-indolylyethyl) glycine | Nhtrp |
| D-N-methyllysine | Dnmlys | N-methyl-γ-aminobutyrate | Nmgabu |
| N-methylcyclohexylalanine | Nmchexa | D-N-methylmethionine | Dnmmet |
| D-N-methylornithine | Dnmorn | N-methylcyclopentylalanine | Nmcpen |
| N-methylglycine | Nala | D-N-methylphenylalanine | Dnmphe |
| N-methylaminoisobutyrate | Nmaib | D-N-methylproline | Dnmpro |
| N-(1-methylpropyl)glycine | Nile | D-N-methylserine | Dnmser |
| N-(2-methylpropyl)glycine | Nile | D-N-methylserine | Dnmser |
| N-(2-methylpropyl)glycine | Nleu | D-N-methylthreonine | Dnmthr |
| D-N-methyltryptophan | Dnmtrp | N-(1-methylethyl)glycine | Nva |
| D-N-methyltyrosine | Dnmtyr | N-methyla-napthylalanine | Nmanap |
| D-N-methylvaline | Dnmval | N-methylpenicillamine | Nmpen |

TABLE 2-continued

| Non-conventional amino acid | Code | Non-conventional amino acid | Code |
|---|---|---|---|
| γ-aminobutyric acid | Gabu | N-(p-hydroxyphenyl)glycine | Nhtyr |
| L-t-butylglycine | Tbug | N-(thiomethyl)glycine | Ncys |
| L-ethylglycine | Etg | penicillamine | Pen |
| L-homophenylalanine | Hphe | L-α-methylalanine | Mala |
| L-α-methylarginine | Marg | L-α-methylasparagine | Masn |
| L-α-methylaspartate | Masp | L-α-methyl-t-butylglycine | Mtbug |
| L-α-methylcysteine | Mcys | L-methylethylglycine | Metg |
| L-α thylglutamine | Mgln | L-α-methylglutamate | Mglu |
| L-α-methylhistidine | Mhis | L-α-methylhomo phenylalanine | Mhphe |
| L-α-methylisoleucine | Mile | N-(2-methylthioethyl)glycine | Nmet |
| D-N-methylglutamine | Dnmgln | N-(3-guanidinopropyl)glycine | Narg |
| D-N-methylglutamate | Dnmglu | N-(1-hydroxyethyl)glycine | Nthr |
| D-N-methylhistidine | Dnmhis | N-(hydroxyethyl)glycine | Nser |
| D-N-methylisoleucine | Dnmile | N-(imidazolylethyl)glycine | Nhis |
| D-N-methylleucine | Dnmleu | N-(3-indolylyethyl)glycine | Nhtrp |
| D-N-methyllysine | Dnmlys | N-methyl-γ-aminobutyrate | Nmgabu |
| N-methylcyclohexylalanine | Nmchexa | D-N-methylmethionine | Dnmmet |
| D-N-methylornithine | Dnmorn | N-methylcyclopentylalanine | Nmcpen |
| N-methylglycine | Nala | D-N-methylphenylalanine | Dnmphe |
| N-methylaminoisobutyrate | Nmaib | D-N-methylproline | Dnmpro |
| N-(1-methylpropyl)glycine | Nile | D-N-methylserine | Dnmser |
| N-(2-methylpropyl)glycine | Nleu | D-N-methylthreonine | Dnmthr |
| D-N-methyltryptophan | Dnmtrp | N-(1-methylethyl)glycine | Nval |
| D-N-methyltyrosine | Dnmtyr | N-methyla-napthylalanine | Nmanap |
| D-N-methylvaline | Dnmval | N-methylpenicillamine | Nmpen |
| γ-aminobutyric acid | Gabu | N-(p-hydroxyphenyl)glycine | Nhtyr |
| L-t-butylglycine | Tbug | N-(thiomethyl)glycine | Ncys |
| L-ethylglycine | Etg | penicillamine | Pen |
| L-homophenylalanine | Hphe | L-α-methylalanine | Mala |
| L-α-methylarginine | Marg | L-α-methylasparagine | Masn |
| L-α-methylaspartate | Masp | L-α-methyl-t-butylglycine | Mtbug |
| L-α-methylcysteine | Mcys | L-methylethylglycine | Metg |
| L-α-methylglutamine | Mgln | L-α-methylglutamate | Mglu |
| L-α ethylhistidine | Mhis | L-α-methylhomophenylalanine | Mhphe |
| L-α thylisoleucine | Mile | N-(2-methylthioethyl)glycine | Nmet |
| L-α-methylleucine | Mleu | L-α-methyllysine | Mlys |
| L-α-methylmethionine | Mmet | L-α-methylnorleucine | Mnle |
| L-α-methylnorvaline | Mnva | L-α-methylornithine | Morn |
| L-α-methylphenylalanine | Mphe | L-α-methylproline | Mpro |
| L-α-methylserine | mser | L-α-methylthreonine | Mthr |
| L-α ethylvaline | Mtrp | L-α-methyltyrosine | Mtyr |
| L-α-methylleucine | Mval nbhm | L-N-methylhomophenylalanine | Nmhphe |
| N-(N-(2,2-diphenylethyl) carbamylmethyl-glycine | Nnbhm | N-(N-(3,3-diphenylpropyl) carbamylmethyl(1)glycine | Nnbhe |
| 1-carboxy-1-(2,2-diphenyl hylamino)cyclopropane | Nmbc | | |

According to one embodiment, the DJ-1 derived peptide comprises at least a 5% sequence homology to DJ-1. Preferably, the 5% homology covers at least part of the sequence of the DJ-1 peptide that is capable of enhancing VMAT2 transcription. According to one embodiment, the peptide is 5 amino acids long. According to another embodiment, the peptide is 6 amino acids long. According to another embodiment, the peptide is 7 amino acids long. According to another embodiment, the peptide is 8 amino acids long. According to another embodiment, the peptide is 9 amino acids long. According to another embodiment, the peptide is 10 amino acids long. According to another embodiment, the peptide is 11 amino acids long. According to another embodiment, the peptide is 12 amino acids long. According to another embodiment, the peptide is 13 amino acids long. According to another embodiment, the peptide is 14 amino acids long. According to another embodiment, the peptide is 15 amino acids long. According to another embodiment, the peptide is 16 amino acids long. According to another embodiment, the peptide is 17 amino acids long. According to another embodiment, the peptide is 18 amino acids long. According to another embodiment, the peptide is 19 amino acids long. According to another embodiment, the peptide is 20 amino acids long. According to another embodiment, the peptide is 25 amino acids long. According to another embodiment, the peptide is no more than about 30 amino acids long. According to another embodiment, the peptide is no more than about 40 amino acids long. According to another embodiment, the peptide is no more than about 50 amino acids long. According to another embodiment, the peptide is no more than about 60 amino acids long.

According to one embodiment the DJ-1 derived peptides comprise amino acid sequences whose deletions and point mutations were shown to be associated with Parkinson's—see e.g. Bonifati, V., et al. Science 299, 256-259 (2003); Abou-Sleiman, P. M., et al., Ann. Neurol. 54, 283-286 (2003); Hedrich, K., et al. Neurology 62, 389-394 (2004).

According to another embodiment the DJ-1 derived peptides comprise amino acid sequences which were shown using bioinformatics anlaysis (e.g. ConSeg™ analysis) to be important for structure and/or functionality (e.g. capable of up-regulating transcription of VMAT2). As illustrated in FIG. 5, 17 amino acids were shown to be important for functionality and 13 amino acids were shown to be important for structure.

Thus, according to another embodiment of this aspect of the present invention, the DJ-1 derived peptides comprise at least one of the following amino acid sequences: amino acids 13-33 of DJ-1—SEQ ID NO: 1; amino acids 44-55 of DJ-1—SEQ ID NO: 2; amino acids 69-79 of DJ-1—SEQ ID NO: 3; amino acids 103-112 of DJ-1—SEQ ID NO: 4; amino acids 124-130 of DJ-1—SEQ ID NO: 5; and amino acids 146-174 of DJ-1—SEQ ID NO: 6.

Other exemplary contemplated peptides listed in Table 3, herein below are those that comprise at least part of the amino acid sequence of SEQ ID NOs: 1-6.

TABLE 3

| seq id no: | derived from DJ-1 peptide no: | Sequence | Peptide Length |
|---|---|---|---|
| 17 | 1 | GAEE | 4 |
| 18 | 1 | AEEM | 4 |
| 19 | 1 | EEME | 4 |
| 20 | 1 | EMET | 4 |
| 21 | 1 | METV | 4 |
| 22 | 1 | ETVI | 4 |
| 23 | 1 | TVIP | 4 |
| 24 | 1 | VIPV | 4 |
| 25 | 1 | IPVD | 4 |
| 26 | 1 | PVDV | 4 |
| 27 | 1 | VDVM | 4 |
| 28 | 1 | DVMR | 4 |
| 29 | 1 | VMRR | 4 |
| 30 | 1 | MRRA | 4 |
| 31 | 1 | RRAG | 4 |
| 32 | 1 | RAGI | 4 |
| 33 | 1 | AGIK | 4 |
| 34 | 1 | GIKV | 4 |
| 35 | 1 | GAEEM | 5 |
| 36 | 1 | AEEME | 5 |
| 37 | 1 | EEMET | 5 |
| 38 | 1 | EMETV | 5 |
| 39 | 1 | METVI | 5 |
| 40 | 1 | ETVIP | 5 |
| 41 | 1 | TVIPV | 5 |
| 42 | 1 | VIPVD | 5 |
| 43 | 1 | IPVDV | 5 |
| 44 | 1 | PVDVM | 5 |
| 45 | 1 | VDVMR | 5 |
| 46 | 1 | DVMRR | 5 |
| 47 | 1 | VMRRA | 5 |
| 48 | 1 | MRRAG | 5 |

TABLE 3-continued

| seq id no: | derived from DJ-1 peptide no: | Sequence | Peptide Length |
|---|---|---|---|
| 49 | 1 | RRAGI | 5 |
| 50 | 1 | RAGIK | 5 |
| 51 | 1 | AGIKV | 5 |
| 52 | 1 | GAEEME | 6 |
| 53 | 1 | AEEMET | 6 |
| 54 | 1 | EEMETV | 6 |
| 55 | 1 | EMETVI | 6 |
| 56 | 1 | METVIP | 6 |
| 57 | 1 | ETVIPV | 6 |
| 58 | 1 | TVIPVD | 6 |
| 59 | 1 | VIPVDV | 6 |
| 60 | 1 | IPVDVM | 6 |
| 61 | 1 | PVDVMR | 6 |
| 62 | 1 | VDVMRR | 6 |
| 63 | 1 | DVMRRA | 6 |
| 64 | 1 | VMRRAG | 6 |
| 65 | 1 | MRRAGI | 6 |
| 66 | 1 | RRAGIK | 6 |
| 67 | 1 | RAGIKV | 6 |
| 68 | 1 | GAEEMET | 7 |
| 69 | 1 | AEEMETV | 7 |
| 70 | 1 | EEMETVI | 7 |
| 71 | 1 | EMETVIP | 7 |
| 72 | 1 | METVIPV | 7 |
| 73 | 1 | ETVIPVD | 7 |
| 74 | 1 | TVIPVDV | 7 |
| 75 | 1 | VIPVDVM | 7 |
| 76 | 1 | IPVDVMR | 7 |
| 77 | 1 | PVDVMRR | 7 |
| 78 | 1 | VDVMRRA | 7 |
| 79 | 1 | DVMRRAG | 7 |
| 80 | 1 | VMRRAGI | 7 |
| 81 | 1 | MRRAGIK | 7 |
| 82 | 1 | RRAGIKV | 7 |
| 83 | 1 | GAEEMETV | 8 |
| 84 | 1 | AEEMETVI | 8 |
| 85 | 1 | EEMETVIP | 8 |
| 86 | 1 | EMETVIPV | 8 |

TABLE 3-continued

| seq id no: | derived from DJ-1 peptide no: | Sequence | Peptide Length |
|---|---|---|---|
| 87 | 1 | METVIPVD | 8 |
| 88 | 1 | ETVIPVDV | 8 |
| 89 | 1 | TVIPVDVM | 8 |
| 90 | 1 | VIPVDVMR | 8 |
| 91 | 1 | IPVDVMRR | 8 |
| 92 | 1 | PVDVMRRA | 8 |
| 93 | 1 | VDVMRRAG | 8 |
| 94 | 1 | DVMRRAGI | 8 |
| 95 | 1 | VMRRAGIK | 8 |
| 96 | 1 | MRRAGIKV | 8 |
| 97 | 1 | GAEEMETVI | 9 |
| 98 | 1 | AEEMETVIP | 9 |
| 99 | 1 | EEMETVIPV | 9 |
| 100 | 1 | EMETVIPVD | 9 |
| 101 | 1 | METVIPVDV | 9 |
| 102 | 1 | ETVIPVDVM | 9 |
| 103 | 1 | TVIPVDVMR | 9 |
| 104 | 1 | VIPVDVMRR | 9 |
| 105 | 1 | IPVDVMRRA | 9 |
| 106 | 1 | PVDVMRRAG | 9 |
| 107 | 1 | VDVMRRAGI | 9 |
| 108 | 1 | DVMRRAGIK | 9 |
| 109 | 1 | VMRRAGIKV | 9 |
| 110 | 1 | GAEEMETVIP | 10 |
| 111 | 1 | AEEMETVIPV | 10 |
| 112 | 1 | EEMETVIPVD | 10 |
| 113 | 1 | EMETVIPVDV | 10 |
| 114 | 1 | METVIPVDVM | 10 |
| 115 | 1 | ETVIPVDVMR | 10 |
| 116 | 1 | TVIPVDVMRR | 10 |
| 117 | 1 | VIPVDVMRRA | 10 |
| 118 | 1 | IPVDVMRRAG | 10 |
| 119 | 1 | PVDVMRRAGI | 10 |
| 120 | 1 | VDVMRRAGIK | 10 |
| 121 | 1 | DVMRRAGIKV | 10 |
| 122 | 1 | GAEEMETVIPV | 11 |
| 123 | 1 | AEEMETVIPVD | 11 |
| 124 | 1 | EEMETVIPVDV | 11 |
| 125 | 1 | EMETVIPVDVM | 11 |
| 126 | 1 | METVIPVDVMR | 11 |
| 127 | 1 | ETVIPVDVMRR | 11 |
| 128 | 1 | TVIPVDVMRRA | 11 |
| 129 | 1 | VIPVDVMRRAG | 11 |
| 130 | 1 | IPVDVMRRAGI | 11 |
| 131 | 1 | PVDVMRRAGIK | 11 |
| 132 | 1 | VDVMRRAGIKV | 11 |
| 133 | 1 | GAEEMETVIPVD | 12 |
| 134 | 1 | AEEMETVIPVDV | 12 |
| 135 | 1 | EEMETVIPVDVM | 12 |
| 136 | 1 | EMETVIPVDVMR | 12 |
| 137 | 1 | METVIPVDVMRR | 12 |
| 138 | 1 | ETVIPVDVMRRA | 12 |
| 139 | 1 | TVIPVDVMRRAG | 12 |
| 140 | 1 | VIPVDVMRRAGI | 12 |
| 141 | 1 | IPVDVMRRAGIK | 12 |
| 142 | 1 | PVDVMRRAGIKV | 12 |
| 143 | 1 | GAEEMETVIPVDV | 13 |
| 144 | 1 | AEEMETVIPVDVM | 13 |
| 145 | 1 | EEMETVIPVDVMR | 13 |
| 146 | 1 | EMETVIPVDVMRR | 13 |
| 147 | 1 | METVIPVDVMRRA | 13 |
| 148 | 1 | ETVIPVDVMRRAG | 13 |
| 149 | 1 | TVIPVDVMRRAGI | 13 |
| 150 | 1 | VIPVDVMRRAGIK | 13 |
| 151 | 1 | IPVDVMRRAGIKV | 13 |
| 152 | 1 | GAEEMETVIPVDVM | 14 |
| 153 | 1 | AEEMETVIPVDVMR | 14 |
| 154 | 1 | EEMETVIPVDVMRR | 14 |
| 155 | 1 | EMETVIPVDVMRRA | 14 |
| 156 | 1 | METVIPVDVMRRAG | 14 |
| 157 | 1 | ETVIPVDVMRRAGI | 14 |
| 158 | 1 | TVIPVDVMRRAGIK | 14 |
| 159 | 1 | VIPVDVMRRAGIKV | 14 |
| 160 | 1 | GAEEMETVIPVDVMR | 15 |
| 161 | 1 | AEEMETVIPVDVMRR | 15 |
| 162 | 1 | EEMETVIPVDVMRRA | 15 |

TABLE 3-continued

| seq id no: | derived from DJ-1 peptide no: | Sequence | Peptide Length |
|---|---|---|---|
| 163 | 1 | EMETVIPVDVMRRAG | 15 |
| 164 | 1 | METVIPVDVMRRAGI | 15 |
| 165 | 1 | ETVIPVDVMRRAGIK | 15 |
| 166 | 1 | TVIPVDVMRRAGIKV | 15 |
| 167 | 2 | VQCS | 4 |
| 168 | 2 | QCSR | 4 |
| 169 | 2 | CSRD | 4 |
| 170 | 2 | SRDV | 4 |
| 171 | 2 | RDVV | 4 |
| 172 | 2 | DVVI | 4 |
| 173 | 2 | VVIC | 4 |
| 174 | 2 | VICP | 4 |
| 175 | 2 | ICPD | 4 |
| 176 | 2 | VQCSR | 5 |
| 177 | 2 | QCSRD | 5 |
| 178 | 2 | CSRDV | 5 |
| 179 | 2 | SRDVV | 5 |
| 180 | 2 | RDVVI | 5 |
| 181 | 2 | DVVIC | 5 |
| 182 | 2 | VVICP | 5 |
| 183 | 2 | VICPD | 5 |
| 184 | 2 | VQCSRD | 6 |
| 185 | 2 | QCSRDV | 6 |
| 186 | 2 | CSRDVV | 6 |
| 187 | 2 | SRDVVI | 6 |
| 188 | 2 | RDVVIC | 6 |
| 189 | 2 | DVVICP | 6 |
| 190 | 2 | VVICPD | 6 |
| 191 | 2 | VQCSRDV | 7 |
| 192 | 2 | QCSRDVV | 7 |
| 193 | 2 | CSRDVVI | 7 |
| 194 | 2 | SRDVVIC | 7 |
| 195 | 2 | RDVVICP | 7 |
| 196 | 2 | DVVICPD | 7 |
| 197 | 2 | VQCSRDVV | 8 |
| 198 | 2 | QCSRDVVI | 8 |
| 199 | 2 | CSRDVVIC | 8 |
| 200 | 2 | SRDVVICP | 8 |
| 201 | 2 | RDVVICPD | 8 |
| 202 | 2 | VQCSRDVVI | 9 |
| 203 | 2 | QCSRDVVIC | 9 |
| 204 | 2 | CSRDVVICP | 9 |
| 205 | 2 | SRDVVICPD | 9 |
| 206 | 2 | VQCSRDVVIC | 10 |
| 207 | 2 | QCSRDVVICP | 10 |
| 208 | 2 | CSRDVVICPD | 10 |
| 209 | 2 | VQCSRDVVICP | 11 |
| 210 | 2 | QCSRDVVICPD | 11 |
| 211 | 3 | VVVL | 4 |
| 212 | 3 | VVLP | 4 |
| 213 | 3 | VLPG | 4 |
| 214 | 3 | LPGG | 4 |
| 215 | 3 | PGGN | 4 |
| 216 | 3 | GGNL | 4 |
| 217 | 3 | GNLG | 4 |
| 218 | 3 | NLGA | 4 |
| 219 | 3 | VVVLP | 5 |
| 220 | 3 | VVLPG | 5 |
| 221 | 3 | VLPGG | 5 |
| 222 | 3 | LPGGN | 5 |
| 223 | 3 | PGGNL | 5 |
| 224 | 3 | GGNLG | 5 |
| 225 | 3 | GNLGA | 5 |
| 226 | 3 | VVVLPG | 6 |
| 227 | 3 | VVLPGG | 6 |
| 228 | 3 | VLPGGN | 6 |
| 229 | 3 | LPGGNL | 6 |
| 230 | 3 | PGGNLG | 6 |
| 231 | 3 | GGNLGA | 6 |
| 232 | 3 | VVVLPGG | 7 |
| 233 | 3 | VVLPGGN | 7 |
| 234 | 3 | VLPGGNL | 7 |
| 235 | 3 | LPGGNLG | 7 |
| 236 | 3 | PGGNLGA | 7 |
| 237 | 3 | VVVLPGGN | 8 |
| 238 | 3 | VVLPGGNL | 8 |

TABLE 3-continued

| seq id no: | derived from DJ-1 peptide no: | Sequence | Peptide Length |
|---|---|---|---|
| 239 | 3 | VLPGGNLG | 8 |
| 240 | 3 | LPGGNLGA | 8 |
| 241 | 3 | VVVLPGGNL | 9 |
| 242 | 3 | VVLPGGNLG | 9 |
| 243 | 3 | VLPGGNLGA | 9 |
| 244 | 3 | VVVLPGGNLG | 10 |
| 245 | 3 | VVLPGGNLGA | 10 |
| 246 | 4 | AAIC | 4 |
| 247 | 4 | AICA | 4 |
| 248 | 4 | ICAG | 4 |
| 249 | 4 | CAGP | 4 |
| 250 | 4 | AGPT | 4 |
| 251 | 4 | GPTA | 4 |
| 252 | 4 | PTAL | 4 |
| 253 | 4 | AAICA | 5 |
| 254 | 4 | AICAG | 5 |
| 255 | 4 | ICAGP | 5 |
| 256 | 4 | CAGPT | 5 |
| 257 | 4 | AGPTA | 5 |
| 258 | 4 | GPTAL | 5 |
| 259 | 4 | AAICAG | 6 |
| 260 | 4 | AICAGP | 6 |
| 261 | 4 | ICAGPT | 6 |
| 262 | 4 | CAGPTA | 6 |
| 263 | 4 | AGPTAL | 6 |
| 264 | 4 | AAICAGP | 7 |
| 265 | 4 | AICAGPT | 7 |
| 266 | 4 | ICAGPTA | 7 |
| 267 | 4 | CAGPTAL | 7 |
| 268 | 4 | AAICAGPT | 8 |
| 269 | 4 | AICAGPTA | 8 |
| 270 | 4 | ICAGPTAL | 8 |
| 271 | 4 | AAICAGPTA | 9 |
| 272 | 4 | AICAGPTAL | 9 |
| 273 | 5 | TTHP | 4 |
| 274 | 5 | THPL | 4 |
| 275 | 5 | HPLA | 4 |
| 276 | 5 | PLAK | 4 |
| 277 | 5 | TTHPL | 5 |
| 278 | 5 | THPLA | 5 |
| 279 | 5 | HPLAK | 5 |
| 280 | 5 | TTHPLA | 6 |
| 281 | 5 | THPLAK | 6 |
| 282 | 6 | VEKD | 4 |
| 283 | 6 | EKDG | 4 |
| 284 | 6 | KDGL | 4 |
| 285 | 6 | DGLI | 4 |
| 286 | 6 | GLIL | 4 |
| 287 | 6 | LILT | 4 |
| 288 | 6 | ILTS | 4 |
| 289 | 6 | LTSR | 4 |
| 290 | 6 | TSRG | 4 |
| 291 | 6 | SRGP | 4 |
| 292 | 6 | RGPG | 4 |
| 293 | 6 | GPGT | 4 |
| 294 | 6 | PGTS | 4 |
| 295 | 6 | GTSF | 4 |
| 296 | 6 | TSFE | 4 |
| 297 | 6 | SFEF | 4 |
| 298 | 6 | FEFA | 4 |
| 299 | 6 | EFAL | 4 |
| 300 | 6 | FALA | 4 |
| 301 | 6 | ALAI | 4 |
| 302 | 6 | LAIV | 4 |
| 303 | 6 | AIVE | 4 |
| 304 | 6 | IVEA | 4 |
| 305 | 6 | VEAL | 4 |
| 306 | 6 | EALN | 4 |
| 307 | 6 | ALNG | 4 |
| 308 | 6 | VEKDG | 5 |
| 309 | 6 | EKDGL | 5 |
| 310 | 6 | KDGLI | 5 |
| 311 | 6 | DGLIL | 5 |
| 312 | 6 | GLILT | 5 |
| 313 | 6 | LILTS | 5 |
| 314 | 6 | ILTSR | 5 |

TABLE 3-continued

| seq id no: | derived from DJ-1 peptide no: | Sequence | Peptide Length |
|---|---|---|---|
| 315 | 6 | LTSRG | 5 |
| 316 | 6 | TSRGP | 5 |
| 317 | 6 | SRGPG | 5 |
| 318 | 6 | RGPGT | 5 |
| 319 | 6 | GPGTS | 5 |
| 320 | 6 | PGTSF | 5 |
| 321 | 6 | GTSFE | 5 |
| 322 | 6 | TSFEF | 5 |
| 323 | 6 | SFEFA | 5 |
| 324 | 6 | FEFAL | 5 |
| 325 | 6 | EFALA | 5 |
| 326 | 6 | FALAT | 5 |
| 327 | 6 | ALAIV | 5 |
| 328 | 6 | LAIVE | 5 |
| 329 | 6 | AIVEA | 5 |
| 330 | 6 | IVEAL | 5 |
| 331 | 6 | VEALN | 5 |
| 332 | 6 | EALNG | 5 |
| 333 | 6 | VEKDGL | 6 |
| 334 | 6 | EKDGLI | 6 |
| 335 | 6 | KDGLIL | 6 |
| 336 | 6 | DGLILT | 6 |
| 337 | 6 | GLILTS | 6 |
| 338 | 6 | LILTSR | 6 |
| 339 | 6 | ILTSRG | 6 |
| 340 | 6 | LTSRGP | 6 |
| 341 | 6 | TSRGPG | 6 |
| 342 | 6 | SRGPGT | 6 |
| 343 | 6 | RGPGTS | 6 |
| 344 | 6 | GPGTSF | 6 |
| 345 | 6 | PGTSFE | 6 |
| 346 | 6 | GTSFEF | 6 |
| 347 | 6 | TSFEFA | 6 |
| 348 | 6 | SFEFAL | 6 |
| 349 | 6 | FEFALA | 6 |
| 350 | 6 | EFALAI | 6 |
| 351 | 6 | FALAIV | 6 |
| 352 | 6 | ALAIVE | 6 |
| 353 | 6 | LAIVEA | 6 |
| 354 | 6 | AIVEAL | 6 |
| 355 | 6 | IVEALN | 6 |
| 356 | 6 | VEALNG | 6 |
| 357 | 6 | VEKDGLI | 7 |
| 358 | 6 | EKDGLIL | 7 |
| 359 | 6 | KDGLILT | 7 |
| 360 | 6 | DGLILTS | 7 |
| 361 | 6 | GLILTSR | 7 |
| 362 | 6 | LILTSRG | 7 |
| 363 | 6 | ILTSRGP | 7 |
| 364 | 6 | LTSRGPG | 7 |
| 365 | 6 | TSRGPGT | 7 |
| 366 | 6 | SRGPGTS | 7 |
| 367 | 6 | RGPGTSF | 7 |
| 368 | 6 | GPGTSFE | 7 |
| 369 | 6 | PGTSFEF | 7 |
| 370 | 6 | GTSFEFA | 7 |
| 371 | 6 | TSFEFAL | 7 |
| 372 | 6 | SFEFALA | 7 |
| 373 | 6 | FEFALAI | 7 |
| 374 | 6 | EFALAIV | 7 |
| 375 | 6 | FALAIVE | 7 |
| 376 | 6 | ALAIVEA | 7 |
| 377 | 6 | LAIVEAL | 7 |
| 378 | 6 | AIVEALN | 7 |
| 379 | 6 | IVEALNG | 7 |
| 380 | 6 | VEKDGLIL | 8 |
| 381 | 6 | EKDGLILT | 8 |
| 382 | 6 | KDGLILTS | 8 |
| 383 | 6 | DGLILTSR | 8 |
| 384 | 6 | GLILTSRG | 8 |
| 385 | 6 | LILTSRGP | 8 |
| 386 | 6 | ILTSRGPG | 8 |
| 387 | 6 | LTSRGPGT | 8 |
| 388 | 6 | TSRGPGTS | 8 |
| 389 | 6 | SRGPGTSF | 8 |
| 390 | 6 | RGPGTSFE | 8 |

TABLE 3-continued

| seq id no: | derived from DJ-1 peptide no: | Sequence | Peptide Length |
|---|---|---|---|
| 391 | 6 | GPGTSFEF | 8 |
| 392 | 6 | PGTSFEFA | 8 |
| 393 | 6 | GTSFEFAL | 8 |
| 394 | 6 | TSFEFALA | 8 |
| 395 | 6 | SFEFALAI | 8 |
| 396 | 6 | FEFALAIV | 8 |
| 397 | 6 | EFALAIVE | 8 |
| 398 | 6 | FALAIVEA | 8 |
| 399 | 6 | ALAIVEAL | 8 |
| 400 | 6 | LAIVEALN | 8 |
| 401 | 6 | AIVEALNG | 8 |
| 402 | 6 | VEKDGLILT | 9 |
| 403 | 6 | EKDGLILTS | 9 |
| 404 | 6 | KDGLILTSR | 9 |
| 405 | 6 | DGLILTSRG | 9 |
| 406 | 6 | GLILTSRGP | 9 |
| 407 | 6 | LILTSRGPG | 9 |
| 408 | 6 | ILTSRGPGT | 9 |
| 409 | 6 | LTSRGPGTS | 9 |
| 410 | 6 | TSRGPGTSF | 9 |
| 411 | 6 | SRGPGTSFE | 9 |
| 412 | 6 | RGPGTSFEF | 9 |
| 413 | 6 | GPGTSFEFA | 9 |
| 414 | 6 | PGTSFEFAL | 9 |
| 415 | 6 | GTSFEFALA | 9 |
| 416 | 6 | TSFEFALAI | 9 |
| 417 | 6 | SFEFALAIV | 9 |
| 418 | 6 | FEFALAIVE | 9 |
| 419 | 6 | EFALAIVEA | 9 |
| 420 | 6 | FALAIVEAL | 9 |
| 421 | 6 | ALAIVEALN | 9 |
| 422 | 6 | LAIVEALNG | 9 |
| 423 | 6 | VEKDGLILTS | 10 |
| 424 | 6 | EKDGLILTSR | 10 |
| 425 | 6 | KDGLILTSRG | 10 |
| 426 | 6 | DGLILTSRGP | 10 |
| 427 | 6 | GLILTSRGPG | 10 |
| 428 | 6 | LILTSRGPGT | 10 |
| 429 | 6 | ILTSRGPGTS | 10 |
| 430 | 6 | LTSRGPGTSF | 10 |
| 431 | 6 | TSRGPGTSFE | 10 |
| 432 | 6 | SRGPGTSFEF | 10 |
| 433 | 6 | RGPGTSFEFA | 10 |
| 434 | 6 | GPGTSFEFAL | 10 |
| 435 | 6 | PGTSFEFALA | 10 |
| 436 | 6 | GTSFEFALAI | 10 |
| 437 | 6 | TSFEFALAIV | 10 |
| 438 | 6 | SFEFALAIVE | 10 |
| 439 | 6 | FEFALAIVEA | 10 |
| 440 | 6 | EFALAIVEAL | 10 |
| 441 | 6 | FALAIVEALN | 10 |
| 442 | 6 | ALAIVEALNG | 10 |
| 443 | 6 | VEKDGLILTSR | 11 |
| 444 | 6 | EKDGLILTSRG | 11 |
| 445 | 6 | KDGLILTSRGP | 11 |
| 446 | 6 | DGLILTSRGPG | 11 |
| 447 | 6 | GLILTSRGPGT | 11 |
| 448 | 6 | LILTSRGPGTS | 11 |
| 449 | 6 | ILTSRGPGTSF | 11 |
| 450 | 6 | LTSRGPGTSFE | 11 |
| 451 | 6 | TSRGPGTSFEF | 11 |
| 452 | 6 | SRGPGTSFEFA | 11 |
| 453 | 6 | RGPGTSFEFAL | 11 |
| 454 | 6 | GPGTSFEFALA | 11 |
| 455 | 6 | PGTSFEFALAI | 11 |
| 456 | 6 | GTSFEFALAIV | 11 |
| 457 | 6 | TSFEFALAIVE | 11 |
| 458 | 6 | SFEFALAIVEA | 11 |
| 459 | 6 | FEFALAIVEAL | 11 |
| 460 | 6 | EFALAIVEALN | 11 |
| 461 | 6 | FALAIVEALNG | 11 |
| 462 | 6 | VEKDGLILTSRG | 12 |
| 463 | 6 | EKDGLILTSRGP | 12 |
| 464 | 6 | KDGLILTSRGPG | 12 |
| 465 | 6 | DGLILTSRGPGT | 12 |
| 466 | 6 | GLILTSRGPGTS | 12 |

TABLE 3-continued

| seq id no: | derived from DJ-1 peptide no: | Sequence | Peptide Length |
|---|---|---|---|
| 467 | 6 | LILTSRGPGTSF | 12 |
| 468 | 6 | ILTSRGPGTSFE | 12 |
| 469 | 6 | LTSRGPGTSFEF | 12 |
| 470 | 6 | TSRGPGTSFEFA | 12 |
| 471 | 6 | SRGPGTSFEFAL | 12 |
| 472 | 6 | RGPGTSFEFALA | 12 |
| 473 | 6 | GPGTSFEFALAI | 12 |
| 474 | 6 | PGTSFEFALAIV | 12 |
| 475 | 6 | GTSFEFALAIVE | 12 |
| 476 | 6 | TSFEFALAIVEA | 12 |
| 477 | 6 | SFEFALAIVEAL | 12 |
| 478 | 6 | FEFALAIVEALN | 12 |
| 479 | 6 | EFALAIVEALNG | 12 |
| 480 | 6 | VEKDGLILTSRGP | 13 |
| 481 | 6 | EKDGLILTSRGPG | 13 |
| 482 | 6 | KDGLILTSRGPGT | 13 |
| 483 | 6 | DGLILTSRGPGTS | 13 |
| 484 | 6 | GLILTSRGPGTSF | 13 |
| 485 | 6 | LILTSRGPGTSFE | 13 |
| 486 | 6 | ILTSRGPGTSFEF | 13 |
| 487 | 6 | LTSRGPGTSFEFA | 13 |
| 488 | 6 | TSRGPGTSFEFAL | 13 |
| 489 | 6 | SRGPGTSFEFALA | 13 |
| 490 | 6 | RGPGTSFEFALAI | 13 |
| 491 | 6 | GPGTSFEFALAIV | 13 |
| 492 | 6 | PGTSFEFALAIVE | 13 |
| 493 | 6 | GTSFEFALAIVEA | 13 |
| 494 | 6 | TSFEFALAIVEAL | 13 |
| 495 | 6 | SFEFALAIVEALN | 13 |
| 496 | 6 | FEFALAIVEALNG | 13 |
| 497 | 6 | VEKDGLILTSRGPG | 14 |
| 498 | 6 | EKDGLILTSRGPGT | 14 |
| 499 | 6 | KDGLILTSRGPGTS | 14 |
| 500 | 6 | DGLILTSRGPGTSF | 14 |
| 501 | 6 | GLILTSRGPGTSFE | 14 |
| 502 | 6 | LILTSRGPGTSFEF | 14 |
| 503 | 6 | ILTSRGPGTSFEFA | 14 |
| 504 | 6 | LTSRGPGTSFEFAL | 14 |
| 505 | 6 | TSRGPGTSFEFALA | 14 |
| 506 | 6 | SRGPGTSFEFALAI | 14 |
| 507 | 6 | RGPGTSFEFALAIV | 14 |
| 508 | 6 | GPGTSFEFALAIVE | 14 |
| 509 | 6 | PGTSFEFALAIVEA | 14 |
| 510 | 6 | GTSFEFALAIVEAL | 14 |
| 511 | 6 | TSFEFALAIVEALN | 14 |
| 512 | 6 | SFEFALAIVEALNG | 14 |
| 513 | 6 | VEKDGLILTSRGPGT | 15 |
| 514 | 6 | EKDGLILTSRGPGTS | 15 |
| 515 | 6 | KDGLILTSRGPGTSF | 15 |
| 516 | 6 | DGLILTSRGPGTSFE | 15 |
| 517 | 6 | GLILTSRGPGTSFEF | 15 |
| 518 | 6 | LILTSRGPGTSFEFA | 15 |
| 519 | 6 | ILTSRGPGTSFEFAL | 15 |
| 520 | 6 | LTSRGPGTSFEFALA | 15 |
| 521 | 6 | TSRGPGTSFEFALAI | 15 |
| 522 | 6 | SRGPGTSFEFALAIV | 15 |
| 523 | 6 | RGPGTSFEFALAIVE | 15 |
| 524 | 6 | GPGTSFEFALAIVEA | 15 |
| 525 | 6 | PGTSFEFALAIVEAL | 15 |
| 526 | 6 | GTSFEFALAIVEALN | 15 |
| 527 | 6 | TSFEFALAIVEALNG | 15 |

Candidate peptide sequences may be screened by determining if there is an interaction between them and the VMAT2 promoter. Exemplary methods for such screening include EMSA (electromobility shift assay) and chromatin precipitation. Such methods are known to one skilled in the art.

Alternatively or additionally, the candidate peptides may be screened for regulatory activity of VMAT2 transcription. An exemplary method for analyzing such regulatory activity comprises transfecting a polynucleotide encoding the promoter region of VMAT2 (i.e. an exogenous VMAT2 promoter) linked to a detectable protein (i.e. reporter protein) into a cell—i.e. a reporter based assay. The method further comprises introducing the candidate peptide agents into the cell (e.g. by transfection of an expression vector encoding the agent) and detecting the detectable protein whereby the amount of the detectable protein reflects the transcriptional activity of the promoter. It will be appreciated that the polynucleotide sequence of any protein that may be readily detected may be transcriptionally linked to the VMAT2 promoter. Thus for example, the protein may be a phosphorescent protein such as luciferase, a fluorescent protein such as green fluorescent protein, a chemiluminescent protein or may be a non-directly detectable protein for which an antibody is available for detection thereof. Cells for analyzing transcriptional activity are further described hereinbelow.

It will be appreciated that transcriptional activity of endogenous VMAT2 may also be analyzed with VMAT2 being detected using a detectable agent such as an antibody.

Once the minimal amino acid sequence of DJ-1 is identified that is capable of transcriptionally activating VMAT2, other peptides may be synthesized (comprising conservative or non-conservative substitutions) in order to "tweak the system" and generate DJ-1-derived peptides with improved characteristics i.e. comprising an enhanced transcriptional activity.

The term "conservative substitution" as used herein, refers to the replacement of an amino acid present in the native sequence in the peptide with a naturally or non-naturally occurring amino or a peptidomimetics having similar steric properties. Where the side-chain of the native amino acid to be replaced is either polar or hydrophobic, the conservative substitution should be with a naturally occurring amino acid, a non-naturally occurring amino acid or with a peptidomimetic moiety which is also polar or hydrophobic (in addition to having the same steric properties as the side-chain of the replaced amino acid).

As naturally occurring amino acids are typically grouped according to their properties, conservative substitutions by naturally occurring amino acids can be easily determined bearing in mind the fact that in accordance with the invention replacement of charged amino acids by sterically similar non-charged amino acids are considered as conservative substitutions.

For producing conservative substitutions by non-naturally occurring amino acids it is also possible to use amino acid analogs (synthetic amino acids) well known in the art. A peptidomimetic of the naturally occurring amino acid is well documented in the literature known to the skilled practitioner.

When affecting conservative substitutions the substituting amino acid should have the same or a similar functional group in the side chain as the original amino acid.

The phrase "non-conservative substitutions" as used herein refers to replacement of the amino acid as present in the parent sequence by another naturally or non-naturally occurring amino acid, having different electrochemical and/or steric properties. Thus, the side chain of the substituting amino acid can be significantly larger (or smaller) than the side chain of the native amino acid being substituted and/or can have functional groups with significantly different electronic properties than the amino acid being substituted. Examples of non-conservative substitutions of this type include the substitution of phenylalanine or cyclohexylmethyl glycine for alanine, isoleucine for glycine, or —NH—CH[(—CH$_2$)$_5$—COOH]—CO— for aspartic acid. Those non-conservative substitutions which fall under the scope of the present invention are those which still constitute a peptide having anti-bacterial properties.

As mentioned, the N and C termini of the peptides of the present invention may be protected by function groups. Suitable functional groups are described in Green and Wuts, "Protecting Groups in Organic Synthesis", John Wiley and Sons, Chapters 5 and 7, 1991, the teachings of which are incorporated herein by reference. Preferred protecting groups are those that facilitate transport of the compound attached thereto into a cell, for example, by reducing the hydrophilicity and increasing the lipophilicity of the compounds.

These moieties can be cleaved in vivo, either by hydrolysis or enzymatically, inside the cell. Hydroxyl protecting groups include esters, carbonates and carbamate protecting groups. Amine protecting groups include alkoxy and aryloxy carbonyl groups, as described above for N-terminal protecting groups. Carboxylic acid protecting groups include aliphatic, benzylic and aryl esters, as described above for C-terminal protecting groups. In one embodiment, the carboxylic acid group in the side chain of one or more glutamic acid or aspartic acid residue in a peptide of the present invention is protected, preferably with a methyl, ethyl, benzyl or substituted benzyl ester.

Examples of N-terminal protecting groups include acyl groups (—CO—R1) and alkoxy carbonyl or aryloxy carbonyl groups (—CO—O—R1), wherein R1 is an aliphatic, substituted aliphatic, benzyl, substituted benzyl, aromatic or a substituted aromatic group. Specific examples of acyl groups include acetyl, (ethyl)-CO—, n-propyl-CO—, iso-propyl-CO—, n-butyl-CO—, sec-butyl-CO—, t-butyl-CO—, hexyl, lauroyl, palmitoyl, myristoyl, stearyl, oleoyl phenyl-CO—, substituted phenyl-CO—, benzyl-CO— and (substituted benzyl)-CO—. Examples of alkoxy carbonyl and aryloxy carbonyl groups include CH3-O—CO—, (ethyl)-O—CO—, n-propyl-O—CO—, iso-propyl-O—CO—, n-butyl-O—CO—, sec-butyl-O—CO—, t-butyl-O—CO—, phenyl-O—CO—, substituted phenyl-O—CO— and benzyl-O—CO—, (substituted benzyl)-O—CO—. Adamantan, naphtalen, myristoleyl, tuluen, biphenyl, cinnamoyl, nitrobenzoy, toluoyl, furoyl, benzoyl, cyclohexane, norbornane, Z-caproic. In order to facilitate the N-acylation, one to four glycine residues can be present in the N-terminus of the molecule.

The carboxyl group at the C-terminus of the compound can be protected, for example, by an amide (i.e., the hydroxyl group at the C-terminus is replaced with —NH$_2$, —NHR$_2$ and —NR$_2$R$_3$) or ester (i.e. the hydroxyl group at the C-terminus is replaced with —OR$_2$). R$_2$ and R$_3$ are independently an aliphatic, substituted aliphatic, benzyl, substituted benzyl, aryl or a substituted aryl group. In addition, taken together with the nitrogen atom, R$_2$ and R$_3$ can form a C4 to C8 heterocyclic ring with from about 0-2 additional heteroatoms such as nitrogen, oxygen or sulfur. Examples of suitable heterocyclic rings include piperidinyl, pyrrolidinyl, morpholino, thiomorpholino or piperazinyl. Examples of C-terminal protecting groups include —NH$_2$, —NHCH$_3$, —N(CH$_3$)$_2$, —NH(ethyl), —N(ethyl)$_2$, —N(methyl)(ethyl), —NH(benzyl), —N(C1-C4 alkyl)(benzyl), —NH(phenyl), —N(C1-C4 alkyl)(phenyl), —OCH$_3$, —O-(ethyl), —O-(n-propyl), —O-(n-butyl), —O-(iso-propyl), —O-(sec-butyl), —O-(t-butyl), —O-benzyl and —O-phenyl.

The peptides of the present invention may also comprise non-amino acid moieties, such as for example, hydrophobic moieties (various linear, branched, cyclic, polycyclic or hetrocyclic hydrocarbons and hydrocarbon derivatives) attached to the peptides; various protecting groups, especially where the compound is linear, which are attached to the compound's terminals to decrease degradation. Chemical (non-amino acid) groups present in the compound may be included in order to improve various physiological properties such; decreased degradation or clearance; decreased repulsion by various cellular pumps, improve immunogenic activities, improve various modes of administration (such as attachment of various sequences which allow penetration through various barriers, through the gut, etc.); increased specificity, increased affinity, decreased toxicity and the like.

According to one embodiment, the peptides of the present invention are attached to a sustained-release enhancing agent. Exemplary sustained-release enhancing agents include, but are not limited to hyaluronic acid (HA), alginic acid (AA), polyhydroxyethyl methacrylate (Poly-HEMA), polyethylene glycol (PEG), glyme and polyisopropylacrylamide.

Other methods of improving the penetration of peptides into cells include attachment of cell-penetrating peptides (CPPs) thereto. CPPS are short cationic peptide sequences that have been demonstrated to mediate the intracellular delivery of a range of biological cargos. They were first identified while investigating the ability of the HIV TAT transactivation protein to penetrate cells and activate HIV-1-specific genes (Jones, 2005, Br J Pharmacol 2005; 145:1093-110). Subsequent studies revealed that the minimum region required for translocation was a positively charged section between amino acids 47-57, which was associated with DNA binding (Jones, 2005, Br J Pharmacol 2005; 145:1093-1102). Since these initial observations, a range of additional CPPs have been identified including antennapedia, transportan and polyarginine. Antennapedia and TAT conjugation has been extensively used for the in vitro and in vivo delivery of biological active peptides and proteins (Lindsay, 2002 Curr Opin Pharmacol. 2002; 2:587-594).

Attaching the amino acid sequence component of the peptides of the invention to other non-amino acid agents may be by covalent linking, by non-covalent complexion, for example, by complexion to a hydrophobic polymer, which can be degraded or cleaved producing a compound capable of sustained release; by entrapping the amino acid part of the peptide in liposomes or micelles to produce the final peptide of the invention. The association may be by the entrapment of the amino acid sequence within the other component (liposome, micelle) or the impregnation of the amino acid sequence within a polymer to produce the final peptide of the invention.

The compounds of the invention may be linear or cyclic (cyclization may improve stability). Cyclization may take place by any means known in the art. Where the compound is composed predominantly of amino acids, cyclization may be via N- to C-terminal, N-terminal to side chain and N-terminal to backbone, C-terminal to side chain, C-terminal to backbone, side chain to backbone and side chain to side chain, as well as backbone to backbone cyclization. Cyclization of the peptide may also take place through non-amino acid organic moieties comprised in the peptide.

According to another embodiment, the agent capable of up-regulating DJ-1-dependent VMAT2 transcription is an activating antibody capable of specifically binding to DJ-1 and increasing the activity thereof. Methods of producing antibodies are described hereinbelow.

According to yet another embodiment, the agent capable of up-regulating DJ-1 dependent VMAT2 transcription is a cofactor which is required to bind to DJ-1 in order for the latter to bind (either directly or indirectly) to the VMAT2 promoter.

Any cell may be selected in order to identify the agent capable of up-regulating DJ-1-dependent VMAT2 transcription provided that it comprises any co-factors necessary for activating the VMAT2 promoter and does not comprise factors which may potentially down-regulate the VMAT2 promoter. An example of such a cell is a neuronal cell e.g. a neuroblastoma cell. Preferably, when the cells are used to identify agents that alter the activity of endogenous DJ-1, the cells comprise endogenous DJ-1, such as neuroblastoma cells. Alternatively, exogenous DJ-1 may be introduced into cells by transfection or the like, as further described hereinbelow.

It will be appreciated that the screening method of the present invention may also be used to identify agents comprising a neurotoxic activity. According to this aspect of the present invention, neurotoxic agents may be identified on the basis that they down-regulate DJ-1 dependent VMAT2 transcription. Such agents are typically antagonists of DJ-1, or are capable of down-regulating the activity or amount of DJ-1 (e.g. antibodies).

The peptides of the present invention can be biochemically synthesized such as by using standard solid phase techniques. These methods include exclusive solid phase synthesis, partial solid phase synthesis methods, fragment condensation, classical solution synthesis. These methods are preferably used when the peptide is relatively short (i.e., 10 kDa) and/or when it cannot be produced by recombinant techniques (i.e., not encoded by a nucleic acid sequence) and therefore involves different chemistry.

Solid phase peptide synthesis procedures are well known in the art and further described by John Morrow Stewart and Janis Dillaha Young, Solid Phase Polypeptide Syntheses (2nd Ed., Pierce Chemical Company, 1984).

Synthetic peptides can be purified by preparative high performance liquid chromatography [Creighton T. (1983) Proteins, structures and molecular principles. WH Freeman and Co. N.Y.] and the composition of which can be confirmed via amino acid sequencing.

Recombinant techniques may also be used to generate the peptides of the present invention. These techniques may be preferred when the peptide is longer than 20 amino acids and/or large amounts are required thereof. Such recombinant techniques are described by Bitter et al., (1987) Methods in Enzymol. 153:516-544, Studier et al. (1990) Methods in Enzymol. 185:60-89, Brisson et al. (1984) Nature 310:511-514, Takamatsu et al. (1987) EMBO J. 6:307-311, Coruzzi et al. (1984) EMBO J. 3:1671-1680 and Brogli et al., (1984) Science 224:838-843, Gurley et al. (1986) Mol. Cell. Biol. 6:559-565 and Weissbach & Weissbach, 1988, Methods for Plant Molecular Biology, Academic Press, NY, Section VIII, pp 421-463.

To produce an expression vector for the expression of the peptides of the present invention, a polynucleotide encoding the peptides of the present invention are ligated into a nucleic acid expression vector, which comprises the polynucleotide sequence under the transcriptional control of a cis-regulatory sequence (e.g., promoter sequence) suitable for directing constitutive, tissue specific or inducible transcription of the peptides of the present invention in the host cells.

The phrase "an isolated polynucleotide" refers to a single or double stranded nucleic acid sequence which is isolated and provided in the form of an RNA sequence, a complementary polynucleotide sequence (cDNA), a genomic polynucleotide sequence and/or a composite polynucleotide sequences (e.g., a combination of the above).

As used herein the phrase "complementary polynucleotide sequence" refers to a sequence, which results from reverse transcription of messenger RNA using a reverse transcriptase or any other RNA dependent DNA polymerase. Such a sequence can be subsequently amplified in vivo or in vitro using a DNA dependent DNA polymerase.

As used herein the phrase "genomic polynucleotide sequence" refers to a sequence derived (isolated) from a chromosome and thus it represents a contiguous portion of a chromosome.

As used herein the phrase "composite polynucleotide sequence" refers to a sequence, which is at least partially complementary and at least partially genomic. A composite sequence can include some exonal sequences required to encode the peptide of the present invention, as well as some intronic sequences interposing therebetween. The intronic sequences can be of any source, including of other genes, and typically will include conserved splicing signal sequences.

Such intronic sequences may further include cis acting expression regulatory elements.

As mentioned hereinabove, polynucleotide sequences of the present invention are inserted into expression vectors (i.e., a nucleic acid construct) to enable expression of the recombinant peptide. The expression vector of the present invention may include additional sequences which render this vector suitable for replication and integration in prokaryotes, eukaryotes, or preferably both (e.g., shuttle vectors). Typical cloning vectors contain transcription and translation initiation sequences (e.g., promoters, enhances) and transcription and translation terminators (e.g., polyadenylation signals).

A variety of prokaryotic or eukaryotic cells can be used as host-expression systems to express the peptides of the present invention. These include, but are not limited to, microorganisms, such as bacteria transformed with a recombinant bacteriophage DNA, plasmid DNA or cosmid DNA expression vector containing the peptide coding sequence; yeast transformed with recombinant yeast expression vectors containing the peptide coding sequence; plant cell systems infected with recombinant virus expression vectors (e.g., cauliflower mosaic virus, CaMV; tobacco mosaic virus, TMV) or transformed with recombinant plasmid expression vectors, such as Ti plasmid, containing the peptide coding sequence.

Other than containing the necessary elements for the transcription and translation of the inserted coding sequence (encoding the peptide), the expression construct of the present invention can also include sequences engineered to optimize stability, production, purification, yield or activity of the expressed peptide.

Various methods can be used to introduce the expression vector of the present invention into the host cell system. Such methods are generally described in Sambrook et al., Molecular Cloning: A Laboratory Manual, Cold Springs Harbor Laboratory, New York (1989, 1992), in Ausubel et al., Current Protocols in Molecular Biology, John Wiley and Sons, Baltimore, Md. (1989), Chang et al., Somatic Gene Therapy, CRC Press, Ann Arbor, Mich. (1995), Vega et al., Gene Targeting, CRC Press, Ann Arbor Mich. (1995), Vectors: A Survey of Molecular Cloning Vectors and Their Uses, Butterworths, Boston Mass. (1988) and Gilboa et al. [Biotechniques 4 (6): 504-512, 1986] and include, for example, stable or transient transfection, lipofection, electroporation and infection with recombinant viral vectors. In addition, see U.S. Pat. Nos. 5,464,764 and 5,487,992 for positive-negative selection methods.

Transformed cells are cultured under effective conditions, which allow for the expression of high amounts of recombinant peptide. Effective culture conditions include, but are not limited to, effective media, bioreactor, temperature, pH and oxygen conditions that permit protein production. An effective medium refers to any medium in which a cell is cultured to produce the recombinant peptide of the present invention. Such a medium typically includes an aqueous solution having assimilable carbon, nitrogen and phosphate sources, and appropriate salts, minerals, metals and other nutrients, such as vitamins. Cells of the present invention can be cultured in conventional fermentation bioreactors, shake flasks, test tubes, microtiter dishes and petri plates. Culturing can be carried out at a temperature, pH and oxygen content appropriate for a recombinant cell. Such culturing conditions are within the expertise of one of ordinary skill in the art.

Depending on the vector and host system used for production, resultant peptides of the present invention may either remain within the recombinant cell, secreted into the fermentation medium, secreted into a space between two cellular membranes, such as the periplasmic space in *E. coli*; or retained on the outer surface of a cell or viral membrane.

Following a predetermined time in culture, recovery of the recombinant peptide is effected.

The phrase "recovering the recombinant peptide" used herein refers to collecting the whole fermentation medium containing the peptide and need not imply additional steps of separation or purification.

Thus, peptides of the present invention can be purified using a variety of standard protein purification techniques, such as, but not limited to, affinity chromatography, ion exchange chromatography, filtration, electrophoresis, hydrophobic interaction chromatography, gel filtration chromatography, reverse phase chromatography, concanavalin A chromatography, chromatofocusing and differential solubilization.

To facilitate recovery, the expressed coding sequence can be engineered to encode the peptide of the present invention and fused cleavable moiety. Such a fusion protein can be designed so that the peptide can be readily isolated by affinity chromatography; e.g., by immobilization on a column specific for the cleavable moiety. Where a cleavage site is engineered between the polypeptide and the cleavable moiety, the peptide can be released from the chromatographic column by treatment with an appropriate enzyme or agent that specifically cleaves the fusion protein at this site [e.g., see Booth et al., Immunol. Lett. 19:65-70 (1988); and Gardella et al., J. Biol. Chem. 265:15854-15859 (1990)].

The peptide of the present invention is preferably retrieved in "substantially pure" form.

As used herein, the phrase "substantially pure" refers to a purity that allows for the effective use of the protein in the applications described herein.

In addition to being synthesizable in host cells, the peptide of the present invention can also be synthesized using in vitro expression systems. These methods are well known in the art and the components of the system are commercially available.

As mentioned hereinabove, an agent capable of regulating DJ-1-dependent VMAT2 transcription is an antibody capable of specifically binding to DJ-1.

Preferably, the antibody specifically binds at least one epitope of DJ-1. As used herein, the term "epitope" refers to any antigenic determinant on an antigen to which the paratope of an antibody binds.

Epitopic determinants usually consist of chemically active surface groupings of molecules such as amino acids or carbohydrate side chains and usually have specific three dimensional structural characteristics, as well as specific charge characteristics.

The term "antibody" as used in this invention includes intact molecules as well as functional fragments thereof, such as Fab, F(ab')2, and Fv that are capable of binding to macrophages. These functional antibody fragments are defined as follows: (1) Fab, the fragment which contains a monovalent antigen-binding fragment of an antibody molecule, can be produced by digestion of whole antibody with the enzyme papain to yield an intact light chain and a portion of one heavy chain; (2) Fab', the fragment of an antibody molecule that can be obtained by treating whole antibody with pepsin, followed by reduction, to yield an intact light chain and a portion of the heavy chain; two Fab' fragments are obtained per antibody molecule; (3) (Fab')2, the fragment of the antibody that can be obtained by treating whole antibody with the enzyme pepsin without subsequent reduction; F(ab')2 is a dimer of two Fab' fragments held together by two disulfide bonds; (4) Fv, defined as a genetically engineered fragment containing the variable region of the light chain and the variable region of the heavy chain expressed as two chains; and (5) Single chain antibody ("SCA"), a genetically engineered molecule containing the variable region of the light chain and the variable region of the heavy chain, linked by a suitable peptide linker as a genetically fused single chain molecule.

Methods of producing polyclonal and monoclonal antibodies as well as fragments thereof are well known in the art (See for example, Harlow and Lane, Antibodies: A Laboratory Manual, Cold Spring Harbor Laboratory, New York, 1988, incorporated herein by reference).

Since the agents identified according to the screening method of the present invention comprise neuromodulating activity (i.e. neuroprotecting activity or neurotoxic activity), they may be used to increase or decrease the viability of neuronal cells.

Accordingly, agents identified using the screening method of the present invention may be used to treat neurodegenerative disorders.

Examples of neurodegenerative disorders include but are not limited to Parkinson's, Multiple Sclerosis, Huntington's disease, action tremors and tardive dyskinesia, panic, anxiety, depression, alcoholism, insomnia and manic behavior, Alzheimer's and epilepsy.

It will be appreciated that the agents of the present invention may also be used to treat the effects of neurotoxins, such as environmental neurotoxins(e.g. lead, methyl mercury, polychlorinated biphenyls (PCBs), and environmental tobacco smoke).

The DJ-1 peptides of the present invention may be delivered to the subject as peptide molecules per se, or as polynucleotides where they are expressed in vivo i.e. gene therapy.

Gene therapy as used herein refers to the transfer of genetic material (e.g. DNA or RNA) of interest into a host to treat or prevent a genetic or acquired disease or condition or phenotype. The genetic material of interest encodes a product (e.g. a protein, polypeptide, peptide, functional RNA, antisense) whose production in vivo is desired. For example, the genetic material of interest can encode a hormone, receptor, enzyme, polypeptide or peptide of therapeutic value. For review see, in general, the text "Gene Therapy" (Advanced in Pharmacology 40, Academic Press, 1997).

Two basic approaches to gene therapy have evolved: (1) ex vivo and (2) in vivo gene therapy. In ex vivo gene therapy cells are removed from a patient, and while being cultured are treated in vitro. Generally, a functional replacement gene is introduced into the cell via an appropriate gene delivery vehicle/method (transfection, transduction, homologous recombination, etc.) and an expression system as needed and then the modified cells are expanded in culture and returned to the host/patient. These genetically reimplanted cells have been shown to express the transfected genetic material in situ. The cells may be autologous or non-autologous to the subject. Since non-autologous cells are likely to induce an immune reaction when administered to the body several approaches have been developed to reduce the likelihood of rejection of non-autologous cells. These include either suppressing the recipient immune system or encapsulating the non-autologous cells in immunoisolating, semipermeable membranes before transplantation.

In in vivo gene therapy, target cells are not removed from the subject rather the genetic material to be transferred is introduced into the cells of the recipient organism in situ, that is within the recipient. In an alternative embodiment, if the host gene is defective, the gene is repaired in situ (Culver, 1998. (Abstract) Antisense DNA & RNA based therapeutics, February 1998, Coronado, Calif.).

These genetically altered cells have been shown to express the transfected genetic material in situ.

To confer specificity, preferably the nucleic acid constructs used to express the peptides of the present invention comprise cell-specific promoter sequence elements.

As mentioned hereinabove, the peptides of the present invention may be delivered to the subject as peptide molecules.

It will further be appreciated that delivery of peptide agents to the brain is restricted by the blood brain barrier. Over the years, several strategies to circumvent the blood brain barrier have been proposed, such as by transient osmotic opening of the BBB, high dosing (e.g., of chemotherapy), use of carrier systems such as antibodies, or even biodegradable implants. All these systems are contemplated by the present invention.

Furthermore, several synthetic NP polymers, arranged as spheres have been studied as carriers of drugs across the BBB. Poly(butyl cyanoacrylate) has been reported to effectively deliver different drugs, including peptides [Kreuter J. Adv. Drug Delivery Rev. 2001, 47:65-81; Gulayev A E, et al., Pharm Res 1999, 16:1564-9].

It has also been suggested that liposomes can enhance drug delivery to the brain across the blood-brain barrier [Umezawa and Eto, Biochem. Biophys. Res. Comm. 153:1038-1044 (1988); Chan et al., Ann. Neurol, 21:540-547 (1987); Laham et al., Life Sciences 40:2011-2016 (1987); and Yagi et al., J. APRIo Biocheme 4:121-125 (1982)]. Liposomes are small vesicles (usually submicron sized) comprised of one or more concentric bilayers of phospholipids separated by aqueous compartments.

It has been suggested that the use of an external ligand such as mannose can improve a liposomal particle's ability to cross the BBB [Huiting a et al., J exp Med 172 (1990) 1025-33; Umezawa F., Biochem Biophys Res Commun 153 (1988) 1038-44]. The mannosylated liposomes were shown to be incorporated in glial cells as opposed to neuronal cells, the former having a receptor for mannose [Umezawa F., Biochem Biophys Res Commun 153, 1988, 1038-44]. PCT Application, Publication No. WO9402178A1 to Micklus discusses the coupling of liposomes to an antibody binding fragment which binds to a receptor molecule present on the vascular endothelial cells of the mammalian blood-brain barrier. The peptides perhaps may also be delivered by phages, intranasally for example.

The DJ-1 regulating agents of the present invention may be delivered to the subject per se or as part of a pharmaceutical composition.

As used herein a "pharmaceutical composition" refers to a preparation of one or more of the active ingredients described herein with other chemical components such as physiologically suitable carriers and excipients. The purpose of a pharmaceutical composition is to facilitate administration of a compound to an organism.

Herein the term "active ingredient" refers to the DJ-1 peptides of the present invention accountable for the biological effect.

Hereinafter, the phrases "physiologically acceptable carrier" and "pharmaceutically acceptable carrier" which may be interchangeably used refer to a carrier or a diluent that does not cause significant irritation to an organism and does not abrogate the biological activity and properties of the administered compound. An adjuvant is included under these phrases.

Herein the term "excipient" refers to an inert substance added to a pharmaceutical composition to further facilitate administration of an active ingredient. Examples, without limitation, of excipients include calcium carbonate, calcium phosphate, various sugars and types of starch, cellulose derivatives, gelatin, vegetable oils and polyethylene glycols.

Pharmaceutical compositions of the present invention may be manufactured by processes well known in the art, e.g., by means of conventional mixing, dissolving, granulating, dragee-making, levigating, emulsifying, encapsulating, entrapping or lyophilizing processes.

Pharmaceutical compositions for use in accordance with the present invention thus may be formulated in conventional manner using one or more physiologically acceptable carriers comprising excipients and auxiliaries, which facilitate processing of the active ingredients into preparations which, can be used pharmaceutically. Proper formulation is dependent upon the route of administration chosen.

For injection, the active ingredients of the pharmaceutical composition may be formulated in aqueous solutions, preferably in physiologically compatible buffers such as Hank's solution, Ringer's solution, or physiological salt buffer.

Herein the term "excipient" refers to an inert substance added to a pharmaceutical composition to further facilitate administration of an active ingredient. Examples, without limitation, of excipients include calcium carbonate, calcium phosphate, various sugars and types of starch, cellulose derivatives, gelatin, vegetable oils and polyethylene glycols.

Techniques for formulation and administration of drugs may be found in "Remington's Pharmaceutical Sciences," Mack Publishing Co., Easton, Pa., latest edition, which is incorporated herein by reference.

Suitable routes of administration may, for example, include oral, rectal, transmucosal, especially transnasal, intestinal or parenteral delivery, including intramuscular, subcutaneous and intramedullary injections as well as intrathecal, direct intraventricular, intravenous, inrtaperitoneal, intranasal, or intraocular injections.

Alternately, one may administer the pharmaceutical composition in a local rather than systemic manner, for example, via injection of the pharmaceutical composition directly into a tissue region of a patient i.e. the brain. The compositions of the present invention can be directly administered to any structure in the brain. In one embodiment, the compositions are administered to brain structures selected from the group consisting of substantia nigra, hippocampus, striatum, and cortex. In another embodiment of the invention, the composition is administered using a stereotactic device.

Pharmaceutical compositions of the present invention may be manufactured by processes well known in the art, e.g., by means of conventional mixing, dissolving, granulating, dragee-making, levigating, emulsifying, encapsulating, entrapping or lyophilizing processes.

Pharmaceutical compositions for use in accordance with the present invention thus may be formulated in conventional manner using one or more physiologically acceptable carriers comprising excipients and auxiliaries, which facilitate processing of the active ingredients into preparations which, can be used pharmaceutically. Proper formulation is dependent upon the route of administration chosen.

For injection, the active ingredients of the pharmaceutical composition may be formulated in aqueous solutions, preferably in physiologically compatible buffers such as Hank's solution, Ringer's solution, or physiological salt buffer. For transmucosal administration, penetrants appropriate to the barrier to be permeated are used in the formulation. Such penetrants are generally known in the art.

The pharmaceutical composition described herein may be formulated for parenteral administration, e.g., by bolus injection or continuous infusion. Formulations for injection may be presented in unit dosage form, e.g., in ampoules or in multidose containers with optionally, an added preservative. The compositions may be suspensions, solutions or emulsions in oily or aqueous vehicles, and may contain formulatory agents such as suspending, stabilizing and/or dispersing agents.

Pharmaceutical compositions for parenteral administration include aqueous solutions of the active preparation in water-soluble form. Additionally, suspensions of the active ingredients may be prepared as appropriate oily or water based injection suspensions. Suitable lipophilic solvents or vehicles include fatty oils such as sesame oil, or synthetic fatty acids esters such as ethyl oleate, triglycerides or liposomes. Aqueous injection suspensions may contain substances, which increase the viscosity of the suspension, such as sodium carboxymethyl cellulose, sorbitol or dextran. Optionally, the suspension may also contain suitable stabilizers or agents which increase the solubility of the active ingredients to allow for the preparation of highly concentrated solutions.

Alternatively, the active ingredient may be in powder form for constitution with a suitable vehicle, e.g., sterile, pyrogen-free water based solution, before use.

Pharmaceutical compositions suitable for use in context of the present invention include compositions wherein the active ingredients are contained in an amount effective to achieve the intended purpose. More specifically, a therapeutically effective amount means an amount of active ingredients effective to prevent, alleviate or ameliorate symptoms of a disorder (e.g., neurodegenerative disorder) or prolong the survival of the subject being treated.

Determination of a therapeutically effective amount is well within the capability of those skilled in the art, especially in light of the detailed disclosure provided herein.

For any preparation used in the methods of the invention, the therapeutically effective amount or dose can be estimated from animal models to achieve a desired concentration or titer. Such information can be used to more accurately determine useful doses in humans.

Toxicity and therapeutic efficacy of the active ingredients described herein can be determined by standard pharmaceutical procedures in experimental animals.

For example, 6-OHDA-lesioned mice may be used as animal models of Parkinson's. In addition, a sunflower test may be used to test improvement in delicate motor function by challenging the animals to open sunflowers seeds during a particular time period.

Transgenic mice may be used as a model for Huntingdon's disease which comprise increased numbers of CAG repeats have intranuclear inclusions of huntingtin and ubiquitin in neurons of the striatum and cerebral cortex but not in the brain stem, thalamus, or spinal cord, matching closely the sites of neuronal cell loss in the disease.

Transgenic mice may be used as a model for ALS disease which comprise SOD-1 mutations.

The septohippocampal pathway, transected unilaterally by cutting the fimbria, mimics the cholinergic deficit of the septohippocampal pathway loss in Alzheimers disease. Accordingly animal models comprising this lesion may be used to test the cells of the present invention for treating Alzheimers.

In general, schizophrenia animal models can be divided in three categories, i.e. models that investigate behaviours in animals that are disturbed in schizophrenic patients (e.g. prepulse inhibition of the acoustic startle response and latent inhibition), pharmacological models, and experimentally induced brain pathology e.g. brain lesion models. Methods of generating such models and use of same are described in Bachevalier, J. (1994) Medial temporal lobe structures and autism, a review of clinical and experimental findings. Neuropsychologia 32, 627-648; R. Joober et al. Genetic of schizophrenia: from animal models to clinical studies. J. Psychiatry Neurosci. 2003; 27 (5): 336-47; Lipska, B. K., Jaskiw, G. E., Weinberger, D. R., 1993, Postpuberal emergence of hyperresponsiveness to stress and to amphetamine after neonatal hippocampal damage, a potential animal model for schizophrenia. Neuropsychopharmacol. 122, 35-43; Weinberger, R. R. (1987) Implications of normal brain development for the pathogenesis of schizophrenia. Arch. Gen. Psychiatry 44: 660-669; Wolterink G., Daenen, E. W. P. M., Dubbeldam, S., Gerrits, M. A. F. M., Van Rijn, R., Kruse, C. G., Van der Heijden, J., Van Ree, J. M. (2001) Early amygdala damage in the rat as model for neurodevelopmental psychopathological. Eur. Neuropsychopharmacol. 11, 51-59; and Daenen E. W. P. M., Wolterink G., Gerrits M. A. F. M., Van Ree J. M. (2002) Amygdala or ventral hippocampal lesions at two early stages of life differentially affect open filed behaviour later in life: an animal model of neurodevelopmental psychopathological disorders. Behavioral Brain Research 131: 67-78, each of which is fully incorporated herein by reference.

The data obtained from these animal studies can be used in formulating a range of dosage for use in human. The dosage may vary depending upon the dosage form employed and the route of administration utilized. The exact formulation, route of administration and dosage can be chosen by the individual physician in view of the patient's condition. (See e.g., Fingl, et al., 1975, in "The Pharmacological Basis of Therapeutics", Ch. 1 p. 1).

Dosage amount and interval may be adjusted individually to provide cell numbers sufficient to induce normoglycemia (minimal effective concentration, MEC). The MEC will vary for each preparation, but can be estimated from in vitro data. Dosages necessary to achieve the MEC will depend on individual characteristics and route of administration. Detection assays can be used to determine plasma concentrations.

The amount of a composition to be administered will, of course, be dependent on the subject being treated, the severity of the affliction, the manner of administration, the judgment of the prescribing physician, etc.

Compositions of the present invention may, if desired, be presented in a pack or dispenser device, such as an FDA approved kit, which may contain one or more unit dosage forms containing the active ingredient. The pack may, for example, comprise metal or plastic foil, such as a blister pack. The pack or dispenser device may be accompanied by instructions for administration. The pack or dispenser may also be accommodated by a notice associated with the container in a form prescribed by a governmental agency regulating the manufacture, use or sale of pharmaceuticals, which notice is reflective of approval by the agency of the form of the compositions or human or veterinary administration. Such notice, for example, may be of labeling approved by the U.S. Food and Drug Administration for prescription drugs or of an approved product insert. Compositions comprising a preparation of the invention formulated in a compatible pharmaceutical carrier may also be prepared, placed in an appropriate container, and labeled for treatment of an indicated condition, as if further detailed above.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Reference is now made to the following examples, which together with the above descriptions, illustrate the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683, 202; 4,801,531; 5,192,659 and 5,272,057; "Cell Biology: A Laboratory Handbook", Volumes I-III Cellis, J. E., ed. (1994); "Culture of Animal Cells—A Manual of Basic Technique" by Freshney, Wiley-Liss, N.Y. (1994), Third Edition; "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

General Materials and Methods

Cellular transfection and treatment: SH-SY5Y human neuroblastoma cells, obtained from the ATCC (Rockville, USA), were stably transfected with pIRES2-acGFP1 plasmid (BD biosciences, Clontech) containing wild type DJ-1. Decreased expression of DJ-1 was achieved by stable transfection with pSilencer2.1-U6 plasmid (Ambion) containing siRNA for DJ-1. As controls, naïve neuroblastoma cells were used as well as cells stably transfected with the same vectors. Transfections were performed using the lipofectamine 2000 reagent (Invitrogen). Stable transfections were achieved by geneticin treatment and were verified by measuring DJ-1 mRNA and protein levels using real-time PCR and Western blotting.

Cells were treated with dopamine (0-500 uM; Sigma. Israel), N-acetylcysteine (NAC 5 mM; Sigma), and PD-98059 (30 uM; Calbiochem, Rosh Haayin, Israel).

In vivo 6-hydroxydopamine hemiparkinsonian mouse model: Eight-week-old male C57BL/6 mice (Harlan, Israel; 22-28 g) were used for 6-hydroxydopamine hemiparkinsonian mouse model experiments. All animals were housed in standard conditions, in a constant temperature (22±1° C.), relative humidity (30%), 12-h light: 12-h dark cycle, with free access to food and water. Surgical procedures were performed under the supervision of the Animal Care Committee at the Rabin Medical Center and at Tel Aviv University, Tel Aviv, Israel. Mice received a unilateral, right intrastriatal injection of 4 pg 6-hydroxydopamine hydrobromide (Sigma, Israel) using a stereotaxic surgical procedure. Injections were targeted to the central striatum using the following coordinates: 0.5 mm anterior to bregma, 2.0 mm lateral to bregma, and 2.5 mm deep to the skull surface. Treatments were administered in a volume of 2.0 µL at a rate of 0.5 µL/min. 24 hours after 6-hydroxydopamine lesioning, striatal tissue was collected from both the injected and intact sides for DJ-1, VMAT2 and TH analysis. For analysis of acute 6-hydroxydopamine effects on phosphokinases striatal tissue was excised after 30 and 45 minutes of 6-hydroxydopamine injection.

Protein extraction and Western blotting: Protein extraction and Western blotting were done as previously described [Lev, N., et al Antioxid. redox signal. 8, 1987-1995 (2006)]. The membranes were probed with rabbit anti-DJ 1 antibody (1:1000; Chemicon Laboratories), mouse anti-VMAT2 (1:100; Chemicon Laboratories), and rabbit anti emerin (1:5000; Santa Cruz), followed by horseradish peroxidase conjugated secondary antibody (1:10000; Sigma) and developed with the Super Signal West Pico Chemiluminescent substrate (Pierce Biotechnology). Densitometry of the specific protein bands was preformed by VersaDoc® imaging system and Quantity One® software (BioRad).

RNA isolation and Real time quantitative PCR: Total RNA was isolated from cultured neuroblastoma cells using a commercial reagent TriReagent™ (Sigma). The amount and quality of RNA was determined spectrophotometrically using the ND-1000 spectrophotometer (NanoDrop). First-strand cDNA synthesis was carried out from 1 pg of the total RNA using random primer (Invitrogen) and RT-superscript II (Invitrogen) reverse transcriptase. Real-time quantitative reverse transcription polymerase chain reaction (PCR) of the desired genes was performed in an ABI Prism 7700 sequence detection system (Applied biosystems) using Sybr green PCR master mix (Applied biosystems) and the following primers: GAPDH (used as 'housekeeping' gene) sense: CGACAGTCAGCCGCATCTT (SEQ ID NO: 7), GAPDH antisense: CCAATACGACCAAATCCGTTG (SEQ ID NO: 8); DJ-1 sense: CATGAGGCGAGCTGGGATTA, (SEQ ID NO: 9) DJ-1 antisense: GCTGGCATCAGGACAAATGAC, (SEQ ID NO:10) VMAT2 sense: GGACAACATGCTGCTCACTG, (SEQ ID NO: 11) VMAT2 antisense: ATTCCCGGTGACCATAGTCG (SEQ ID NO: 12). Real time quantitative PCR (qPCR) was performed using Absolute™ QPCR SYBR® Green ROX Mix, in triplicates. Quantitative calculations of the gene of interest versus GAPDH were done using the ddCT method.

Immunocytochemistry: Cells were fixed with 4% paraformaldehyde and permeabilized with 0.5% Triton X-100 and were then incubated in a blocking solution followed by overnight incubation with rabbit anti-VMAT2 (1:100; Chemicon Laboratories), at 4° C. followed by incubation with alexa-568 conjugated goat anti rabbit antibodies (1:1000; Molecular probes). Nuclei were counterstained by 4',6-Diamidino-2-phenylindole dihydrochloride (DAPI, Sigma).

Cell viability: Cell viability was determined by the MTT (3-(4,5-dimethylthiazole-2-yl)-2,5-diphenyltetrazolium bromide, Sigma) reduction assay. Viability after exposure to increasing dopamine levels was analyzed by adding MIT solution to each well followed by incubation at 37° C. for 3 hours. Absorbance was determined at 564 nm in a microplate reader. Cell viability was evaluated in triplicate for each treatment. All experiments were repeated at least 3 times.

Measurement of intracellular reactive oxygen species (ROS): The generation of ROS, after exposure to increasing dopamine concentrations, was measured using H2DCFDA (Sigma), which is incorporated into the cells and cleaved into fluorescent DCF in the presence of ROS. 10 µM H2DCFDA was added to the cell suspension, and the cells were incubated in the dark at 37° C. for 10 minutes. DCF fluorescence was measured by FLUOstar spectrofluorometer microplate reader at 520 nm. The generation of ROS was quantitatively assayed by the increase in DCF fluorescence and expressed as percentage of control. Each experiment was repeated at least 3 times in triplicates.

KCl-induced dopamine release: Cells were plated on poly-D-lysin-coated 24-well plates. Cells were rinsed with assay buffer (containing Tris 4 mM, HEPES 6.25 mM, NaCl 120 mM, KCl 5 mM, CaCl2 1.2 mM, MgSO4 1.2 mM, D-glucose 5.6 mM and ascorbic acid 0.5 mM) and were then incubated with 0.5 uCi/ml [3H]Dopamine (Amersham Biosciences) for 20 minutes at 37° C. To measure stimulation-induced [3H] Dopamine release, [3H]Dopamine-loaded cells were rinsed extensively with ice cold buffer, and were treated with 60 mM KCl for 20 minutes at 37° C. and extracellular [3H]Dopamine was measured. Inhibition of VMAT2 was done using dihydrotetrabenazine (0-1 mM). All samples were analyzed with Packard liquid scintillation counter. Experiments were conducted in triplicates and repeated three times.

Chromatin immunoprecipitation: ChIP assays using cultured neuroblastoma cells were performed following Upstate instructions. After protein-DNA cross-linking by paraformaldehyde, cells were harvested and the pellets were resuspended in lysis-buffer and sonicated on ice (5 sets of 15-s pulse at 40% maximal power). After pre-clearing with Protein G/A-agarose, aliquots were incubated with DJ-1 antibodies or non-specific antibodies (as control) overnight at 4° C. with rotation. Immunopercipitated DNA was used as templates for the following primers, designed for the human VMAT promotor: sense: AGGCGAGGGCTAAGATGTTT (SEQ ID NO: 13); antisense: ACGTGGGGTCCCAGTTACTT (SEQ ID NO: 14) and for TH promotor: sense: GAGCCTTCCTGGTGTTTGTG (SEQ ID NO: 15); antisense: CTCTCCGATTCCAGATGGTG (SEQ ID NO: 16).

Statistical analysis: Comparisons of two groups were conducted using a 2-tailed Student's t test. Statistical analyses among three or more groups were performed using analysis of variance (ANOVA) followed by least-significant difference (LSD) post hoc comparison. Differences among groups were considered significant if the probability (P) of error was less than 5%.

Example 1

The Parkinson's Disease-associated DJ-1 Protein Protects Against Dopamine Toxicity by Upregulating Vesicular Monoamine Transporter-2

Loss-of-function DJ-1 mutations are linked to the degeneration of dopaminergic neurons and PD. Therefore, the present inventors hypothesized that decreasing DJ-1 levels by siRNA for DJ-1 may predispose dopaminergic SH-SY5Y neuroblastoma cells to dopamine-induced cell death, while overexpression of DJ-1 may have a protective effect. To test this hypothesis, cells were generated which either overexpressed DJ-1 or expressed siRNA for DJ-1 thereby decreasing DJ-1 levels. Expression levels of DJ-1 mRNA and protein in these lines were evaluated by quantitative real time PCR and by Western blotting (FIGS. 1A-B). Exposure of neuroblastoma cells to increasing doses of dopamine resulted in cell death. Dopamine-induced cell death was dependent on DJ-1 expression levels; over-expression of DJ-1 protected neuroblastoma cells from the toxic effect of dopamine, while decreasing DJ-1 levels by siRNA resulted in increased vulnerability to dopamine exposure (FIG. 1A). To analyze whether dopamine toxicity was mediated through oxidative stress, intracellular ROS was measured. Exposure of cells to increasing doses of dopamine caused a rise in oxidative stress as indicated by increased intracellular ROS (FIG. 1B). Overexpression of DJ-1 reduced intracellular ROS after dopamine exposure while reducing DJ-1 expression levels by siRNA resulted in elevated intracellular ROS accumulation (FIG. 1B). Similarly, it was found that susceptibility of neuroblastoma cells to other dopaminergic neurotoxins such as rotenone and 6-hydroxydopamine was dependent on DJ-1 levels and that enhanced DJ-1 expression reduced the intracellular ROS caused by these toxins (FIGS. 8A-B). Furthermore, it found that naïve neuroblastoma cells augment DJ-1 expression levels in response to dopamine. Exposure to 50 μM dopamine resulted in a rapid increase in DJ-1 mRNA levels which occurred within 1 hour (FIG. 2A). Increased DJ-1 protein after dopamine exposure was detected as well using Western blot (FIG. 2B). Pretreatment with the antioxidant N-acetyl-cysteine (NAC) abolished the upregulation of DJ-1 induced by dopamine exposure (FIGS. 2A-B), suggesting that the upregulation of DJ-1 is mediated by intracellular ROS generation. Intracellular increases in DJ-1 levels may serve to protect the cells from the toxic effect of dopamine, as shown in FIGS. 1A-B.

Recent reports indicate that protein kinases, especially the mitogen-activated protein kinases (MAPK) participate in the critical steps of neurotoxic cascades (Leak et al., 2006, J Neurochem 99:1151-1163). Therefore, the possible involvement of MAPK in the signal transduction pathway that leads to upregulation of DJ-1 was investigated. Dopamine exposure led to a rapid phosphorylation of extracellular signal-regulated kinase (ERK) 1 and 2 (FIGS. 10A-C). ERK1, 2 activation preceded upregulation of DJ-1 mRNA. Inhibition of ERK1,2-MAPK by PD-98059 attenuated dopamine-induced DJ-1 upregulation, as shown by real time PCR and Western blotting (FIGS. 10D-E). These experiments indicate that dopamine exposure leads to rapid activation of ERK 1, 2, leading to DJ-1 upregulation.

Next, vesicular monoamine transporter-2 (VMAT2) levels were examined to ascertain whether increased DJ-1 levels confer resistance to dopamine toxicity via sequestration of dopamine into the synaptic vesicles. It was found that overexpression of DJ-1 resulted in a dramatic increase—over 500-fold—in the vesicular monoamine transporter-2 (VMAT2) expression level compared to control VMAT2 levels (FIG. 3A). Decreased DJ-1 levels, through siRNA for DJ-1, resulted in reduced VMAT2 levels (FIG. 3A). This correlation between VMAT2 and DJ-1 expression levels was also confirmed by Western blotting (FIG. 3B) and immunocytochemical staining (FIGS. 3C-E). In order to further verify that upregulation of DJ-1 leads to upregulation of VMAT2, naïve neuroblastoma cells were exposed to dopamine and DJ-1, and VMAT2 mRNA levels were quantified at different intervals. Exposure to 50 μM dopamine led to a 2.5-fold increase in DJ-1 mRNA within 1 hour (FIG. 4A). After 7 hours, VMAT2 mRNA was elevated 60-fold of basal level (FIG. 4B). This kinetics pattern indicates that dopamine exposure leads to DJ-1 upregulation which is followed by VMAT2 upregulation. These events may be mediated via transcriptional regulation of VMAT2 expression by DJ-1.

To examine this possibility, a chromatin immunoprecipitation assay was performed to assess the physical interaction between DJ-1 and VMAT2 promotor. The DNA immunoprecipitated by anti-DJ-1 antibodies was amplified by primers specifically recognizing VMAT2 promotor, while no amplification of VMAT2 promotor was detected when immunopercipitation was done using non specific IgG (FIG. 4C). Moreover, after exposure to 50 μM dopamine, higher amounts of VMAT2 promotor were precipitated by anti-DJ-1 antibodies, implying that DJ-1 activates VMAT2 transcription in response to dopamine exposure (FIG. 4C). Taken together, these results demonstrate that DJ-1 regulates VMAT2 expression and that increased cytoplasmic dopamine results in upregulation of VMAT2 transcription through DJ-1. Additionally, it was found that DJ-1 upregulates another gene important in dopamine homeostasis, tyrosine hydroxylase, the rate limiting enzyme in dopamine synthesis (FIGS. 9A-B). In order to assess the functional changes in VMAT2 activity, [3H]dopamine release from the synaptic vesicles was stimulated by KCl-induced depolarization.

The dopamine release assay revealed that DJ-1 overexpressing neuroblastoma cells released more dopamine from the synaptic vesicles compared to naïve neuroblastoma cells, while cells transfected with siRNA for DJ-1 released less dopamine (FIG. 4D). KCl induced dopamine release was abolished by dihydrotetrabenazine, a VMAT2 inhibitor, indicating that the assay indeed measures VMAT2 function. This functional assay indicates that vesicular dopamine storage is dependent on DJ-1 expression levels.

Next, the present inventors examined whether ROS also induces upregulation of DJ-1 in vivo. In order to evaluate such in vivo changes, a hemiparkinsonian mouse model induced by unilateral intrastriatal 6-hydroxydopamine lesioning was used. An increased expression of DJ-1 and of VMAT-2 proteins was found, 24 hours following 6-hydroxydopamine injection in the lesioned striatum as compared to the unlesioned side (FIG. 11A). Consistent with the in vitro results, acute exposure to 6-hydroxydopamine led to the increased phosphorylation of ERK1, 2 (FIG. 11B).

CONCLUSION

This study suggests a novel mechanism through which DJ-1 mutations may be associated with increased vulnerability of dopaminergic neurons leading to their degeneration in PD. It was found that DJ-1 regulates intracytoplasmic dopamine levels by controlling the expression of the vesicular dopamine transporter, VMAT2.

Overexpression of DJ-1 led to increased resistance to dopamine toxicity mediated by increased dopamine sequestration into synaptic vesicles by VMAT2, and therefore decreased intracellular ROS. Reducing DJ-1 levels by siRNA to DJ-1 led to the opposite effects, decreasing VMAT2 expression levels as well as its function, combined with increased intracellular ROS and a rise in the susceptibility to dopamine toxicity. Moreover, it was found that exposure of naïve neuroblastoma cells to dopamine leads to rapid upregulation of DJ-1, followed by upregulation of VMAT2. It was shown using chromatin immunoprecipitation assay, that DJ-1 binds to the VMAT2 promotor and that this binding is enhanced by dopamine. Hence, DJ-1 upregulation is vital in dopaminergic neurons in order to sequestrate excess dopamine into synaptic vesicles and thus protect the cells from cytoplasmic accumulation of dopamine-induced ROS. Oxidative-induced changes in DJ-15 imply that DJ-1 may serve as a sensor for increased cytoplasmic levels of ROS, and its rapid upregulation may be a first line defense mechanism of dopaminergic neurons that acts to rapidly clear away free cytosolic dopamine by taking it up into the synaptic vesicles.

Moreover, apart from the accumulation of dopamine into the synaptic vesicles, VMAT2 also provides neuroprotection by sequestering into cytoplasmic vesicles external toxins implicated in PD pathogenesis, such as 1-methyl-4-phenylpyridinium (MPP+). Overexpression of VMAT2 confers protection against these toxic insults, while genetic and pharmacological blockade of VMAT2 renders dopaminergic neurons more susceptible. These studies imply that the dopamine sequestration mechanism may also function to protect dopaminergic neurons from exposure to environmental toxins. Therefore, DJ-1 dysfunction may also augment dopaminergic neuronal vulnerability to damaging environmental factors. Therefore, on one hand, mutations in DJ-1 cause hereditary PD while on the other hand, the present findings suggest that malfunction of wild type DJ-1 may also predispose neuron to damage induced by exposure to external noxious agents. To conclude, the findings presented suggest a novel mechanism in which ROS, generated by free cytoplasmic dopamine, lead to rapid upregulation of DJ-1, which in turn protectively augment the sequestration of dopamine into the synaptic vesicles through upregulation of VMAT2. This mechanism explains how mutations in DJ-1 trigger early onset PD and suggest that DJ-1 dysfunction may also be involved in the pathogenesis of sporadic PD.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

What is claimed is:

1. An isolated peptide being no more than 14 amino acids long and further comprising the sequence as set forth in SEQ ID NO: 133.

2. A method of treating a neurodegenerative disorder, the method comprising administering to an individual in need thereof a therapeutically effective amount of the isolated peptide of claim 1, thereby treating the neurodegenerative disorder.

3. An isolated peptide comprising a neuroprotecting peptide attached to a cell penetrating peptide, wherein said neuroprotecting peptide is no more than 14 amino acids long and further comprises the sequence as set forth in SEQ ID NO: 133.

4. A method of treating a neurodegenerative disorder, the method comprising administering to an individual in need thereof a therapeutically effective amount of the isolated peptide of claim 3, thereby treating the neurodegenerative disorder.

5. A pharmaceutical composition comprising the isolated peptide of claim 1 as an active agent and a pharmaceutically acceptable carrier.

6. A pharmaceutical composition comprising the isolated peptide of claim 3 as an active agent and a pharmaceutically acceptable carrier.

* * * * *